United States Patent
Bauer et al.

(10) Patent No.: US 11,524,158 B2
(45) Date of Patent: Dec. 13, 2022

(54) IMPLANTABLE MEDICAL SYSTEMS, DEVICES, AND METHODS FOR AFFECTING CARDIAC FUNCTION THROUGH DIAPHRAGM STIMULATION, AND FOR MONITORING DIAPHRAGMATIC HEALTH

(71) Applicant: VisCardia, Inc., Beaverton, OR (US)

(72) Inventors: Peter T. Bauer, Portland, OR (US); Timothy Wheeler, Portland, OR (US)

(73) Assignee: VisCardia, Inc., Beaverton, OR (US)

( * ) Notice: Subject to any disclaimer, the term of this patent is extended or adjusted under 35 U.S.C. 154(b) by 67 days.

(21) Appl. No.: 17/029,768

(22) Filed: Sep. 23, 2020

(65) Prior Publication Data

US 2021/0093859 A1    Apr. 1, 2021

Related U.S. Application Data

(60) Provisional application No. 62/906,682, filed on Sep. 26, 2019.

(51) Int. Cl.
| | |
|---|---|
| *A61N 1/36* | (2006.01) |
| *A61N 1/05* | (2006.01) |
| *A61B 5/00* | (2006.01) |
| *A61B 5/349* | (2021.01) |

(Continued)

(52) U.S. Cl.
CPC ............ *A61N 1/3601* (2013.01); *A61B 5/349* (2021.01); *A61B 5/389* (2021.01); *A61B 5/7282* (2013.01);
(Continued)

(58) Field of Classification Search
CPC ............ A61N 1/36003; A61N 1/36135; A61B 5/349; A61B 5/389; A61B 5/7282;
(Continued)

(56) References Cited

U.S. PATENT DOCUMENTS

| | | | |
|---|---|---|---|
| 4,411,268 A | 10/1983 | Cox | |
| 5,098,442 A | 3/1992 | Grandjean | |

(Continued)

FOREIGN PATENT DOCUMENTS

| | | | |
|---|---|---|---|
| CA | 1256507 A | 6/1989 | |
| EP | 1588735 A1 | 10/2005 | |

(Continued)

OTHER PUBLICATIONS

Beeler et al. "Improvement of cardiac function with device-based diaphragmatic stimulation in chronic heart failure patients: the randomized, open-label, crossover Epiphrenic II pilot trial." Euro. J. of Heart Failure 16, 342-349 (2014).

(Continued)

*Primary Examiner* — Carl H Layno
*Assistant Examiner* — Anh-Khoa N Dinh
(74) *Attorney, Agent, or Firm* — Loza & Loza, LLP; David S. Sarisky

(57) ABSTRACT

Devices, systems and methods provide forms of asymptomatic diaphragmatic stimulation (ADS) therapy that affect pressures within the intrathoracic cavity, including: 1) dual-pulse ADS therapy, during which a first ADS pulse is delivered during a diastolic phase of a cardiac cycle and a second ADS pulse is delivered during a systolic phase, 2) paired-pulse ADS therapy, during which a first ADS pulse is delivered, closely followed by a second ADS pulse, with the second ADS pulse functioning to extend or enhance a phase of a transient, partial contraction of the diaphragm, and 3) multiple-pulse ADS therapy, during which a stream of ADS pulses is delivered, wherein the time between pulses is based on heart rate. Devices, systems and methods also monitor electromyography (EMG) activity of the diaphragm relative to baseline activity to assess the health of a diaphragm (Continued)

subject to ADS therapy and to adjust ADS therapy parameters or sensing parameters.

17 Claims, 21 Drawing Sheets

(51) Int. Cl.
  *A61N 1/08*  (2006.01)
  *A61N 1/365* (2006.01)
  *A61B 5/389* (2021.01)
  *A61N 1/02*  (2006.01)

(52) U.S. Cl.
  CPC ............... *A61N 1/05* (2013.01); *A61N 1/08* (2013.01); *A61N 1/36003* (2013.01); *A61N 1/36135* (2013.01); *A61N 1/36507* (2013.01); *A61N 1/025* (2013.01); *A61N 1/36542* (2013.01); *A61N 1/36578* (2013.01); *A61N 1/36585* (2013.01)

(58) Field of Classification Search
  CPC ......... A61B 5/6869; A61B 5/24; A61B 5/352; A61B 5/363; A61B 5/7264
  See application file for complete search history.

(56) References Cited

U.S. PATENT DOCUMENTS

| | | |
|---|---|---|
| 5,188,098 A | 2/1993 | Hoffman et al. |
| 5,300,094 A | 4/1994 | Kallok |
| 5,358,519 A | 10/1994 | Grandjean |
| 5,392,780 A | 2/1995 | Ogino et al. |
| 5,632,716 A | 5/1997 | Bui |
| 5,693,000 A | 12/1997 | Crosby |
| 5,758,654 A | 6/1998 | Burton-Krahn et al. |
| 5,814,086 A | 9/1998 | Hirschberg |
| 6,415,183 B1 | 7/2002 | Scheiner |
| 6,979,297 B2 | 12/2005 | Andresen et al. |
| 7,039,538 B2 | 5/2006 | Baker, Jr. |
| 7,072,708 B1 | 7/2006 | Andresen et al. |
| 7,074,195 B2 | 7/2006 | Nelson et al. |
| 7,096,060 B2 | 8/2006 | Arand et al. |
| 7,096,064 B2 | 8/2006 | Deno et al. |
| 7,113,820 B2 | 9/2006 | Schlegel et al. |
| 7,171,269 B1 | 1/2007 | Addison et al. |
| 7,174,203 B2 | 2/2007 | Arand et al. |
| 7,225,021 B1 | 5/2007 | Park et al. |
| 7,248,923 B2 | 7/2007 | Maile et al. |
| 7,277,757 B2 | 10/2007 | Casavant |
| 7,302,290 B2 | 11/2007 | Bauer |
| 7,357,775 B1 | 4/2008 | Koh |
| 7,424,321 B2 | 9/2008 | Wariar et al. |
| 7,435,221 B1 | 10/2008 | Bhami et al. |
| 7,437,699 B2 | 10/2008 | Morita et al. |
| 7,467,012 B1 | 12/2008 | Park et al. |
| 7,559,903 B2 | 7/2009 | Moussavi et al. |
| 7,668,589 B2 | 2/2010 | Bauer |
| 7,725,181 B1 | 5/2010 | Bornzin et al. |
| 7,819,814 B2 | 10/2010 | Gavirely et al. |
| 7,979,128 B2 | 7/2011 | Tehrani et al. |
| 7,994,655 B2 | 8/2011 | Bauer et al. |
| 8,065,002 B2 | 11/2011 | Arand et al. |
| 8,105,241 B2 | 1/2012 | Nelson et al. |
| 8,137,283 B2 | 3/2012 | Syeda-Mahmood et al. |
| 8,140,164 B2 | 3/2012 | Tehrani et al. |
| 8,185,190 B2 | 5/2012 | Bauer |
| 8,200,336 B2 | 6/2012 | Tehrani |
| 8,233,987 B2 | 7/2012 | Gelfand |
| 8,244,358 B2 | 8/2012 | Tehrani et al. |
| 8,244,359 B2 | 8/2012 | Gelfand |
| 8,265,759 B2 | 9/2012 | Tehrani et al. |
| 8,348,852 B2 | 1/2013 | Bauer et al. |
| 8,409,108 B2 | 4/2013 | Bauer et al. |
| 8,412,323 B2 | 4/2013 | Bauer |
| 8,433,412 B1 | 4/2013 | Westlund |
| 8,548,588 B1 | 10/2013 | Bauer |
| 8,577,448 B2 | 11/2013 | Bauer et al. |
| 8,706,236 B2 | 4/2014 | Ignagni |
| 8,909,341 B2 | 12/2014 | Gelfand |
| 10,335,592 B2 | 7/2019 | Bauer et al. |
| 2002/0103521 A1 | 8/2002 | Swoyer et al. |
| 2002/0188329 A1 | 12/2002 | Struble |
| 2003/0187337 A1 | 10/2003 | Tarassenko et al. |
| 2003/0195571 A1 | 10/2003 | Burnes et al. |
| 2004/0088015 A1 | 5/2004 | Casavant et al. |
| 2004/0127792 A1 | 7/2004 | Siejko et al. |
| 2004/0230105 A1 | 11/2004 | Geva et al. |
| 2005/0027323 A1 | 2/2005 | Mulligan et al. |
| 2005/0043644 A1 | 2/2005 | Stahmann et al. |
| 2005/0065563 A1 | 3/2005 | Scheiner |
| 2005/0080348 A1 | 4/2005 | Stahmann et al. |
| 2005/0085865 A1 | 4/2005 | Tehrani |
| 2005/0085866 A1 | 4/2005 | Tehrani |
| 2005/0085869 A1 | 4/2005 | Tehrani |
| 2005/0090870 A1 | 4/2005 | Hine |
| 2005/0222515 A1 | 10/2005 | Polyshchuk et al. |
| 2006/0079942 A1 | 4/2006 | Deno et al. |
| 2006/0122661 A1 | 6/2006 | Mandell |
| 2006/0122662 A1 | 6/2006 | Tehrani et al. |
| 2006/0155202 A1 | 7/2006 | Arand et al. |
| 2006/0271108 A1 | 11/2006 | Libbus et al. |
| 2007/0021795 A1 | 1/2007 | Tehrani |
| 2007/0038137 A1 | 2/2007 | Arand et al. |
| 2007/0055151 A1 | 3/2007 | Shertukde et al. |
| 2007/0191725 A1 | 8/2007 | Nelson |
| 2008/0021510 A1 | 1/2008 | Mi et al. |
| 2008/0125820 A1 | 5/2008 | Stahmann et al. |
| 2008/0167695 A1 | 7/2008 | Tehrani |
| 2008/0177191 A1 | 7/2008 | Patangay et al. |
| 2008/0188904 A1 | 8/2008 | Tehrani et al. |
| 2008/0215106 A1 | 9/2008 | Lee et al. |
| 2008/0255465 A1 | 10/2008 | Nelson |
| 2008/0287820 A1 | 11/2008 | Ignani et al. |
| 2008/0288010 A1 | 11/2008 | Tehrani |
| 2008/0288015 A1 | 11/2008 | Tehrani et al. |
| 2009/0024176 A1 | 1/2009 | Yun et al. |
| 2009/0048640 A1 | 2/2009 | Bauer |
| 2009/0112107 A1 | 4/2009 | Nelson et al. |
| 2009/0122108 A1 | 5/2009 | Yoshida et al. |
| 2009/0165559 A1 | 7/2009 | Lec |
| 2009/0192561 A1 | 7/2009 | Bauer |
| 2010/0094148 A1 | 4/2010 | Bauer et al. |
| 2010/0094376 A1 | 4/2010 | Penner |
| 2010/0331903 A1 | 12/2010 | Zhang et al. |
| 2011/0015702 A1 | 1/2011 | Ternes et al. |
| 2011/0230932 A1 | 9/2011 | Tehrani |
| 2011/0288609 A1 | 11/2011 | Tehrani et al. |
| 2012/0296388 A1 | 11/2012 | Zhang |
| 2013/0030498 A1 | 1/2013 | Karamanoglu |
| 2013/0289636 A1 | 10/2013 | Karamanoglu et al. |
| 2013/0296973 A1 | 11/2013 | Tehrani et al. |
| 2014/0114371 A1 | 4/2014 | Westlund |
| 2014/0172040 A1 | 6/2014 | Bauer |
| 2016/0022988 A1* | 1/2016 | Thieme .............. A61N 1/36021 607/46 |
| 2017/0143973 A1 | 5/2017 | Tehrani |
| 2017/0312507 A1* | 11/2017 | Bauer .............. A61B 17/00234 |
| 2019/0247656 A1 | 8/2019 | Bauer |
| 2019/0255322 A1 | 8/2019 | Bauer et al. |

FOREIGN PATENT DOCUMENTS

| | | |
|---|---|---|
| JP | 2010537716 A | 12/2010 |
| WO | 2009029172 A1 | 3/2009 |
| WO | 2016033245 A1 | 3/2016 |
| WO | 2017053935 A1 | 3/2017 |

OTHER PUBLICATIONS

Matuschak et al. "Hemodynamic effects of syncrhonous high-frequency jet ventilation during acute hypovolemia." J. of Applied Physiology vol. 61:1 44-53 (Jul. 1986).

(56) References Cited

OTHER PUBLICATIONS

Pang et al. Monitoring respiratory activity in neonates using diaphragmatic electromyograph. Medical and Biological Engineering and Computing, vol. 33, 385-390 (1995).
PCT/US2020/052246. Annex, Partial Int'l Search Report (dated Dec. 16, 2020).
PCT/US2020/052246, Int'l Search Report & Written Opinion (dated Feb. 12, 2021).
PCT/US2020/052246 Written Opinion of the International Preliminary Examining Authority dated Aug. 9, 2021. (10 pages).
PCT/US2020/052246. International Preliminary Reporton Patentability dated Dec. 3, 2021. (37 pages).
Matuschak et al. "Hemodynamic effects of synchronous high-frequency jet ventilation during acute hypovolemia." J Appl Physiol. 61(1): 44-53 (Jul. 1986).
Pinsky et al. "Hemodynamic effects of cardiac cycle-specific increases in intrathoracic pressure." J Appl Physiol. 60(2):604-12 (Feb. 1986).
Pinsky et al. "Augmentation of cardiac function by elevation of intrathoracic pressure." J Appl Physiol. 54(4):950-55 (Apr. 1983).
Pinsky, et al., "Determinants of cardiac augmentation by elevations in intrathoracic pressure." J Appl Physiol. 58(4):1189-98 (May 1985).
Roos, Markus, et al; Improved cardiac performance through pacing-induced diaphragmatic stimulation: a novel electrophysiological approach in heart failure management? European Society of Cardiology. Clinical Research. Pacing and Cardiac Resynchronization Therapy. Europace (2009) 11, 191-199. Lucerne, Switzerland (Dec. 8, 2008).
Zuber, Michel, et al; Detection and Hemodynamic Significance of Cardiac Pacemaker-Induced Phrenic Nerve Stimulation. Deparlment of Cardiology, Kantonsspital, Luzern, Switzerland. 2010 Wiley Periodicals, Inc. Lucerne, Switzerland (Aug. 13, 2009).
Beeler et al. "Improvement of cardiac function with device-based diaphragmatic stimulation in chronic heart failure patients: the randomized, open-label, crossover Epiphrenic II Pilot Trial." European Journal of Heart Failure (2014) 16. pp. 342-349. European Society of Cardiology.
Neuman, "Biopotential Electrodes". The Biomedical Engineering Handbook: Second Edition, Boca Rato CRC Press LLC (2000).

\* cited by examiner

IMPLANTABLE MEDICAL SYSTEMS, DEVICES, AND METHODS FOR AFFECTING CARDIAC FUNCTION THROUGH DIAPHRAGM STIMULATION, AND FOR MONITORING DIAPHRAGMATIC HEALTH

CROSS-REFERENCE TO RELATED APPLICATION(S)

This application claims the benefit of and priority to U.S. Provisional Patent Application Ser. No. 62/906,682, filed Sep. 26, 2019, for "Implantable Medical Systems, Devices and Methods that Affect Pressures Within the Intrathoracic Cavity," the entire disclosure of which is incorporated herein by reference.

TECHNICAL FIELD

The present disclosure relates generally to systems, devices and method for affecting cardiac function, and more particularly, to implantable medical systems, devices and methods that affect pressures within the intrathoracic cavity through diaphragm stimulation. The present disclosure also relates generally to systems, devices and method for monitoring patient health, and more particularly, to implantable medical systems, devices and methods that monitor electromyography (EMG) electrical activity of the diaphragm to assess patient health.

BACKGROUND

The diaphragm is a dome shaped skeletal muscle structure separating the thoracic and abdominal cavities. It is the major muscular organ responsible for mechanical respiratory motion by deflecting downwards upon contraction during inspiration. The phrenic nerve innervates the diaphragm and acts as the primary method of nervous excitation to signal contraction. The external and internal intercostal muscles also elevate the ribs increasing the anterior-posterior diameter of the thoracic cavity. During inspiration, the movement of the diaphragm results in expansion and negative pressure within the thoracic cavity as the diaphragm and intercostal muscles increase the size of the thorax. The expanding thorax causes the intrathoracic pressure to decrease below atmospheric pressure and air moves into the lungs. During exhalation, the inspiratory muscles relax, and the elastic recoil of the lung tissues, combined with a rise in intrathoracic pressure, causes air to move out of the lungs.

Changes in intrathoracic pressure from diaphragmatic contraction and thoracic expansion may be transmitted to the intrathoracic structures namely the heart, pericardium, great arteries and veins. Spontaneous inspiration produces a negative pleural pressure affecting cardiovascular performance including atrial filling (preload) and resistance to ventricular emptying (afterload). This affect can be observed in cardiovascular hemodynamic parameters during normal function when diaphragmatic contractions are of sufficient duration, intensity and expansiveness to cause inspiration, and used in clinical practice during Vasalva and Mueller maneuvers where patients forcefully inspire or expire using diaphragmatic muscles against a closed glottis causing a rapid change in thoracic pressures. These maneuvers result in pronounced rapid acute changes to intrathoracic pressure, which changes in turn alter pressure gradients associated with the cardiac chambers and vessels to affect cardiac functions, including cardiac filling and output.

The effects of intrathoracic pressure on cardiac systemic performance are complex. Hiccups, which result from rapid partial diaphragmatic contractions causing rapid decreases to intrathoracic pressure, have been previously used to characterize their effects of cardiac and systemic performance. Studies of both animal and human subjects demonstrated changes to hemodynamic parameters including overall ventricular diastolic and systolic pressures, cardiac output and changes to systemic measures including aortic distention and vascular resistance. These studies also demonstrated that rapid intrathoracic pressure effect changes are extremely sensitive to timing relative to the cardiac cycle, with different observed if the hiccups occur during ventricular diastolic, systole, or during the diastole-systole transition.

BRIEF DESCRIPTION OF THE DRAWINGS

Various aspects of systems, devices and methods that affect pressures within the intrathoracic cavity through diaphragmatic stimulation will now be presented in the detailed description by way of example, and not by way of limitation, referring to the accompanying drawings, wherein.

SUMMARY

Figure 1:
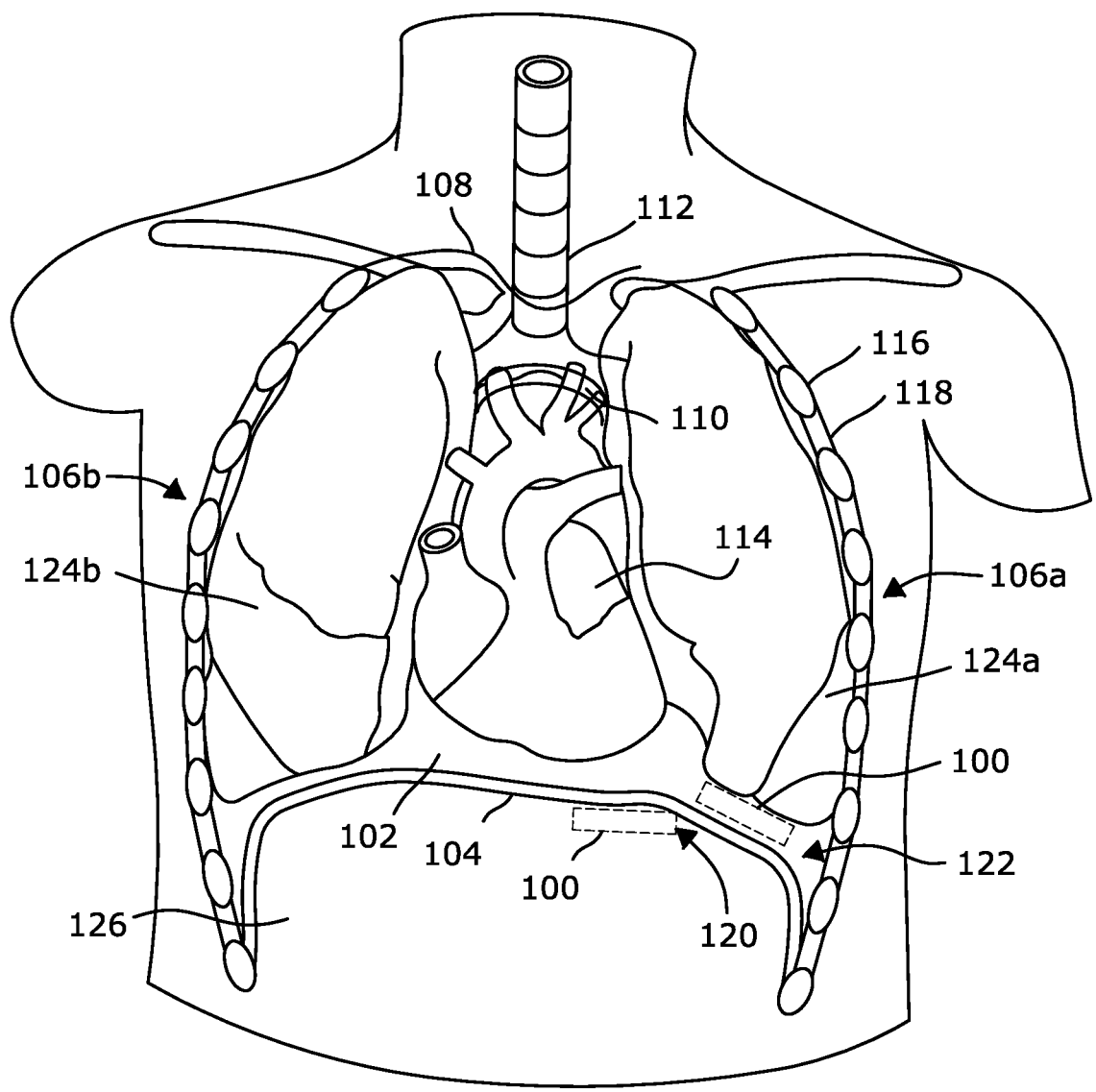
FIG. 1 is an illustration of an asymptomatic diaphragm stimulation (ADS) therapy delivery mechanism shown in two alternate locations relative to the thoracic cavity of a patient.

Devices, systems, and methods disclosed herein provide various forms of asymptomatic diaphragmatic stimulation (ADS) therapy that affect pressures within the intrathoracic cavity to improve cardiac function. These forms of ADS therapy include: 1) dual-pulse ADS therapy, during which a first ADS pulse is delivered during a diastolic phase of a cardiac cycle and a second ADS pulse is delivered during a systolic phase, 2) paired-pulse ADS therapy, during which a first ADS pulse is delivered, closely followed by a second ADS pulse, with the second ADS pulse functioning to extend or enhance a phase of a transient, partial contraction of the diaphragm, and 3) multiple-pulse ADS therapy, during which a stream of ADS pulses is delivered, wherein the time between pulses is based on heart rate.

In one aspect of the disclosure, an apparatus for providing dual-pulse ADS therapy to affect pressure in an intrathoracic cavity of a patient includes one or more electrodes configured for placement on or near a diaphragm, and a controller coupled to the one or more electrodes. The controller is configured to deliver a diastolic stimulation pulse to the diaphragm of the patient during a diastolic phase of a cardiac cycle of the patient, and to deliver a systolic stimulation pulse to the diaphragm during a systolic phase of the cardiac cycle. The pulses are delivered such that each of the diastolic stimulation pulse and the systolic stimulation pulse results in an asymptomatic, transient, partial contraction of the diaphragm. To this end, respective pulse delivery may be defined by stimulation parameters, including an offset period or delay period, that time the delivery of the respective pulses to produce separate asymptomatic, transient, partial contractions of the diaphragm.

In one aspect of the disclosure, a method of providing dual-pulse ADS therapy to affect pressure in an intrathoracic cavity of a patient includes delivering a diastolic stimulation pulse to a diaphragm of the patient during a diastolic phase of a cardiac cycle of the patient, and delivering a systolic stimulation pulse to the diaphragm during a systolic phase of the cardiac cycle. The pulses are delivered such that each of the diastolic stimulation pulse and the systolic stimulation pulse results in an asymptomatic, transient, partial contraction of the diaphragm. To this end, respective pulse delivery may be defined by stimulation parameters, including an offset period or delay period, that time the delivery of the respective pulses to produce separate asymptomatic, transient, partial contractions of the diaphragm.

In one aspect of the disclosure, an apparatus for providing paired-pulse ADS therapy to affect pressure in an intrathoracic cavity of a patient includes one or more electrodes configured for placement on or near a diaphragm, and a controller coupled to the one or more electrodes. The controller is configured to deliver a first stimulation pulse to the diaphragm of the patient, and to deliver a second stimulation pulse to the diaphragm while the diaphragm is still in motion or contracting from the first stimulation pulse. The first stimulation pulse is configured to induce a transient, partial contraction of the diaphragm comprising a caudal phase corresponding to a time during which a portion of the diaphragm is moving in a caudal direction, followed by a cranial phase corresponding to a time during which the portion of the diaphragm is moving in a cranial direction. The second stimulation pulse is configured to extend a duration of one of the caudal phase or the cranial phase. To this end, the second stimulation pulse may be defined by stimulation parameters, including an offset period or delay period, that time the delivery of the second pulse to extend the duration of one of the caudal phase or the cranial phase.

In one aspect of the disclosure, a method of providing paired-pulse ADS therapy to affect pressure in an intrathoracic cavity of a patient includes delivering a first stimulation pulse to a diaphragm of the patient, and delivering a second stimulation pulse to the diaphragm while the diaphragm is still in motion or contracting from the first stimulation pulse. The first stimulation pulse induces a transient, partial contraction of the diaphragm comprising a caudal phase corresponding to a time during which a portion of the diaphragm is moving in a caudal direction, followed by a cranial phase corresponding to a time during which the portion of the diaphragm is moving in a cranial direction. The second stimulation pulse extends a duration of one of the caudal phase or the cranial phase. To this end, the second stimulation pulse may be defined by stimulation parameters, including an offset period or delay period, that time the delivery of the second pulse to extend the duration of one of the caudal phase or the cranial phase.

In one aspect of the disclosure, an apparatus for providing multiple-pulse ADS therapy to affect pressure in an intrathoracic cavity of a patient includes one or more electrodes configured for placement on or near a diaphragm, and a controller coupled to the one or more electrodes. The controller is configured to deliver a plurality of stimulation pulses to the diaphragm of the patient during a cardiac cycle of the patient. Each of the plurality of stimulation pulses results in a corresponding transient, partial contraction of the diaphragm comprising a caudal phase corresponding to a time during which a portion of the diaphragm is moving in a caudal direction, followed by a cranial phase corresponding to a time during which the portion of the diaphragm is moving in a cranial direction. To this end, the timing between successive stimulation pulses is based on heart rate and the duration of transient, partial contractions of the diaphragm, whereby the timing between pulses allows for each pulse to produce a complete and separate transient, partial contraction of the diaphragm.

In one aspect of the disclosure, a method of providing multiple-pulse ADS therapy to affect pressure in an intrathoracic cavity of a patient includes delivering a plurality of stimulation pulses to a diaphragm of the patient during a cardiac cycle of the patient, wherein each of the plurality of stimulation pulses results in a corresponding transient, partial contraction of the diaphragm comprising a caudal phase corresponding to a time during which a portion of the diaphragm is moving in a caudal direction, followed by a cranial phase corresponding to a time during which the portion of the diaphragm is moving in a cranial direction. To this end, the timing between successive stimulation pulses is based on heart rate and the duration of transient, partial contractions of the diaphragm, whereby the timing between successive stimulation pulses allows for each pulse to produce a complete and separate transient, partial contraction of the diaphragm.

Devices, systems and methods disclosed herein also monitor electromyography (EMG) activity of the diaphragm relative to baseline EMG activity to assess the health of a diaphragm subject to ADS therapy and to adjust ADS therapy parameters or sensing parameters.

In one aspect of the disclosure, an apparatus for affecting pressure in an intrathoracic cavity of a patient through delivery of ADS includes one or more electrodes configured for placement on or near a diaphragm, and a controller coupled to the one or more electrodes. The controller is configured to deliver ADS therapy to the patient over a period of time, where the ADS therapy comprises ADS pulses defined by a one or more stimulation parameters. The controller is also configured to periodically sense over the period of time, EMG electrical activity produced by one or more skeletal muscles of the diaphragm in accordance with one or more sensing parameters, and to determine if the EMG electrical activity satisfies a criterion relative to baseline EMG electrical activity of the patient that is sensed prior to ADS therapy activation. The controller is further configured to adjust at least one of the one or more stimulation parameters and the one or more sensing parameters if the criterion is not satisfied for purposes of improving ADS therapy.

In one aspect of the disclosure, a method of modifying sensing and/or stimulation parameters for an apparatus that affects pressure in an intrathoracic cavity of a patient through delivery of ADS therapy includes delivering ADS therapy to the patient over a period of time. The ADS therapy comprises ADS pulses defined by a one or more stimulation parameters. The method also includes periodically sensing over the period of time, EMG electrical activity produced by one or more skeletal muscles of a diaphragm in accordance with one or more sensing parameters, and determining if the sensed EMG electrical activity satisfies a criterion relative to baseline EMG electrical activity of the patient that is sensed prior to ADS therapy activation. The method further includes adjusting at least one of the one or more stimulation parameters and the one or more sensing parameters if the criterion is not satisfied in order to improve ADS therapy.

In one aspect of the disclosure, an apparatus for monitoring the health of a patient includes one or more electrodes configured for placement on or near a diaphragm, and a controller coupled to the one or more electrodes. The controller is configured to periodically sense over a period of time, EMG electrical activity produced by one or more skeletal muscles of the diaphragm in accordance with one or more sensing parameters, and determine if the sensed EMG electrical activity satisfies a criterion relative to baseline EMG electrical activity of the patient.

In one aspect of the disclosure, a method of monitoring the health of a patient includes periodically sensing over a period of time, EMG electrical activity produced by one or more skeletal muscles of a diaphragm in accordance with one or more sensing parameters. The method also includes determining if the sensed EMG electrical activity satisfies a criterion relative to baseline EMG electrical activity of the patient.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

DETAILED DESCRIPTION

Disclosed herein are implantable medical devices, systems and methods that provide various forms of asymptomatic diaphragmatic stimulation (ADS) therapy that affects pressures within the intrathoracic cavity. In one form of ADS therapy, referred to herein as dual-pulse ADS therapy, a first ADS pulse is delivered during a diastolic phase of a cardiac cycle and a second ADS pulse is delivered during a systolic phase. In another form of ADS therapy, referred to herein as paired-pulse ADS therapy, a first ADS pulse is delivered, closely followed by a second ADS pulse, with the second ADS pulse functioning to extend or enhance a transient, partial contraction of the diaphragm in a particular direction. In another form of ADS therapy, referred to herein as multiple-pulse ADS therapy, a continuous stream of ADS pulses are delivered, wherein the time between pulses is based on heart rate.

Also disclosed are implantable medical devices, systems and methods that assess the health of a diaphragm that is subject to ADS therapy and the heart failure status of a patient that is subject to ADS therapy. These systems, devices, and methods monitor electromyography (EMG) activity of the diaphragm relative to baseline activity to determine patient status and to adjust ADS therapy parameters, including stimulation parameters and/or sensing parameters.

Electrical stimulation to the diaphragm induces transient, partial, asymptomatic diaphragmatic contractions, which in turn induces changes in intrathoracic pressures. Appropriately timed and configured diaphragmatic stimulation may improve cardiovascular performance and cardiac function, to thereby manage heart failure. For example, diaphragmatic stimulation synchronized with, or otherwise timed to an occurrence of a cyclic cardiac event, such as ventricular systole may accelerate negative intrathoracic cavity pressure (suction) during left ventricular filling to increase filling volume, and then accelerate positive intrathoracic cavity pressure (compression) to augment systolic contractile forces generated by the left ventricle.

Because the management of heart failure is complex and physicians need to optimize numerous various and interdependent physiologic effects between the heart and vessels, an objective of the therapy disclosed herein is to utilize evoked diaphragmatic contractions to optimize the operating intrathoracic pressure conditions on the heart and vessels for improving the patient's overall condition. These include: the blood volume to one or more chambers of the cardiovascular system within the thoracic cavity, end diastolic pressure (preload) that causes changes to systolic output (starling), that mediates intracardiac blood flow (diastolic coronary perfusion) and operating mechanics (efficiency), or for decreasing the compliance of the vessels responsible for cardiac filling (vena cava and right atrium) or for altering the compliance of cardiac vessels to better match the operational ability of the heart (impedance matching or optimization). These indirect physiologic mechanisms will augment the direct physiologic mechanism of mechanically augmenting the mechanical forces of the heart and decreasing the vascular resistance to cardiac output.

Asymptomatic Diaphragmatic Stimulation

FIG. 1 is a schematic illustration of an asymptomatic diaphragmatic stimulation (ADS) therapy delivery mechanism 100 implanted in the region of a patient's thoracic cavity 102 on or near the patient's diaphragm 104. The ADS therapy delivery mechanism 100 is configured to deliver stimulation pulses to the diaphragm 104 in accordance with a diaphragm stimulation program. The ADS therapy delivery mechanism 100 may be one or more electrodes configured to be positioned on or near a diaphragm. Although illustrated in FIG. 1 generically, the ADS therapy delivery mechanism 100 may be:

1) A standalone implantable medical device (IMD) in the form of either: a) a single-piece, unitary structure having no removable component parts and that houses electronics and carries the ADS therapy delivery mechanism, or b) a multi-piece IMD having a can that houses electronics and a sub-structure, e.g., a lead, that carries the ADS therapy delivery mechanism. The sub-structure may be a lead that electrically and mechanically couples to the can, or may be a separate, unconnected module that wirelessly communicates with the can.

2) Alternatively, the ADS therapy delivery mechanism 100 may be a part of an IMD that provides other therapy, such as cardiac rhythm management (CRM) device in the form of a pacemaker, cardiac resynchronization therapy device, or defibrillator. The part may be, for example, a lead, that carries the ADS therapy delivery mechanism and electrically and mechanically couples to the can of the CRM device, or may be a separate, unconnected module that wirelessly communicates with the can of the CRM device.

3) Or the ADS therapy delivery mechanism 100 may be a part of a medical system that includes one or more implantable devices operating in a master/slave arrangement together with an external device.

Continuing with FIG. 1, the ADS therapy delivery mechanism 100 may be placed, through conventional laparoscopy, at a selected surface region of the diaphragm 104 on the inferior side of the diaphragm at a location referred to as an inferior implant location 120. Alternatively, the ADS therapy delivery mechanism 100 may be placed, through conventional thoracotomy, at a selected surface region of the diaphragm 104 on the superior side of diaphragm 104 at a location referred to as a superior implant location 122. For example, the ADS therapy delivery mechanism 100 may be positioned between the superior surface of diaphragm 104 and the underside of the patient's left lung 124a.

The thoracic cavity 102, also referred to as the intrathoracic cavity and the mediastinum, is a hermetically sealed cavity formed by various connected structures. These structures include the diaphragm 104, the thoracic sidewalls 106a, 106b, and layered walls 108, 110, near the trachea 112 and the heart 114.

The diaphragm 104 is a dome-shaped skeletal muscle structure located below the lungs 124a, 124b that separates the thoracic cavity 102 from the abdominal cavity 126. The diaphragm 104 defines the lower end of the thoracic cavity 102 and is the major muscular organ responsible for mechanical respiratory motion. The thoracic sidewalls 106a, 106b are formed of ribs 116 and membrane 118 filing the space between the ribs, and define the thoracic sidewalls 106a, 106b of the thoracic cavity 102. The layered walls 108, 110 are formed of various membranes and vessels which lay over each other to form a seal at the top of the thoracic cavity 102.

Mechanical respiratory motion includes an inspiration or inhalation phase and an expiration or exhalation phase. As previously mentioned, the diaphragm 104 is the major muscular organ responsible for mechanical respiratory motion. The phrenic nerve (not shown) innervates the diaphragm 104 and sends signals to the diaphragm to control inspiration and expiration. These signals act as the primary mechanism for initiating contraction of the diaphragm through nervous excitation. Since nervous endings responsible for pain sensation are absent within the diaphragm, a confine of therapy outputs are those which provide the desired hemodynamic effects to the cardiovascular system while simultaneously minimizing the likelihood of field stimulation of pain nerves contained within other nearby innervated thoracic cavity musculature.

Figure 2A:
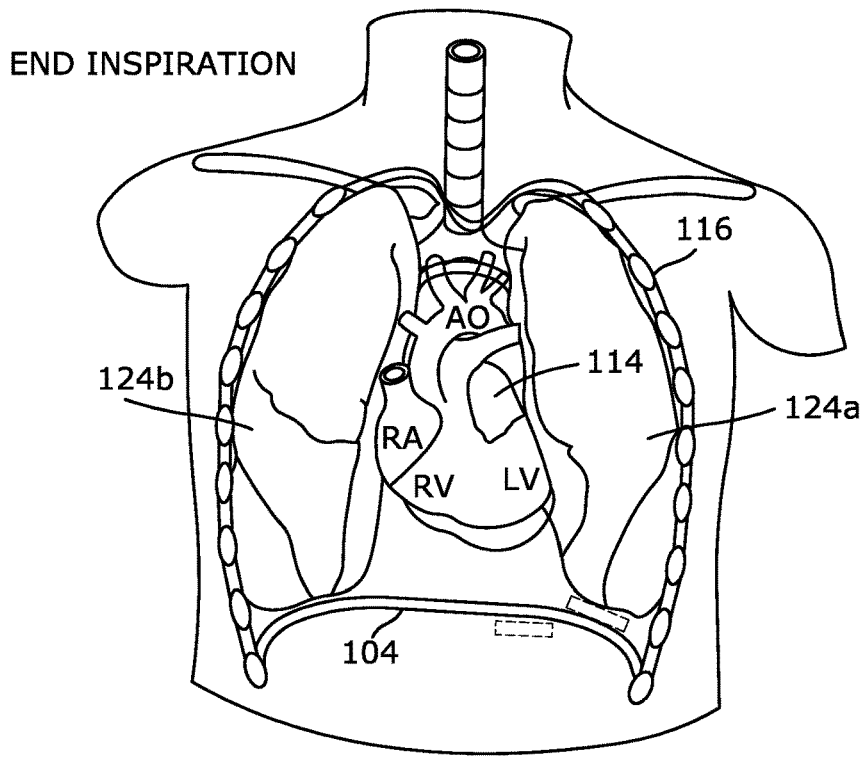
FIG. 2A is an illustration of the thoracic cavity at end inspiration.

FIG. 2A is an illustration of the thoracic cavity at end inspiration. During inspiration, the diaphragm 104 contracts, e.g., flattens out, and deflects downward, in a direction away from the lungs 124a, 124b. Concurrent with downward deflection of the diaphragm during inspiration, the external and internal intercostal muscles around the lungs 124a, 124b elevate the ribs 116, thereby increasing the anterior-posterior diameter of the thoracic cavity 102. During inspiration, the movement of the diaphragm 104 results in expansion and negative pressure within the thoracic cavity 102 as the diaphragm and intercostal muscles increase the size of the thorax. The expanding thorax causes the pressure within the open space of thoracic cavity 102, i.e., the intrathoracic pressure, to decrease below atmospheric pressure. The pressure decrease causes external air to move into the lungs 124a, 124b.

Figure 2B:
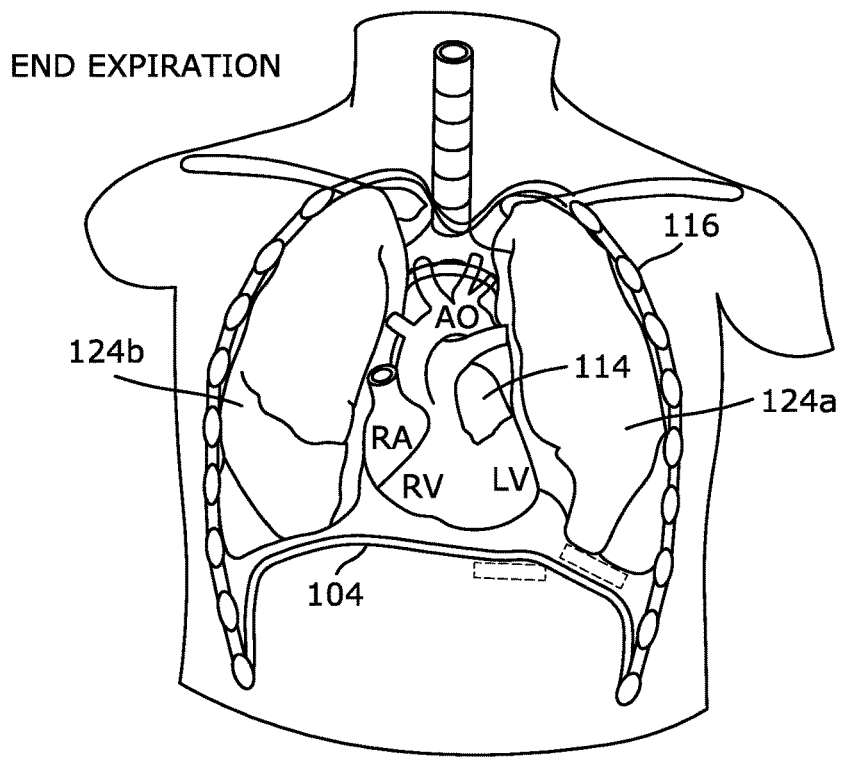
FIG. 2B is an illustration of the thoracic cavity at end expiration.

FIG. 2B is an illustration of the thoracic cavity at end expiration. During expiration, the diaphragm 104 expands, e.g., assumes a dome shape, and deflects upward, in the direction of the lungs 124a, 124b. During expiration, the diaphragm 104, together with the external and internal intercostal muscles around the lungs 124a, 124b relax. The diaphragm 104 expands, e.g., resumes a dome shape, and the ribs 116 de-elevate, thereby reducing the anterior-posterior diameter of the thoracic cavity 102, and causing the intrathoracic pressure to increase above atmospheric pressure. The increase in intrathoracic pressure in combination with the elastic recoil of lung tissues, causes air to move out of the lungs.

Changes in the pressure within the open space of the thoracic cavity 102, i.e., the intrathoracic pressure, due to diaphragm contraction and thoracic cavity expansion, and diaphragm expansion and thoracic cavity contraction bring about changes in other pressures within the intrathoracic cavity, including pressures associated with intrathoracic structures like the heart 114, pericardium, great arteries and veins. For example, changes in cardiovascular pressures, such as right atrial (RA) pressure, right ventricular (RV) pressure, left ventricular (LV) pressure, and aortic (AO) pressure result from changes in intrathoracic pressure.

In accordance with presently disclosed embodiments, intrathoracic pressure is manipulated through controlled delivery of diaphragmatic stimulation through an ADS therapy delivery mechanism, to bring about desirable changes in other pressures within the intrathoracic cavity to improve cardiac function. Through delivery of appropriately timed stimulation therapy to the diaphragm, transient, asymptomatic, partial contractions of the diaphragm are induced in synchrony or near synchrony with one or more cardiac events to delivery ADS therapy are specified portions of a cardiac cycle. Timing the occurrences of these transient, asymptomatic, partial contractions relative to cardiac events results in changes in intrathoracic pressure, which in turn, increases and/or decreases pressures associated with the heart, pericardium, great arteries and veins to thereby improve hemodynamic function of the heart.

Figure 2C:
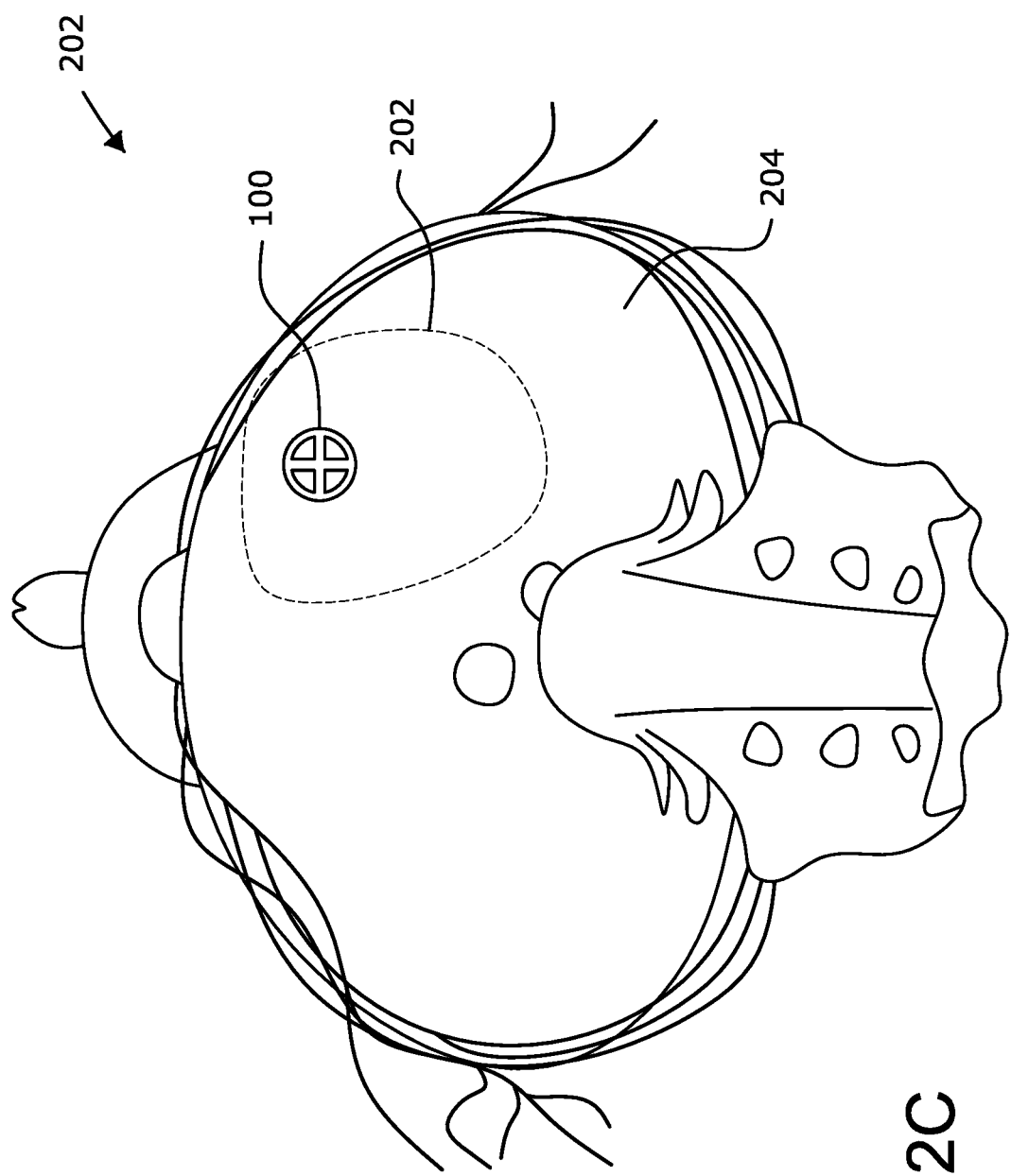
FIG. 2C is an illustration of a diaphragm and sacrum viewed from the inferior side of the diaphragm and in the caudal direction.

As used herein, a "transient" contraction of the diaphragm is a short, twitching, caudal followed by cranial motion of the diaphragm that lasts in range of 60 to 180 msec., and is typically about 100 msec. A "partial" contraction of the diaphragm is the part or region of the diaphragm (less than the entirety of the diaphragm) that exhibits a "transient" contraction. For example, with reference to FIG. 2C, a diaphragm stimulation pulse delivered through an ADS therapy delivery mechanism 100 placed on the left hemisphere of a diaphragm 204 will result in contraction of a portion 202 or part of the left hemisphere that is less than the entirety of the left hemisphere.

Signals indicative of pressures within the intrathoracic cavity, including intrathoracic pressure itself, and other pressures, such as cardiovascular pressures, may be monitored and used as a feedback mechanism to adjust ADS therapy. To this end, one or more parameters that define ADS therapy may be changed to obtain a desired increase and/or decrease in pressures associated with the heart, pericardium, great arteries and veins. For example, in the case of electrical stimulation therapy, one or more of the timing at which an electrical stimulation pulse is delivered, a pulse waveform type, a pulse amplitude, a pulse duration, and a pulse polarity, may be adjusted or changed.

Other signals indicative of pressures within the intrathoracic cavity, such as heart sounds, may also be monitored and used as a feedback mechanism to adjust ADS therapy. For example, heart sound signals may be used to determine timings between occurrences of cardiac events. One or more parameters that define ADS therapy may be changed to obtain a desired increase and/or decrease in these timings.

Other signals not related to pressures within the intrathoracic cavity may also be monitored and used as a feedback mechanism to adjust ADS therapy and optimize therapy. For example, signals related to the hemodynamic effect of change, i.e. change in pulse transit time, may be monitored. In one configuration, the time from the R wave (or other ECG fiducials) to the peak or max first derivative of the SpO2 (plethysmograph) signal may be measured for various fixed timing delays between the R wave (or other ECG fiducials) and the ADS pulse delivered to the diaphragm. The results are trended and the properties of that trend, i.e. minima and maxima are determined either algorithmically and/or visually by the clinician. The best setting would be the ADS delay setting which is associated with the longest time from the R wave (or other ECG fiducials) to the max first derivative of the SpO2 (plethysmograph) signal as this reflects the best cardio-vascular impedance match and most optimal decrease in afterload for that patient. In another configuration, the time from the Q point (or other ECG fiducials) to the mitral valve component of the first heart sound (S1) is assessed for each programmed ADS delay setting, and the setting associated with the shortest Q to S1 is then determined to be the best setting for the patient as it reflects the best setting at which the heart systolic function is most efficient.

Devices and Systems for ADS Therapy

As previously described, an ADS therapy delivery mechanism 100 may be: 1) a part of a single-piece, or multi-piece standalone IMD that delivers only diaphragmatic stimulation therapy, 2) a part of a multi-therapy IMD that provides other therapy, such as CRM therapy, in addition to diaphragmatic stimulation therapy, or 3) a part of an medical system that monitors, diagnoses and treats various patient conditions.

Standalone, Multi-Piece Implantable Medical Device

Figure 3A:
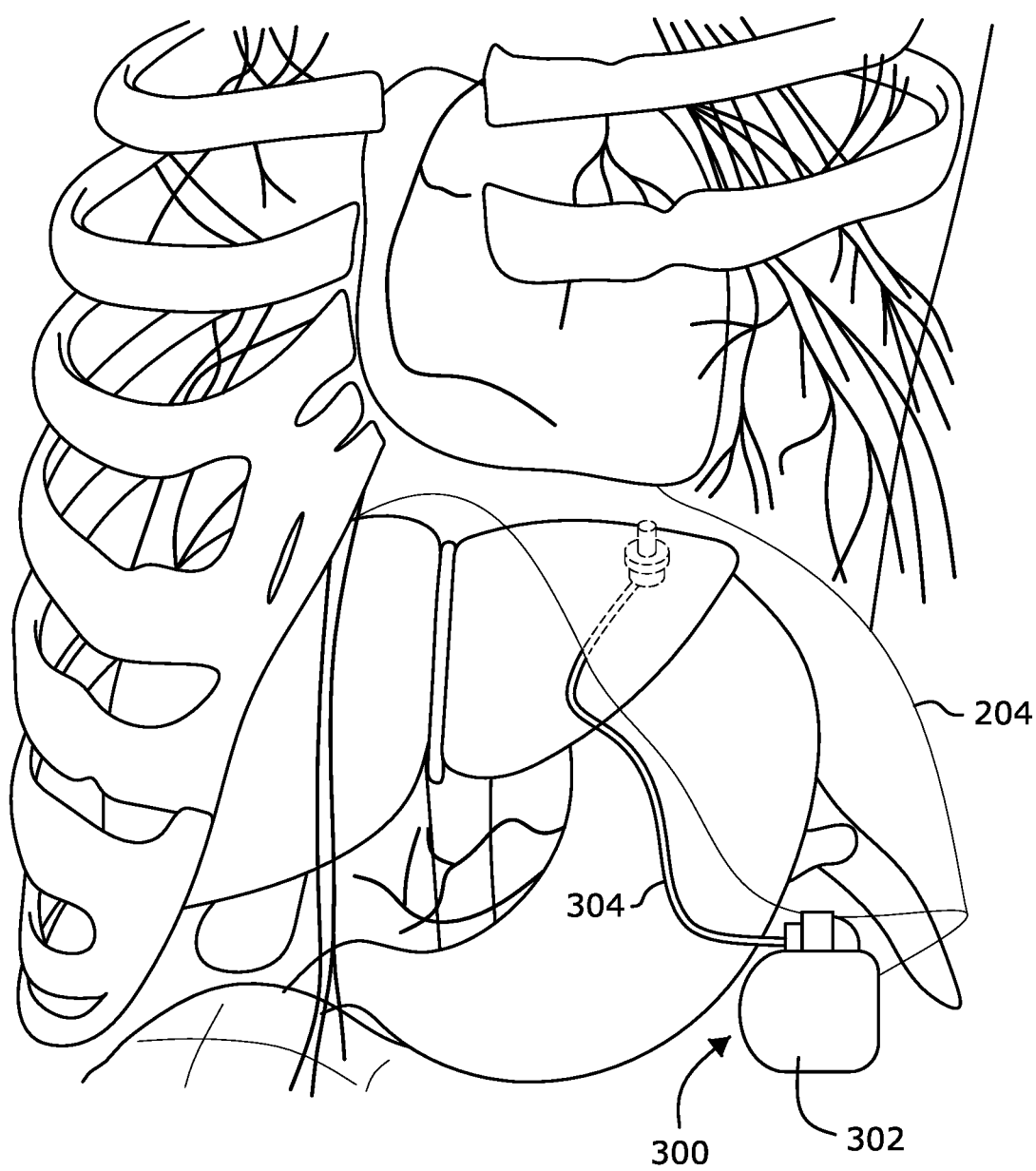
FIG. 3A is an illustration of a multi-piece embodiment of an implantable medical device for providing ADS therapy implanted on the inferior side of the diaphragm.
Figure 3B:
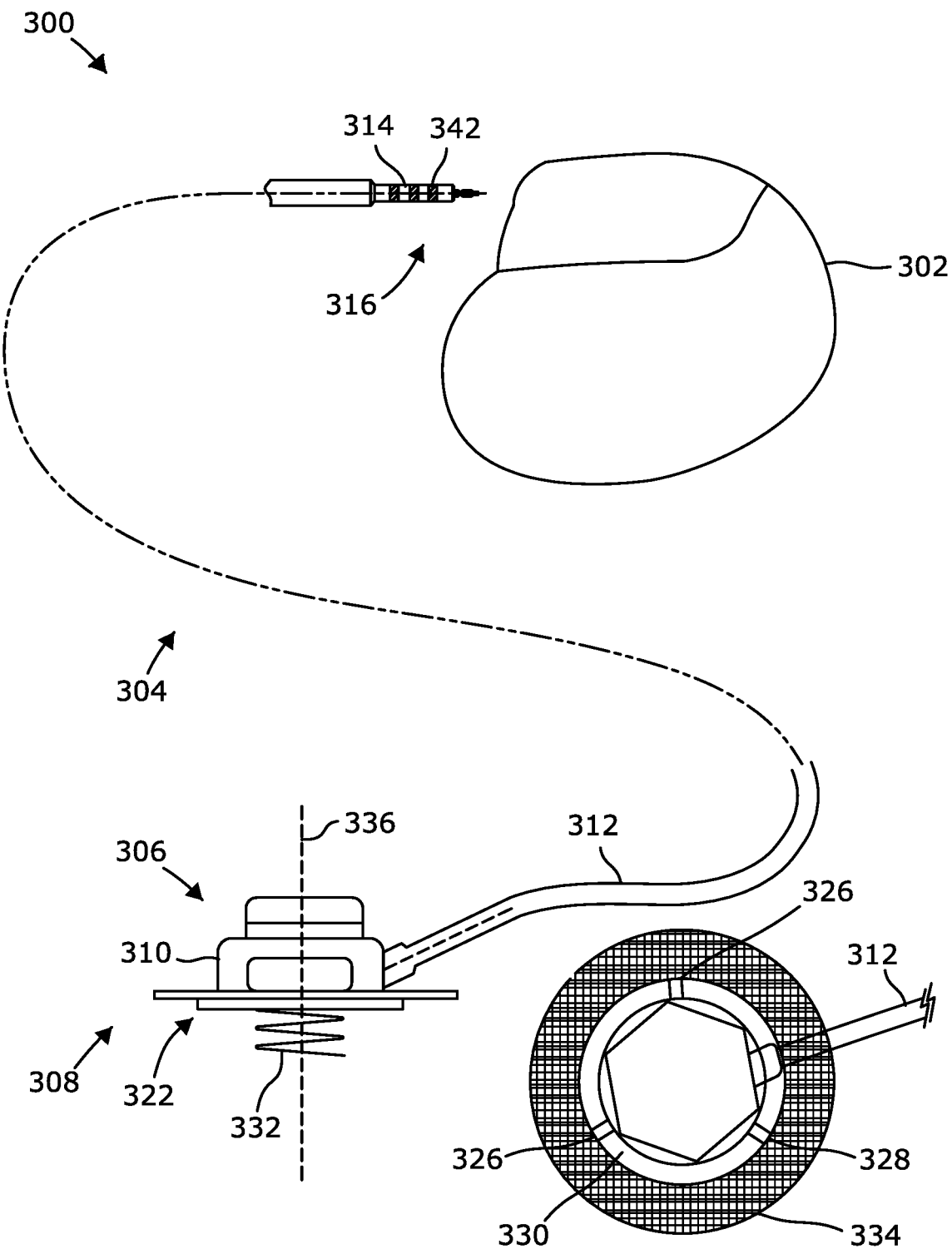
FIG. 3B is an illustration of the implantable medical device of FIG. 3A.

With reference to FIGS. 3A and 3B, a standalone, multi-piece IMD 300 that delivers only ADS therapy includes a can or housing 302 that houses electronics and a substructure 304, e.g., a lead, that carries an ADS therapy delivery mechanism comprising a ring electrode 330 and a helix electrode 332. The lead 304 is configured for implant on a surface of a biological membrane forming part of a hermetically sealed biological cavity. For example, the biological membrane may be a diaphragm 204 and the hermetically sealed biological cavity may be the thoracic cavity, as described above referring to FIG. 1. In FIG. 3A the IMD 300 is located on the inferior side of the diaphragm 204.

The lead 304 includes a sensor assembly 306 at a distal end 308 of the lead. The sensor assembly 306 includes a housing 310, which may be cylindrical in shape, that is electrically coupled to a lead body 312 that extends from the distal end 308 of the lead to a connector 314 at the proximal end 316 of the lead. The sensor assembly 306 further includes a sensor structure 322. Conductive wires from the lead body 312 pass through the housing 310 to connect with sensors.

The sensor structure 322 includes one or more sensors 326, 328. The sensors may be, for example, electrodes 326 for sensing cardiac electrical activity, or a motion sensor 328, e.g. an acoustic transducer for sensing heart sounds, or an accelerometer for sensing mechanical motion of the heart and/or the diaphragm. In the case of electrodes 326, the electrodes may be flat surface electrodes or ring electrodes. In one configuration, the sensor structure 322 includes a ring 330 having a circumference and one or more electrodes 326 spaced apart around the circumference of the ring, and possibility one or more motion sensors 328. In another configuration, the entirety of the ring 330 may be a single electrode and another electrode may be located within the ring.

The sensor assembly 306 further includes one or more fixation structures associated with the housing 310 for securing the sensor assembly to a biological membrane. In one embodiment, the fixation structure may be a projecting structure 332 that extends away from the housing 310 in a direction along a central axis 336 of the cylindrical housing. For example, the projecting structure 332 may be in the form of a helix located in the center of the ring 330 that forms part of the sensor structure 322. The projecting structure 332 may be formed of an electrically conductive material and may function both as a fixation device for securing the sensor assembly 306 to a biological membrane, e.g., a diaphragm, and as an additional electrode for the sensor assembly.

In another embodiment, the fixation structure may be an extension member 334 that extends beyond the outer circumference of the housing 310. To this end, the extension member 334 has a maximum dimension, e.g., diameter, that is greater than a maximum dimension, e.g., diameter, of the housing 310. The extension member 334 may be in the form of a ring that surrounds the sensor assembly 306. As described further below, the extension member 334 may be configured in various ways to attach to the surface of the biological membrane to secure the sensor assembly 306 in place.

In yet another embodiment, the fixation structure may include both a projecting structure 332 and an extension member 334. In this embodiment, the extension member 334 surrounds the projecting structure 332 and is configured to form a seal between itself and the biological membrane, which seal surrounds the projecting structure. The extension member 334 is a generally planar structure that increases the overall size of the contact surface area of the sensor assembly 306 around the area where the projecting structure 332 extends into the diaphragm. The contact surface area corresponds to the surface area of the sensor assembly 306 that will contact the diaphragm. Upon implant of the sensor assembly 306, and over time, the diaphragm may react to the presence of the sensor assembly and form an adhesive bond with the sensor assembly.

The extension member 334 may include other features that help secure the sensor assembly 306 in place and/or help expedite the formation of a seal with the surface of the diaphragm. For example, the extension member 334 may include an adhesive that both secures the sensor assembly 306 in place and forms a hermetic seal with the surface of the diaphragm around the area where the projecting structure 332 extends into the diaphragm.

In another configuration, the extension member 334 may be formed of a material configured to secure the sensor assembly 306 in place and to expedite the formation of a seal with the surface of the diaphragm around the area where the projecting structure 332 extends into the diaphragm. For example, the extension member 334 may be a mesh material formed of polyester textile fiber, such as Dacron, or other fabric. Upon contact between the mesh structure 334 and the diaphragm, the mesh structure absorbs biological fluids on the surface of the diaphragm, clings to the diaphragm, and forms a seal between itself and the diaphragm.

The connector 314 of the lead includes a number of contacts 342 corresponding to the number of electrodes 326 and sensors 328 associated with the sensor assembly 306. The lead body 312 includes conductors that electrically connect the contacts 342 at the proximal end 316 with the sensors 326, 328 of the sensor assembly 306.

Standalone, Single-Piece Implantable Medical Device

Figure 4A:
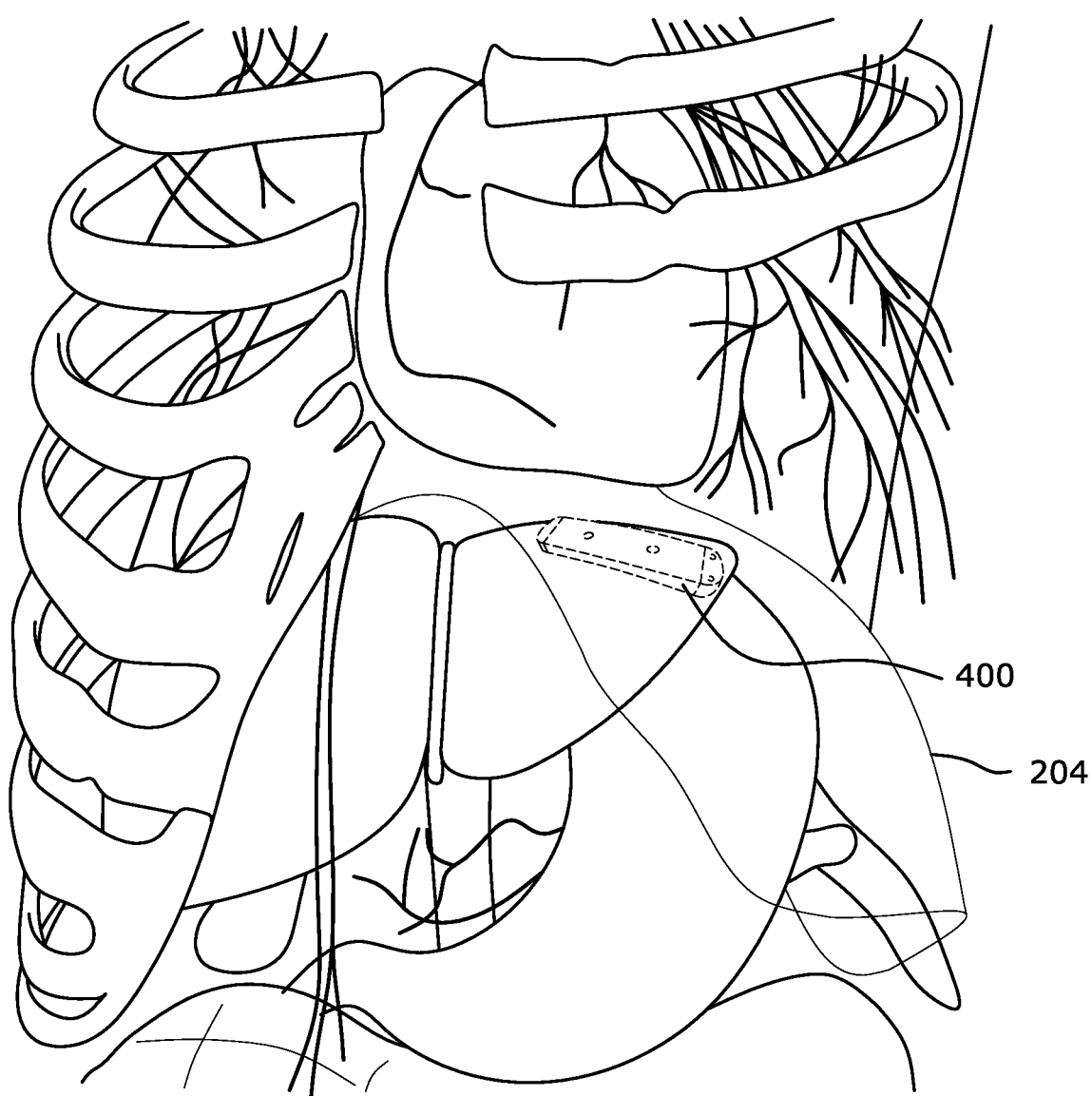
FIG. 4A is an illustration of a single-piece embodiment of an implantable medical device for providing ADS therapy implanted on the inferior side of the diaphragm.
Figure 4B:
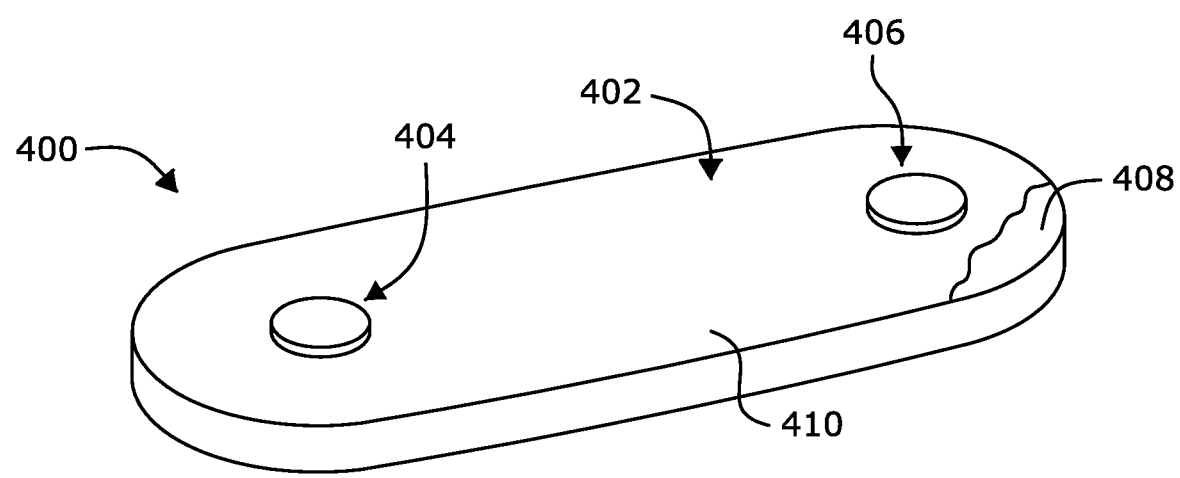
FIG. 4B is an illustration of the implantable medical device of FIG. 4A.

With reference to FIGS. 4A and 4B, a standalone, single-piece IMD 400 that delivers only ADS therapy includes a housing 402 with at least two electrodes 404, 406 closely associated with a surface of the housing. The single-piece IMD 400 is configured for implant on a surface of a biological membrane forming part of a hermetically sealed biological cavity. For example, the biological membrane may be a diaphragm 204 and the hermetically sealed biological cavity may be the thoracic cavity, as described above referring to FIG. 1. In FIG. 4A the IMD 400 is located on the inferior side of the diaphragm 204.

While the IMD 400 illustrated in FIG. 4B is formed is the shape of an elongated disk, the IMD may have other form factors, including for example, a tube. The leadless IMD 400 may have a length of about 1.25-inches, a width of about 0.5-inches, and a thickness of about 0.125-inches. The two electrodes 404, 406 are spaced apart by about 1-inch and are located on a surface 408 of the housing. A non-electrically-conductive, biocompatible mesh 410 may be affixed to the surface 408 to facilitate anatomical bonding of the IMD 400 to the surface region of the diaphragm 204.

Multi-Therapy Implantable Medical Device

Figure 5A:
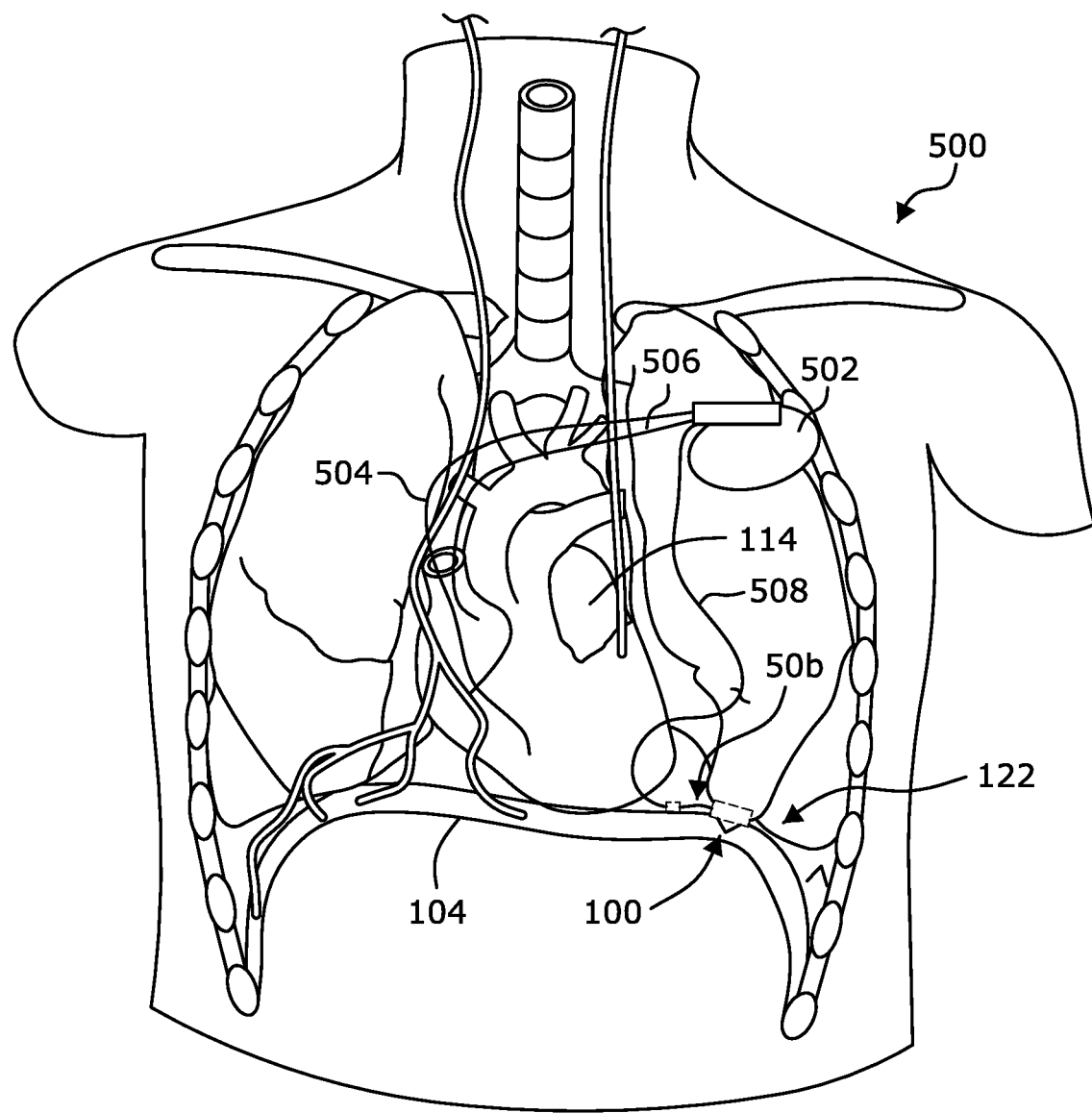
FIG. 5A is an illustration of an implantable medical device that provides ADS therapy and another therapy, such as cardiac rhythm management (CRM) therapy.
Figure 5B:
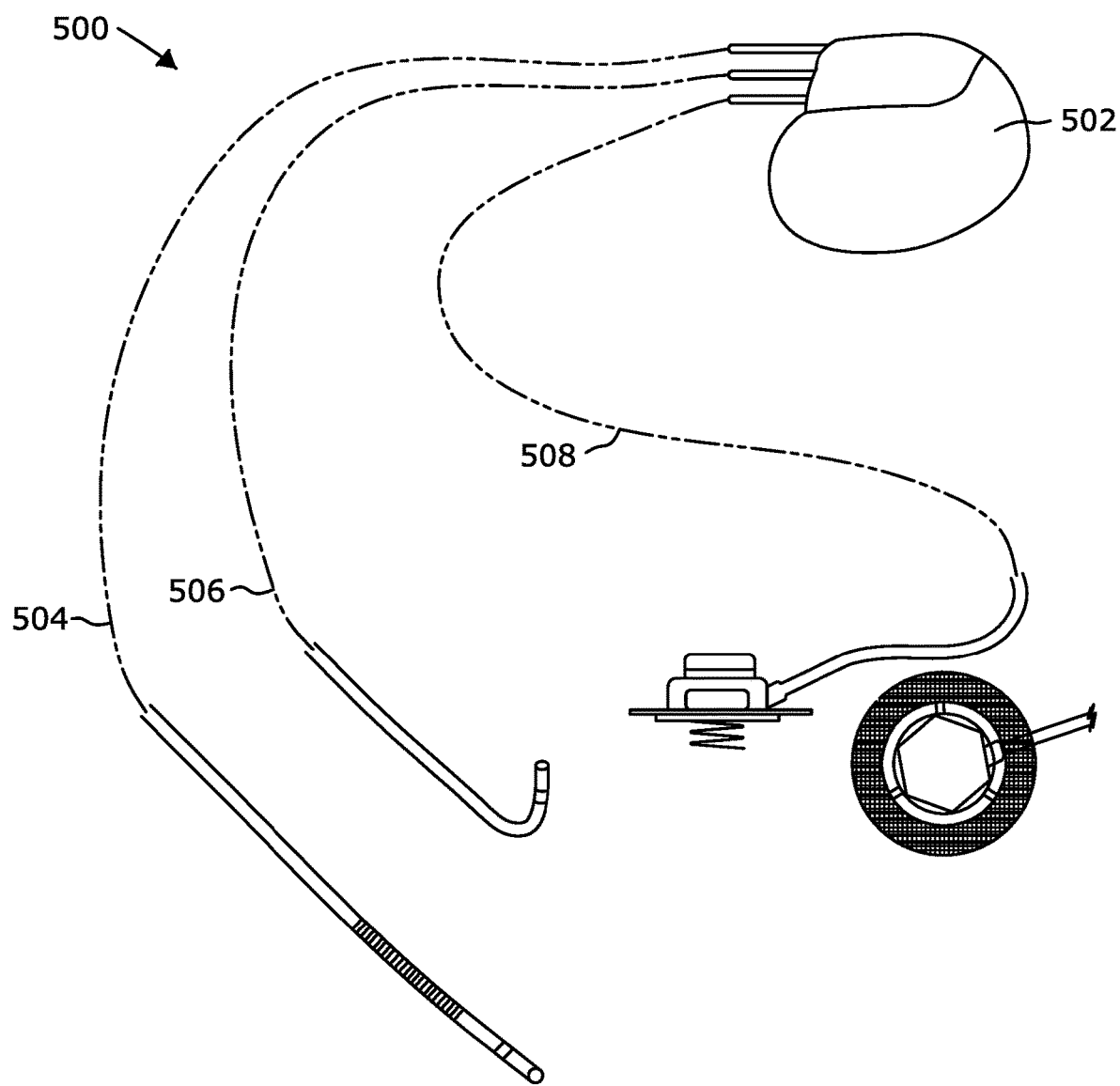
FIG. 5B is an illustration of the implantable medical device of FIG. 5A.

With reference to FIGS. 5A and 5B, a multi-therapy IMD 500 that delivers ADS therapy as part of another therapy, such as CRM therapy, includes an electronics component 502, one or more cardiac leads 504, 506, and a diaphragmatic stimulation lead 508. The one or more cardiac leads 504, 506 support pacemaker functionality, defibrillation functionality, or both. Each of the cardiac leads 504, 506 is configured to be implanted into the heart through the subclavian vein. For example, a pacing lead 506 may terminate in the right atrium, while a defibrillator lead 504 extends into the right ventricle. The diaphragmatic stimulation lead 508 supports ADS therapy and may configures the same as the lead 304 in FIG. 3B.

The ADS therapy delivery mechanism 100 portion of the diaphragmatic stimulation lead 508 may be implanted on the superior side of the diaphragm 104 through conventional thoracotomy accessed near the infraclavicular pocket, or through a sub-xiphoid approach by creating a subcutaneous tunnel from the location of the electronics component 502 parallel to the sternum until reaching a sub sternal location from where a laparoscopic thoracotomy is performed at a subxiphoid location to reach the superior region of the diaphragm.

The electronics component 502 may be implanted subcutaneously in a surgically created pocket at an infraclavicular pectoral region in accordance with standard pacemaker implant procedures. The electronics component 502 includes electrical componentry configured to: generate pacing pulses for pacing the heart 114 through one or more of the cardiac leads 504, 506, generate defibrillation energy pulses for defibrillating the heart through a cardiac lead 504, and generate asymptomatic stimulation pulses for stimulating the diaphragm 104 through the diaphragmatic stimulation lead 508. The electronics component 502 and diaphragmatic stimulation lead 508 may include electrical and mechanico-electrical componentry to perform cardiac sensing functionality for purposes of cardiac synchronized diaphragmatic stimulation. Alternatively, in the case of a pacemaker, one or more of the cardiac leads 504, 506 may perform cardiac sensing functionality for purposes of cardiac synchronized diaphragmatic stimulation.

Medical Device System

Figure 6:
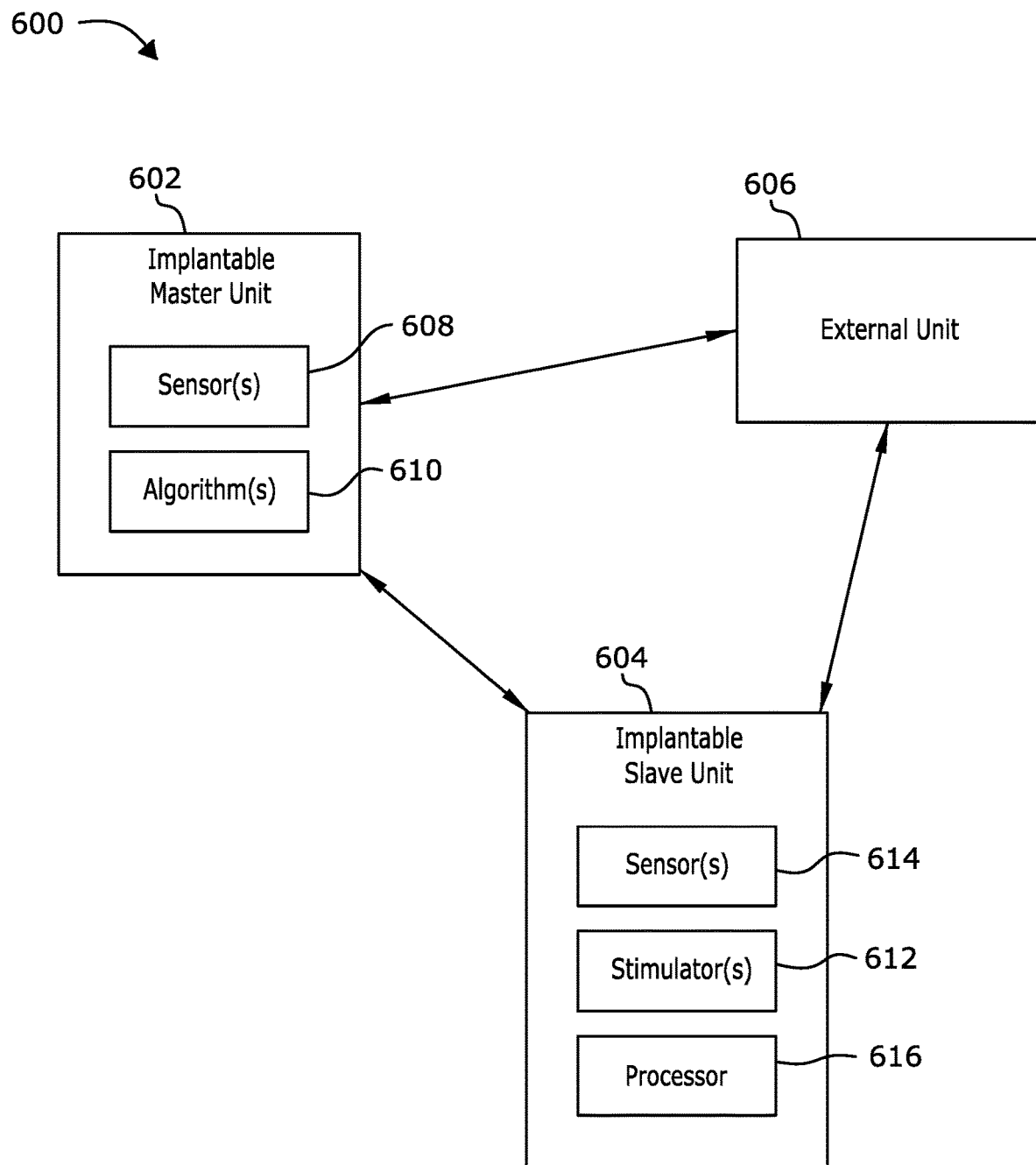
FIG. 6 is a block diagram of a medical system that includes an external device and one or more implantable devices that provide ADS therapy operating in a master/slave arrangement.

With reference to FIG. 6, a medical system 600 that provides ADS therapy includes an implantable master unit 602, at least one implantable slave unit 604 and an external unit 606. The master unit 602 determines ADS therapy configuration and controls operation of the implantable slave unit 604 to deliver ADS therapy. The master unit 602 includes sensors 608 and memory-stored algorithms 610 configured to modify ADS therapy stimulation parameters and the timing for delivering therapy, based on the monitored effect of ADS therapy. The memory-stored algorithms 610 of the master unit 602 are also configured to enable the programming of the ADS therapy configuration of the slave unit 604 using the external unit 606, e.g., programmer and user interface.

The slave unit 604 delivers ADS therapy by outputting ADS pulses through one or more stimulators 612, e.g. electrodes, placed on the diaphragm. The slave unit 604 may be actively powered by an onboard battery or passively powered, e.g., RF powered by master unit 602 or the external unit 606. The slave unit 604 may be self-charging. To this end, the slave unit 604 may be configured to convert diaphragmatic motion into energy.

The slave unit 604 may include or be coupled to one or more sensors 614. These one or more sensors 614 may provide various signals, including impedance, ECG, EMG, heart sounds, diaphragmatic motion/strength, pressure (abdominal or thoracic), strain gauge, temperature, SpO2, and PH. These signals may be processed onboard the slave unit 604 by a processor 616 or communicated to the master unit 602 for processing. The master unit 602 may analyze the signals for purposes of making therapy improvements (adjusting ADS pulse parameters and time, adjusting sensing parameters) as well as diagnostics (heart failure status, diaphragm health). The slave unit 604 may also communicate the sensed signals to the external unit 606 for diagnostic purposes Either of the master unit 602 and slave unit 604 may communicate with other implantable devices or external devices to gather further diagnostic information. For example, the implantable master units 602 and the implantable slave unit 604 may communicate with a device implanted in the pulmonary artery (PA) to collect PA pressure information. The external unit 606 could also control function as a "master", i.e. the external unit 606 could determine ADS therapy configuration and control operation of the implantable slave unit 604 or the implantable master unit 602 to deliver ADS therapy.

Implantable Medical Devices with ADS Therapy

Figure 7:
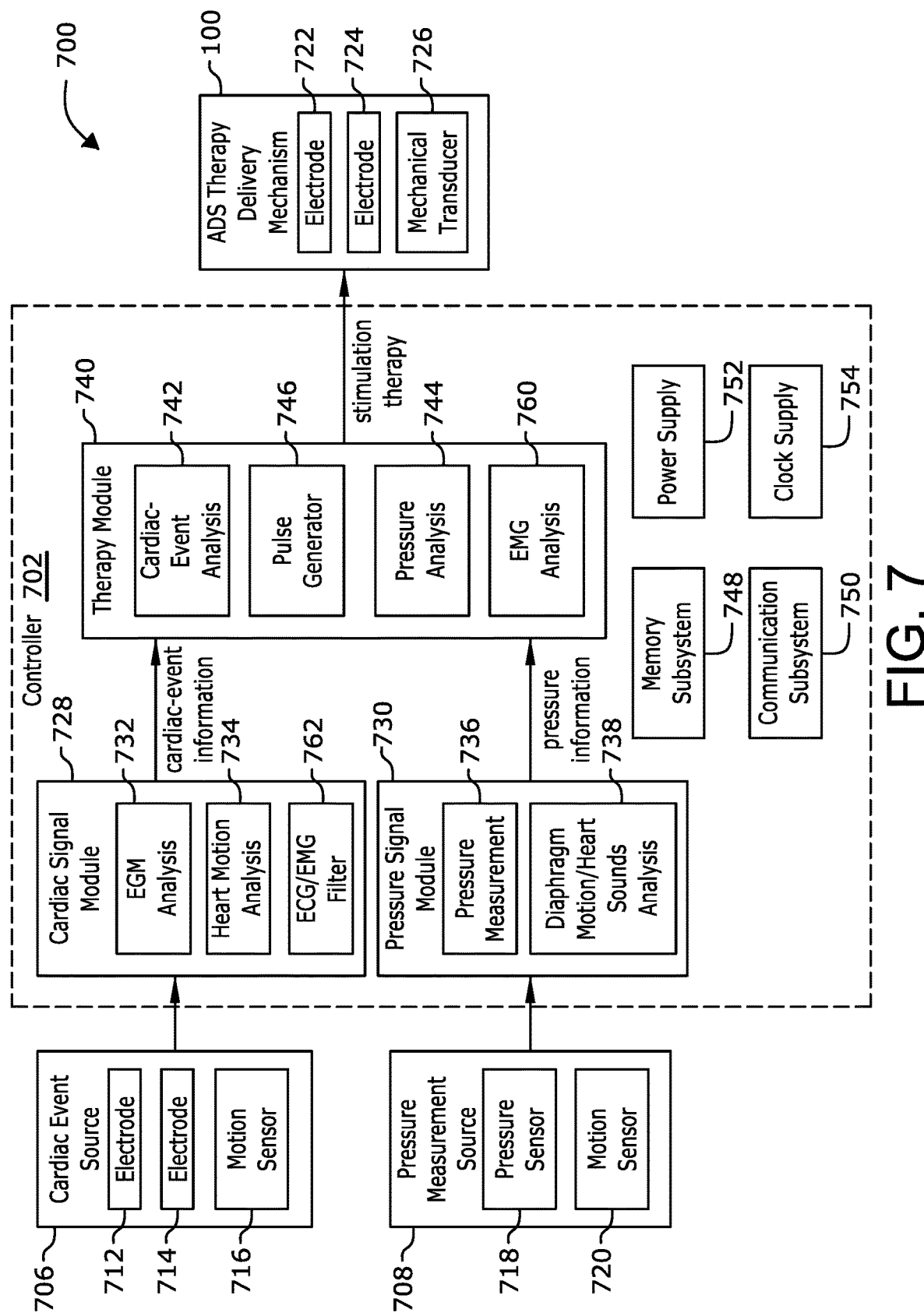
FIG. 7 is a block diagram of an implantable medical device configured to affect pressures within the intrathoracic cavity through delivery of diaphragmatic stimulation by an ADS therapy delivery mechanism.

FIG. 7 is a block diagram of an IMD 700 configured to affect pressures within the intrathoracic cavity through delivery of ADS therapy. The IMD 700 includes a controller 702, a cardiac event source 706, a pressure measurement source 708, and an ADS therapy delivery mechanism 100, each of which may be coupled for interaction with the controller, either through a wired connection or through a wireless connection. The controller 702 includes a cardiac signal module 728, a pressure signal module 730, a therapy module 740, and various other modules.

The cardiac event source 706 is configured to provide signals to the controller 702 that represent cardiac events. For example, the cardiac event source 706 may be one or more electrodes 712, 714 configured to be positioned on or near a diaphragm to sense electrical signals representative of cardiac events and to provide the signals to the controller 702. Alternatively, the one or more electrodes 712, 714 may be configured to be positioned in, on, or adjacent to an intrathoracic structure, e.g. heart, pericardium, great artery and vein, within the intrathoracic cavity. In this case, the one or more electrodes 712, 714 may be associated with a device configured to be implanted remote from the controller 702 and to provide signals sensed by the electrodes to the controller through a wireless communication link.

The cardiac event source 706 may also be a motion sensor 716 configured to be positioned on or near a diaphragm to sense motion of the heart or to sense heart sounds, and to output electrical signals representative of such motion. Alternatively, the motion sensor 716 may be configured to be positioned in, on, or adjacent to an intrathoracic structure, e.g. heart, pericardium, great artery and vein, within the intrathoracic cavity. In this case, the motion sensor 716 may be associated with a device configured to be implanted remote from the controller 702 and to provide signals sensed by the motion sensor to the controller through a wireless communication link. In either case, the motion sensor 716 may be, for example, an accelerometer (such as a multi-axial e.g., three-dimensional, accelerometer) that provides signal related to heart movement, or an acoustic transducer that provides signal related to heart sounds.

The pressure measurement source 708 is configured to provide signals to the controller 702 that represent one or more pressures within the intrathoracic cavity. "Pressures within the intrathoracic cavity" may include an intrathoracic pressure obtained directly through a pressure sensor placed in the open space of the intrathoracic cavity and outside of any intrathoracic structures, e.g. heart, pericardium, great arteries and veins, within the cavity. "Pressures within the intrathoracic cavity" may also include a measure of intrathoracic pressure obtained indirectly, for example, through an accelerometer placed outside of the intrathoracic cavity that provides a measure indicative of, or correlated with, intrathoracic pressure. "Pressures within the intrathoracic cavity" may also include pressures associated with intrathoracic structures like the heart, pericardium, great arteries and veins. For example, these "pressures within the intrathoracic cavity" may include right atrial pressure, right ventricular pressure, left ventricular pressure, and aortic pressure.

The pressure measurement source 708 may be one or more pressure sensors 718 configured to be positioned in the open space of the intrathoracic cavity, or in, on, or adjacent an intrathoracic structure, e.g. heart, pericardium, great artery and vein, within the cavity, and configured to output electrical signals representative of pressure. To these ends, the one or more pressure sensors 718 may be directly coupled to the controller 702, or alternatively, associated with a device configured to be implanted remote from the controller 702 and to provide signals sensed by the one or more pressure sensors to the controller through a wireless communication link.

Direct coupling between the one or more pressure sensors 718 and the controller 702 may be appropriate when the IMD 700 is implanted on the superior side of the patient's diaphragm at a superior implant location 122, such as shown in FIG. 1. When implanted in this location, pressure sensors 718 directly coupled to the controller 702 would be placed in the open space of the thoracic cavity 102. Remote coupling between the one or more pressure sensors 718 and the controller 702 may be appropriate when the IMD 700 is implanted on the inferior side of the patient's diaphragm at an inferior implant location 120, such as shown in FIG. 1. When implanted in this location, one or more pressure sensors 718 separately implanted in the intrathoracic cavity and remotely coupled to the controller 702 may provide pressure signals. For example, the pressure sensor 718 may be included in a device configured to be implanted: 1) in the right atrium to obtain right-atrial pressure signals, 2) in the right ventricle to obtain right ventricular pressures, 3) in the right ventricle to obtain surrogates of pulmonary artery pressure, or 4) within the pulmonary artery itself.

The pressure measurement source 708 may also be a motion sensor 720 configured to provides signals indicative of, or that correlate to, intrathoracic pressure. For example, the motion sensor 720 may be an accelerometer configured to be positioned on or near a diaphragm to sense motion of the diaphragm, and to output electrical signals representative of such motion to the controller 702. As will be described further below, fluctuations in these electrical signals correlate to changes in intrathoracic pressure associated with respiration cycles. The motion sensor 720 may also be an accelerometer or acoustic transducer configured to be positioned within the patient to sense sounds associated with cardiac function, and to output electrical signals representative of such sounds. Fluctuations in these electrical signals correlate to changes in intrathoracic pressure associated with respiration cycles. Alternatively, the motion sensor 720 may be an impedance/conductance sensor in the form of a pair of electrodes configured to be positioned in or on the diaphragm, and to output electrical signals representative of impedance or conductance of diaphragm tissue. Fluctuations in impedance or conductance correlate to changes in expansion and contraction of the diaphragm, which in turn correlate to changes in intrathoracic pressure associated with respiration cycles.

The ADS therapy delivery mechanism 100 is configured to apply stimulation to the diaphragm to cause asymptomatic, transient, partial contraction of the diaphragm. As previously mentioned, a "transient" contraction of the diaphragm is a short, twitching, caudal followed by cranial motion of the diaphragm that lasts in range of 60 to 180 msec., and is typically about 100 msec. A "partial" contraction of the diaphragm is the part or portion of the diaphragm (less than the entirety of the diaphragm) that exhibits a "transient" contraction. The stimulation is characterized by a set of stimulation parameters that induce a partial contraction of the diaphragm that does not affect respiration. More specifically, the stimulation is configured such that the diaphragm does not contract to a level that induces inspiration. The ADS therapy delivery mechanism 100 may be one or more electrodes 722, 724 configured to be positioned on or near a diaphragm to deliver electrical stimulation pulses to the diaphragm.

Considering the controller 702 in more detail, the cardiac signal module 728 of the controller receives signals from the cardiac event source 706 and is configured to process the signals to detect cardiac events of interest. For example, as will be described further below, the cardiac signal module 728 may be configured to detect one or more of an electrical cardiac event, such as a ventricular depolarization represented by an R-wave, and 2) a mechanical cardiac event, such as a ventricular contraction represented by an S1 heart sound. Information corresponding to detected cardiac events is provided to the therapy module 740, which in turn processes the cardiac-event information to determine or adjust one or more parameters of a stimulation therapy.

With respect to electrical cardiac events, the cardiac signal module 728 may include an electrogram (EGM) analysis module 732 adapted to receive electrical signals from the electrodes 712, 714 and to process the electrical signals to detect cardiac events of interest. The EGM analysis module 732 may be configured to process a cardiac electrical activity signal, e.g., an EGM signal, to detect cardiac events corresponding to atrial events, such as P waves, or ventricular events, such as R waves, QRS complexes, or T waves.

Regarding mechanical cardiac events, the cardiac signal module 728 may include a heart motion/sounds analysis module 734 for analyzing mechanical motion of the heart. The heart motion/sounds analysis module 734 is adapted to receive signals from the motion sensor 716 and to detect a cardiac event of interest. As previously mentioned, the motion sensor 716 may be, for example, an accelerometer or acoustic transducer, configured to sense a variety of mechanical and sound activities, such as diaphragm motion and heart sounds. Heart sound signals obtained through the accelerometer may be processed by the heart motion/sounds analysis module 734 to detect cardiac events.

The pressure signal module 730 of the controller 702 receives signals from the pressure measurement source 708 and is configured to process the signals for purposes of detecting a pressure event of interest or deriving a pressure measure of interest. For example, regarding measures of interest, the pressure signal module 730 may process signals from a pressure sensor 718 to determine pressure measurements under different therapy conditions, e.g., with diaphragmatic stimulation on, and with diaphragmatic stimulation off, or under different stimulation settings. The pressure signal module 730 may also process signals from a pressure sensor 718 to determine pressure measurements at different times, e.g., at or near delivery of a stimulation pulse, and at or near an occurrence of a particular cardiac event. Regarding events of interest, the pressure signal module 730 may process signals from a motion sensor 720 to detect respiration cycles and to identify one or more events of interest within the cycle, such as end inspiration. Information corresponding to detected events of interest and measures of interest, collectively referred to as pressure information, is provided to the therapy module 740. The therapy module 740, in turn, processes the pressure information to determine whether an adjustment to one or more parameters of a stimulation therapy is warranted.

Regarding the processing of signals from a pressure sensor 718, the pressure signal module 730 may include a pressure measurement module 736 for analyzing pressures within the intrathoracic cavity. The pressure measurement module 736 is adapted to receive signals from the pressure sensor 718. As previously described, the pressure sensor 718 may be a configured to be placed in the open space of the intrathoracic cavity and outside of any intrathoracic structures, e.g. heart, pericardium, great arteries and veins, within the cavity—to thereby provide a signal representing intrathoracic pressure. Alternatively, the pressure sensor 718 may be configured to be placed in, on, or adjacent an intrathoracic structure, e.g. heart, pericardium, great artery and vein, within the cavity. For example, the pressure sensor 718 may be configured to be placed in, on, or adjacent to one of the right atrium, the right ventricle, the left ventricle, the aorta, and the pulmonary artery—to thereby provide a corresponding signal presenting right atrial pressure, right ventricular pressure, left ventricular pressure, aortic pressure, or pulmonary artery pressure.

The pressure measurement module 736 is further adapted to process signals obtained from the pressure sensor 718 to derive pressure measures of interest. The pressure measurement is provided to the therapy module 740, where it is further processed to determine if stimulation therapy may be improved to provide a more desirable outcome. For example, different measures of intrathoracic pressure may be obtained for different stimulation therapies, each defined by a different set of stimulation parameter values, to determine which set of stimulation parameters provides the best measure of intrathoracic pressure. In another example, the measure of intrathoracic pressure may be compared to a predetermine threshold value, to determine if one or more of the stimulation parameters should be adjusted in an attempt to obtain, or at least more closely approach, the threshold value.

Regarding the processing of signals from a motion sensor 720, the pressure signal module 730 may include a diaphragm motion and heart sounds analysis module 738 for analyzing one or more of motion of the diaphragm and sounds associated with the heart. The diaphragm motion and heart sounds analysis module 738 is adapted to receive signals from the motion sensor 720 and to detect a pressure event of interest. As previously described, the motion sensor 720 may be an accelerometer configured to be positioned on or near a diaphragm to sense motion of the diaphragm. The motion sensor 720 may also be an accelerometer or an acoustic transducer configured to be positioned within the patient to sense sounds associated with cardiac function, and to output electrical signals representative of such sounds. Alternatively, the motion sensor 720 may be an impedance/conductance sensor in the form of a pair of electrodes configured to be positioned in or on the diaphragm.

Regarding the therapy module 740, it includes a cardiac-event analysis module 742, a pressure analysis module 744, and a pulse generator 746. The pulse generator 746 is configured to output stimulation therapy to the ADS therapy delivery mechanism 100. The stimulation therapy may be in the form of electrical stimulation, in which case the therapy may be delivered through electrodes 722, 724.

The stimulation therapy output by the pulse generator 746 is defined by one or more stimulation parameters. For electrical stimulation, the parameters may include: 1) one or more pulse parameters having a value or setting selected to define a stimulation pulse that induces a transient, partial contraction of the diaphragm, and 2) a timing parameter that controls the timing of the delivery of one or more stimulation pulses. The pulse parameters may include, for example, a pulse waveform type, a pulse amplitude, a pulse duration, and a pulse polarity. The timing parameter may include one or more offset periods or delay periods that define a time between a detected cardiac event and a delivery of an electrical stimulation pulse.

One or more of the stimulation parameters, including timing parameters and pulse parameters, may be adjusted by the therapy module 740. With respect to timing parameters, as previously mentioned, the rate of electrical stimulation may be adjusted in response to changes in the heart rate of the patient. Accordingly, the rate of delivery of electrical stimulation pulses may range, for example, between 30 pulses per minute (ppm) and 180 ppm, with a typical rate being around 60 ppm. Likewise, a delay period between a detected cardiac event and a delivery of an electrical stimulation pulse may be adjusted based on a running average of time intervals between detected cardiac events. Regarding pulse parameters, the pulse amplitude may be set to a value between 0.0 volts and 7.5 volts, and the pulse width may be set to a value between 0.0 milliseconds and 1.5 milliseconds. The amplitude may be adjusted, for example, in increments of between 0.1 to 0.5 volts, while the pulse width may be adjusted in increments of between 0.1 to 1.5 milliseconds. The polarity may be changed between a positive polarity and a negative polarity, and the waveform type may be changed from mono-phasic to biphasic, or from a square to a triangular, sinusoidal or sawtooth waveform.

The cardiac-event analysis module 742 is configured to receive cardiac-event information from the cardiac signal module 728 and to process the information to determine the timing parameter. To this end, in one configuration, the cardiac-event analysis module 742 determines a time, relative to a detected cardiac event, at which to deliver a stimulation pulse to the diaphragm. The determined time, referred to as a delay period, may be selected so that the stimulation pulse is delivered just prior to the next expected occurrence of the cardiac event.

The offset periods or delay periods may be based on the time between successive detected cardiac events. For example, the EGM analysis module 732 of the cardiac signal module 728 may be configured to detect ventricular events, e.g., R waves, and to output such detections to the therapy module 740. The cardiac-event analysis module 742 may process the detected ventricular events to determine a statistical measure of time between a number of pairs of successive ventricular events. The cardiac-event analysis module 742 may then determine one or more offset periods or delay periods based on the statistical measure, and control the pulse generator 746 to output stimulation pulses based on the determined offset period or delay period.

The pressure analysis module 744 of the therapy module 740 is configured to receive pressure information, including one or more of a measure of interest, e.g., a pressure measurement, or an event of interest, e.g., end inspiration of a respiration cycle, from the pressure signal module 730. The pressure analysis module 744 is further configured to process the received pressure information to determine if an adjustment of a stimulation parameter is warranted.

In one configuration, the pressure analysis module 744 may receive pressure information corresponding to a measure of interest, and may evaluate the measure of interest against a baseline measure of interest. For example, the received measure of interest may be a measure of an intrathoracic pressure, RA pressure, RV pressure, Ao pressure, or LV pressure at a fiducial point. The pressure analysis module 744 may compare the received measure of interest to the baseline to determine if the comparison outcome is acceptable. If the comparison outcome is not acceptable, the therapy module 740 may adjust one or more stimulation parameters for future stimulation therapy to eventually arrive at a stimulation therapy that results in an acceptable outcome.

In another configuration, the pressure analysis module 744 may receive pressure information corresponding to an occurrence of a pressure event of interest. The pressure event of interest may, for example, relate to respiration cycles of a patient and may be a point of end inspiration within a respiration cycle. In response to the receipt of such pressure information, the pressure analysis module 744 may determine to withhold stimulation therapy or to change one or more stimulation parameters.

The controller 702 includes a memory subsystem 748. The memory subsystem 748 is coupled to the cardiac signal module 728 and the pressure signal module 730, and may receive and store data representative of sensed EGMs, sensed intrathoracic cavity pressure, heart sounds, and sensed cardiovascular pressures, e.g., right ventricular pressures, left ventricular pressure, right atrial pressure, and aortic pressure. The memory subsystem 748 is also coupled to the therapy module 740 and may receive and store data representative of delivered stimulation therapies, including their associated sets of stimulation parameters and times of delivery.

The controller 702 also includes a communication subsystem 750 that enables communication between the controller and other components. These other components may form part of the IMD 700, such an a separately implanted pressure sensor within the intrathoracic cavity, may be separate from the IMD, such as an external programmer used by a physician to program the IMD. The communication subsystem 750 may include a telemetry coil enabling transmission and reception of signals, to or from an external apparatus, via inductive coupling. Alternative embodiments of the communication subsystem 750 could use an antenna for an RF link, or a series of low amplitude high frequency electrical pulses emitted by the sensor that do not illicit muscle or nervous activation, detected by sensing electrodes of the stimulating IMD. The controller 702 also includes a power supply 752 that supplies the voltages and currents necessary for each module of the controller, and a clock supply 754 that supplies the modules with any clock and timing signals.

Regarding the physical structure of the IMD 700, while the foregoing functional description of the IMD describes separate pairs of electrodes 712, 714 and 722, 724, respectively associated with the cardiac event source 706 and the ADS therapy delivery mechanism 100, a configuration of the IMD may include a single pair of electrodes configured to perform dual functions. That is, the IMD 700 may include a single pair of electrodes configured to both sense cardiac electrical activity and to deliver electrical stimulation. In this configuration, the controller 702 may include an electrode interface that is configured to switch the connection of the electrodes between the cardiac event source 706 and the ADS therapy delivery mechanism 100 as needed. The electrode interface may also provide other features, capabilities, or aspects, including but not limited to amplification, isolation, and charge-balancing functions, that are required for a proper interface between the electrodes and diaphragm tissue.

Similarly, the respective functions of the separate motion sensors 716, 720 referenced with respect to the cardiac event source 706 and the pressure measurement source 708 may be provided by a single motion sensor shared by the different sources. In this configuration, the controller 702 may include sensor interface that is configured to switch the connection of the single sensor between the cardiac event source 706 and the pressure measurement source 708 if needed. The sensor interface may also provide other features, capabilities, or aspects, including but not limited to amplification, isolation, that are required for a proper interface between the sensor and diaphragm tissue.

The cardiac signal module 728, the pressure signal module 730, and the therapy module 740 of the IMD 700 include or are associated with one or more processors configured to access and execute computer-executable instructions stored in memory associated with the modules. The one or more processors may include a central processor of the controller 702 that executes instructions for all modules 728, 730, 740. Alternatively, each of the various modules 728, 730, 740 may have a dedicated processor. Instructions executed by the one or more processor may be stored in the memory subsystem 748 or in one or more additional memory components (not shown) of the controller 702.

The one or more processors of the controller 702 may be implemented as appropriate in hardware, software, firmware, or combinations thereof. Software or firmware implementations of the one or more processor of the controller 702 may include computer-executable or machine-executable instructions written in any suitable programming language to perform the various functions described herein. The one or more processors of the controller 702 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The IMD 700 may also include a chipset (not shown) for controlling communications between the one or more processors of the controller 702 and one or more of the other components of the IMD 700. The one or more processors of the controller 702 may also include one or more application-specific integrated circuits (ASICs) or application-specific standard products (ASSPs) for handling specific data processing functions or tasks.

The memory subsystem 748 and any other memory components of the IMD 700 may include, but is not limited to, random access memory (RAM), flash RAM, magnetic media storage, optical media storage, and so forth. The memory subsystem 748 and other memory components may include volatile memory configured to store information when supplied with power and/or non-volatile memory configured to store information even when not supplied with power. The memory subsystem 748 and other memory components of may store various program modules, application programs, and so forth that may include computer-executable instructions that upon execution by the one or more processors of the controller 702 may cause various operations to be performed. The memory subsystem 748 and other memory components may further store a variety of data manipulated and/or generated during execution of computer-executable instructions by the various modules 728, 730, 740 of the controller 702.

As previously described, the IMD 700 may further include a communication subsystem 750 that may facilitate communication between the IMD 700 and one or more other devices using any suitable communications standard. For example, a LAN interface may implement protocols and/or algorithms that comply with various communication standards of the Institute of Electrical and Electronics Engineers (IEEE), such as IEEE 802.11, while a cellular network interface implement protocols and/or algorithms that comply with various communication standards of the Third Generation Partnership Project (3GPP) and 3GPP2, such as 3G and 4G (Long Term Evolution), and of the Next Generation Mobile Networks (NGMN) Alliance, such as 5G.

The memory subsystem 748 and other memory components may store various program modules, algorithms, and so forth that may include computer-executable instructions that upon execution by the one or more processors associated with the various modules 728, 730, 740 of the controller 702 may cause the various operations of these modules, as described above and further below, to be performed. To this end, the memory subsystem 748 and other memory components store computer-executable instructions that enable a processor to perform: 1) the EGM analysis and heart motion analysis operations of the cardiac signal module 728, 2) the pressure measurement and diaphragm motion/heart sounds analysis operations of the pressure signal module 730, and 3) the cardiac-event analysis, pressure analysis, and EMG analysis of the therapy module 740.

The memory subsystem 748 and other memory components also store computer-executable instructions that enable a processor associated with the therapy module 740 to perform the signal processing, analysis, and ADS therapy delivery associated with each of: 1) the dual-pulse ADS therapy disclosed further below, 2) the paired-pulse ADS therapy disclosed further below, 3) multiple pulse ADS therapy disclosed further below, and 4) the EGM monitoring and health assessment disclosed further below.

The various modules 728, 730, 740 of the controller 702 may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a smart card, a flash memory device (e.g., card, stick, key drive), random access memory (RAM), read only memory (ROM), programmable ROM (PROM), erasable PROM (EPROM), electrically erasable PROM (EEPROM), a general register, or any other suitable non-transitory medium for storing software.

ADS Therapy Algorithms

Having thus described the structural components of an IMD 700, and their respective functions, a description of several ADS therapy algorithms implemented by the IMD are described.

One algorithm relates to ADS therapy where a single stimulation pulse is delivered to the diaphragm per cardiac cycle. Another algorithm relates to ADS therapy where dual stimulation pulses are delivered to the diaphragm per cardiac cycle, one during the diastolic phase of the cardiac cycle and the other during the systolic phase. Another algorithm relates to ADS therapy where a pair of closely spaced stimulation pulses are delivered to control the duration of diaphragm movement in a particular direction, e.g., cranial direction or caudal direction. Yet another algorithm relates to ADS therapy where multiple stimulation pulses are delivered to the diaphragm at a cardiac-cycle specific frequency based on heart rate, to cause a permanent partial mechanical modulation of the diaphragm.

Single Pulse ADS Therapy

ADS therapies that deliver a single ADS pulse per cardiac cycle are disclosed, for example, in U.S. Pat. No. 10,315,035, titled "Hemodynamic Performance Enhancement Through Asymptomatic Diaphragm Stimulation" and U.S. Pat. No. 10,335,592, titled "Systems, Devices, and Methods for Improving Hemodynamic Performance Through Asymptomatic Diaphragm Stimulation."

Dual-Pulse ADS Therapy

Dual-pulse ADS therapy is a therapy where multiple, e.g., two, asymptomatic stimulation pulses are delivered to the diaphragm per cardiac cycle. This ADS therapy results in multiple transient, partial contractions of the diaphragm per cardiac cycle, which translates into an intrathoracic pressure modulation most favorable for the optimization of preload and afterload in support of the patient's hemodynamics. As previously mentioned, a "transient" contraction of the diaphragm is a short, twitching, caudal followed by cranial motion of the diaphragm that lasts in the range of 60 to 180 msec., and is typically about 100 msec. A "partial" contraction of the diaphragm is the part of the diaphragm (less than the entirety of the diaphragm) that exhibits a "transient" contraction.

Figure 8A:
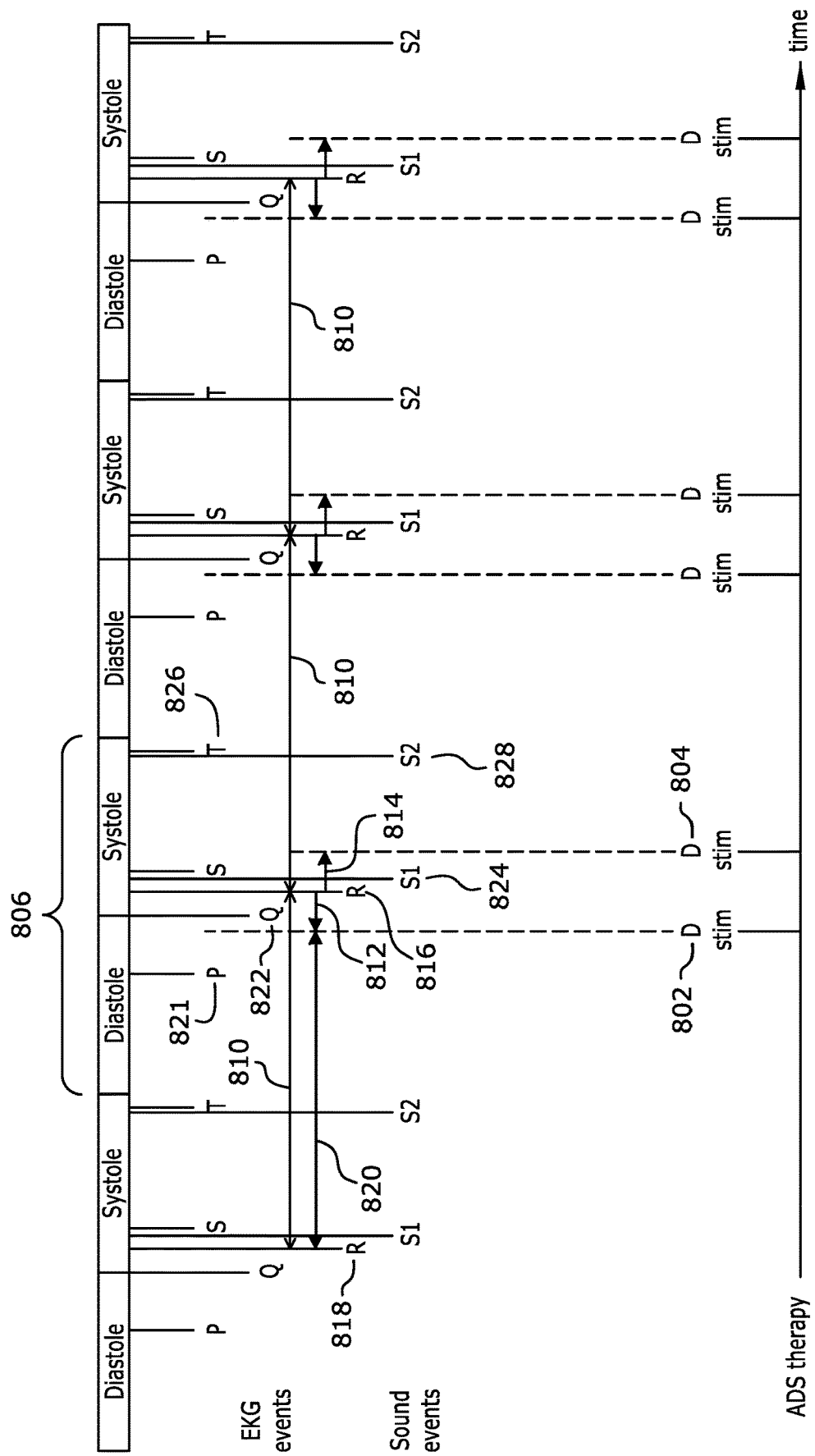
FIG. 8A is a schematic diagram of an ADS therapy including dual stimulation pulses per cardiac cycle, with one pulse delivered during late diastole and the other pulse delivered during early systole.
Figure 8B:
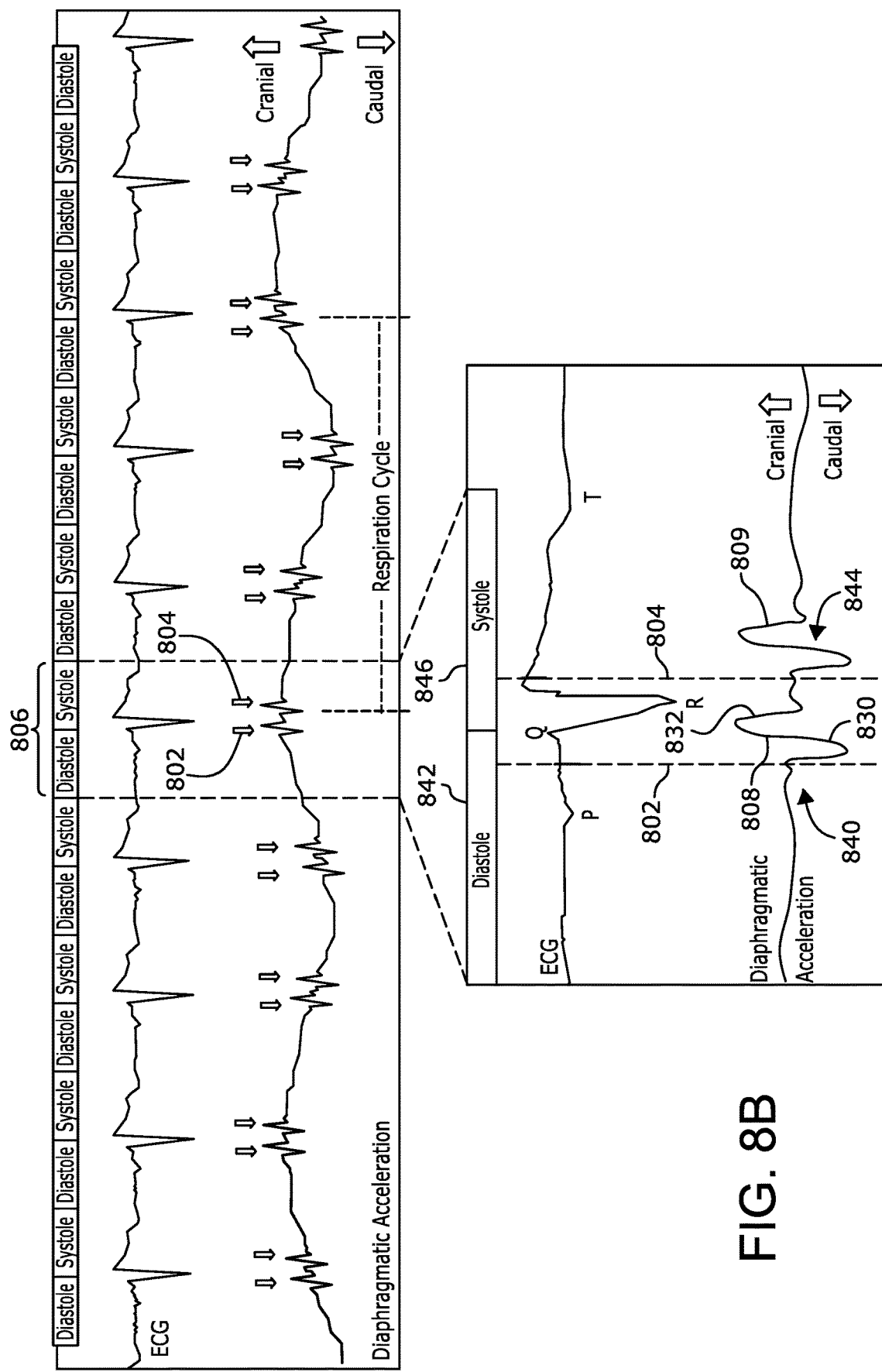
FIG. 8B are illustrations of an electrocardiogram (ECG) waveform and a diaphragmatic acceleration waveform including spaced apart pairs of transient, partial contractions of the diaphragm resulting from delivery of the ADS therapy of FIG. 8A, wherein each transient, partial contraction results from the delivery of a single ADS pulse and includes a caudal phase, during which a portion of the diaphragm is moving in the caudal direction, and cranial phase during which a portion of the diaphragm is moving in the cranial direction.

With reference to FIGS. 8A and 8B, in one embodiment, at least two diaphragmatic stimulation pulses 802, 804 are delivered per cardiac cycle 806. The delivery of each stimulation pulse 802, 804 is synchronized to a cardiac event so that one stimulation pulse 802 is delivered in the latter part of diastole (preload benefit) of the cardiac cycle 806 and the other stimulation pulse 804 is delivered at the early part of systole (afterload benefit) of the cardiac cycle. As shown in FIG. 8B, each of these stimulation pulses 802, 804 causes a corresponding transient, partial contraction 808, 809 of the diaphragm, each comprising a movement in the caudal direction followed by a movement in the cranial direction.

Referring to FIG. 8A, "the latter part of diastole" may be the atrial filling window (between a P wave and following Q point), with the corresponding stimulation pulse 802 preferably being delivered closer to the Q point than the P wave. The "early part of systole" may be the systolic output (between a S1 heart sound and following S2 heart sound), with the corresponding stimulation pulse 804 preferably being delivered at an offset of about 50-100 msec. after the mitral valve component of the S1 heart sound.

The triggering of the two diaphragmatic stimulation pulses 802, 804 may be timed relative to a sensed occurrence of a valid cardiac event. In one embodiment, delivery of each of the two diaphragmatic stimulation pulses 802, 804 is triggered by the same sensed occurrence of a cardiac event. In another embodiment, one of the two diaphragmatic stimulation pulses 802, 804 is triggered by a sensed occurrence of a valid cardiac event and the other of the two diaphragmatic stimulation pulses 802, 804 is triggered by a sensed occurrence of another cardiac event different from the one that triggered the other diaphragmatic stimulation pulse.

A valid cardiac event may be a valid ventricular event (V-event) or a valid atrial event (A-event). The sensed occurrence of a valid cardiac event may correspond to an electrical cardiac event or a mechanical cardiac event. Electrical cardiac events may be a feature of an ECG, such as a P wave, a QRS complex, a Q point of a QRS complex, a R wave, a S point of a QRS complex or a T wave. Mechanical cardiac events may be a S1 heart sound, a S2 heart sound, a S3 sound or a S4 heart sound.

A valid V-event may be an electrical or mechanical event of a ventricle sensed either electrically or mechanically by an IMD. In one configuration, a valid electrical V-event may be an intrinsic depolarization of the ventricle that results from normal electrical conduction through the atrioventricular (AV) node. In electrocardiogram (ECG) terminology, such a valid electrical V-event may be a normal R wave, a normal QRS complex, or a normal T wave. In another configuration, a valid electrical V-event may be a ventricular pacing stimulus delivered to the ventricle and sensed by the IMD. In yet another configuration, a valid electrical V-event may be an evoked response of the ventricle sensed by the IMD. In this regard, an evoked ventricular event corresponds to an electrical depolarization of the ventricle that results from the delivery of a ventricular pacing stimulus.

Associated with a ventricular depolarization, whether intrinsic or evoked, is a physical contraction of the ventricle. Accordingly, each of an intrinsic ventricular depolarization and an evoked ventricular depolarization may be sensed by a mechanical sensor, e.g., in the form of an S1 heart sound or an S2 heart sound. In some cases, the IMD may be programmed to consider what would otherwise be a valid V-event, as a non-valid V-event if that V-event is associated with a non-normal cardiac episode. For example, if the otherwise valid V-event occurs during an episode of ventricular fibrillation or is followed by a premature ventricular contraction, the IMD may deem that V-event non-valid for purposes of delivering diaphragmatic stimulation.

A valid A-event may be an electrical event of an atrium, sensed either electrically or mechanically by an IMD. In one configuration, a valid electrical A-event may be an intrinsic depolarization of the atrium that originates from the sinoatrial (SA) node. In ECG terminology, such a valid electrical A-event may be a normal P wave. In another configuration, a valid electrical A-event may be an atrial pacing stimulus delivered to the atrium and sensed by the IMD. In yet another configuration, a valid electrical A-event may be an evoked response of the atrium sensed by the IMD. In this regard, an evoked atrial event corresponds to an electrical depolarization of the atrium that results from the delivery of an atrial pacing stimulus.

Associated with atrial depolarization, whether intrinsic or evoked, is a physical contraction of the atrium. Accordingly, each of an intrinsic atrial depolarization and an evoked atrial depolarization may be sensed by a mechanical sensor, e.g., in the form of an S4 heart sound. In some cases, the IMD may be programmed to consider what would otherwise be a valid A-event, as a non-valid A-event if that A-event is associated with a non-normal cardiac episode. For example, if the otherwise valid A-event occurs during an episode of atrial tachycardia, atrial fibrillation, or atrial flutter, the IMD may deem that A-event non-valid for purposes of delivering diaphragmatic stimulation.

With reference to FIG. 8A, the triggering of the two diaphragmatic stimulation pulses 802, 804 is timed relative to the same sensed occurrence of an intrinsic R-wave, with one stimulation pulse 802 delivered in accordance with a calculated negative offset from the R-wave for the late diastolic pulse, and the other stimulation pulse 804 delivered in accordance with a calculated positive offset to be in the early systolic part. The calculation could be a either a value determined and programmed by the clinician or an actual calculation performed by an IMD 700 based on time intervals between ECG and/or heart sound signal fiducial points.

Regarding calculations performed by an IMD 700, in accordance with embodiments disclosed herein, the timings of the delivery of diaphragmatic stimulation pulses 802, 804 may be determined based on sensed occurrences of cardiac events that occur over a number of cardiac cycles 806. For example, a VV interval 810 may be measured over a number of cardiac cycle 806 to obtain an average VV interval. Based on this average VV interval the IMD 700 may calculate a set of offset periods, including a first offset period 812 that defines when a first diaphragmatic stimulation pulses 802 is delivered relative to a cardiac event 816, and a second offset period 814 that defines when a second diaphragmatic stimulation pulses 804 is delivered relative to the cardiac event 816. The first offset period 812 is characterized by a negative offset relative to the cardiac event 816 and may be described as an "early" or "anticipatory" stimulation in that it occurs before the cardiac event. The second offset period 814 is characterized by a positive offset relative to the cardiac event 816 and may be described as a "late" stimulation in that it occurs after the cardiac event.

The value of the first offset period 812 is selected so that the first stimulation pulse 802 is delivered during late diastole. To this end, the IMD 700 may sense occurrences of other cardiac events to determine a value that results in such placement. For example, with reference to FIG. 8A, the IMD 700 may sense P waves 821 and Q points 822 over the same number of cardiac cycles 806 that it senses R waves 816. Based on the respective timing differences between the P wave 821 and R wave 816 and the Q point 822 and R wave, over a number of cardiac cycles 806, the IMD 700 may calculate a first offset period 812 that places delivery of the first stimulation pulse 802 somewhere between the P wave 821 and Q point 822 that are prior to the R wave 816. In one embodiment the first stimulation pulse 802 is placed so that it is closer to Q point 822 than it is to the P wave 821.

The value of the second offset period 814 is selected so that the second stimulation pulse 804 is delivered during early systole. To this end, the IMD 700 may sense occurrences of other cardiac events to determine a value that results in such placement. For example, with reference to FIG. 8A, the IMD 700 may sense S1 heart sounds 824 and T waves 826 over the same number of cardiac cycles 806 that it senses R waves 816. Based on the respective timing differences between the S1 heart sound 824 and R wave 816 and the T wave 826 and R wave, over a number of cardiac cycle 806, the IMD 700 may calculate a second offset period 814 that places delivery of the second stimulation pulse 804 somewhere between the S1 heart sound 824 and the T wave 826 that are after the R wave 816. In one embodiment the second stimulation pulse 804 is placed so that it is closer to the S1 heart sound 824 than it is to the T wave 826.

Regarding the early stimulation 802, the delivery of this stimulation is triggered by the sensed occurrence of the previous cardiac event 818. In other words, upon detection of the cardiac event 818, the diaphragmatic stimulation pulse 802 is delivered a delay period 820 after such detection that places the pulse in late diastole. To this end, the IMD 700 may calculate the delay period 820 as the difference between the VV interval 810 and the first offset period 812.

While the foregoing description has focused on the delivery of dual stimulation pulses 802, 804 timed to occur respectively during diastole and systole based on a detection of the same cardiac event, e.g., an R wave, the delivery of these stimulation pulses may be timed to occur during diastole and systole based on detections of other cardiac events.

In some cases, it may be desirable to simulate the diaphragm based on certain diastole cardiac events, such as an offset of passive left ventricular filling or an onset of atrial filling, the occurrences of which generally coincide with a P wave of an ECG. To this end, the IMD 700 may monitor the time between a P wave 821 and a following Q point 822 over a number of cardiac cycles 806, and calculate an offset from a P wave that places a delivery of a stimulation pulse 802 after the P wave 821 but before the following Q point 822. Once this offset it determined, subsequent detections of these diastole cardiac events by an IMD 700 may trigger a delivery of a stimulation pulse 802 during late diastole.

In some cases, it may be desirable to simulate the diaphragm based on certain systole cardiac events, such as: 1) an onset of electrical systole or an offset of atrial filling, the occurrences of which generally coincide with a Q point 822 of an ECG; 2) an offset of electrical systole, the occurrences of which generally coincide with a T wave 826 of an ECG; 3) an onset of mechanical systole, the occurrences of which generally coincide with a S1 heart sound 824; 4) an offset of mechanical systole or an onset of passive left ventricular filling, the occurrences of which generally coincide with a S2 heart sound 828; 5) an onset of left ventricular systolic output, the occurrences of which generally coincide with a mitral valve component of a S1 heart sound 824; 6) an offset of left ventricular systolic output, the occurrences of which generally coincide with an aortic valve component of a S2 heart sound 828; 7) an onset of right ventricular systolic output, the occurrence of which generally coincide with a tricuspid valve component of a S1 heart sound 824; or 8) an offset of right ventricular systolic output, the occurrences of which generally coincide with a pulmonic valve component of a S2 heart sound 828.

To this end, the IMD 700 may monitor the time between one of a Q point 822 or an S1 heart sound 824 and a following one of a T wave 826 or a S2 heart sound 828 over a number of cardiac cycles 806, and calculate an offset from of a Q point 822 or an S1 heart sound 824 that place a delivery of a stimulation pulse 804 after the Q point but before the T wave, or after the S1 heart sound but before the S2 heart sound. Once this offset it determined, subsequent detections of these systole cardiac events by an IMD 700 may trigger a delivery of a stimulation pulse 804 during early systole.

As shown in FIG. 8B, the relative timing of the first ADS pulse 802 and the second ADS pulse 804 results in two separate and distinct transient, partial contraction 808, 809 of the diaphragm. Each of these partial contractions 808, 809 include a caudal phase 830 corresponding to a movement in the caudal direction, followed by cranial phase 832 corresponding to a movement in the cranial direction.

Figure 9:
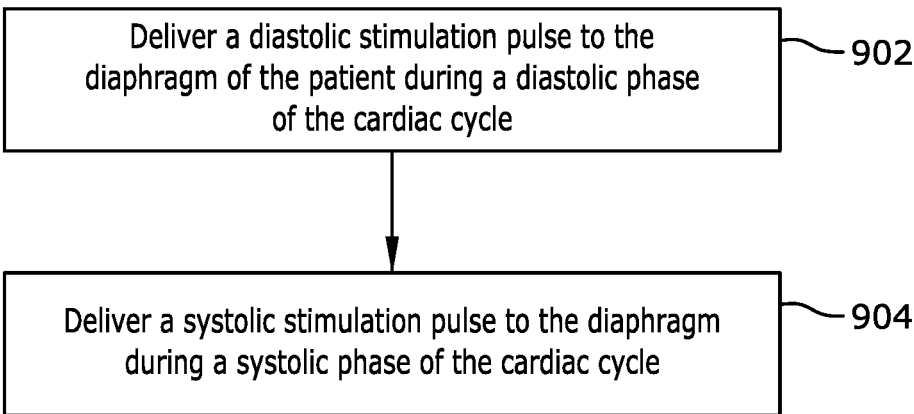
FIG. 9 is a flowchart of a method of affecting pressure in an intrathoracic cavity of a patient through the delivery of dual ADS pulses per cardiac cycle.

FIG. 9 is a flowchart of a method of affecting pressure in an intrathoracic cavity of a patient through delivery of dual ADS pulses per cardiac cycle. The method may be performed by the IMD 700 of FIG. 7 or a similar apparatus or system. For example, the method may be performed by an apparatus having one or more electrodes 722, 724 configured for placement on or near a diaphragm and a controller 702 coupled to the one or more electrodes. The controller 702 is configured, for example, though executable program instructions stored in a memory, to perform the method described below with reference to FIG. 9.

At block 902, and with additional reference to FIGS. 8A and 8B, a diastolic stimulation pulse 802 is delivered to a diaphragm of the patient during a diastolic phase of a cardiac cycle 806 of the patient. The diastolic stimulation pulse 802 results in an asymptomatic, transient, partial contraction 840 of the diaphragm during a diastolic phase 842 of the cardiac cycle 806.

Delivery of the diastolic stimulation pulse 802 may be timed to a cardiac event. To this end, an occurrence of a first cardiac event 818 is detected, and the diastolic stimulation pulse 802 is delivered at or near the end of a diastolic offset period 820 from the detected first cardiac event. The diastolic offset period 820 places the delivery of the diastolic stimulation pulse 802 at a latter part of diastole of the cardiac cycle 806.

The diastolic offset period 820 may be determined by detecting, over a plurality of cardiac cycles, a time of occurrence of: a) the first cardiac event 818, and b) one of an onset of an atrial event 821, e.g., a detected P wave, and an offset of a first ventricular event 821, e.g., also a detected P wave, and c) an onset of a second ventricular event 822, 824 that follows the onset of the atrial event and the onset of the first ventricular event. The onset of a second ventricular event may correspond to a detected Q point 822 in a QRS complex, or a detected S1 heart sound 824. The respective times of occurrences are processed to calculate a period of time from the first cardiac events 818 to a time between a) either of an onset of an atrial event 821 or an offset of a first ventricular event 821, and b) an onset of a second ventricular event 822, 824 that follows the onset of the atrial event and the onset of the first ventricular event. The calculated period of time corresponds to the diastolic offset period 820.

At block 904, a systolic stimulation pulse 804 is delivered to the diaphragm during a systolic phase of the cardiac cycle 806. The systolic stimulation pulse 804 results in an asymptomatic, transient, partial contraction 844 of the diaphragm during a systolic phase 846 of the cardiac cycle 806.

Delivery of the systolic stimulation pulse 804 may also be timed to a cardiac event. To this end, an occurrence of a second cardiac event 816 is detected, and the systolic stimulation pulse 804 is delivered at or near the end of a systolic offset period 814 from the detected second cardiac event 816. The systolic offset period 814 places the delivery of the systolic stimulation pulse 804 at an early part of systole of the cardiac cycle 806.

The systolic offset period 814 may be determined by detecting, over a plurality of cardiac cycles, a time of occurrence of: a) the second cardiac event 816, and b) one of an onset of electrical systole 822, e.g., a detected Q point, and an onset of mechanical systole 824, e.g., a detected S1 heart sound, and c) one of an offset of electrical systole 826, e.g., a detected T wave, and an offset of mechanical systole 828, e.g., a detected S2 heart sound. The respective times of occurrences are processed to calculate a period of time from the second cardiac events 816 to a time between: a) either of an onset of electrical systole 822 or an onset of mechanical systole 824, and b) either of an offset of electrical systole 826 or an offset of mechanical systole 828. The calculated period of time corresponds to the systolic offset period 814.

While in the foregoing description, the second cardiac event 816 in FIG. 8A that triggers delivery of the systolic stimulation pulse 804 is different from the first cardiac event 818 that triggers delivery of the diastolic stimulation pulse 802, the first cardiac event and the second cardiac event may be the same event within a same cardiac cycle. For example, delivery of each of the diastolic stimulation pulse 802 and the systolic stimulation pulse 804 may be timed to a detection of a P wave 821.

In other embodiments, the first cardiac event 818 that triggers delivery of a diastolic stimulation pulse 802 and the second cardiac event 816 that triggers delivery of a systolic stimulation pulse 804, may be the same cardiac event type in consecutive cardiac cycles. In the example of FIG. 8A, the first cardiac event 818 is a detected R wave from a prior cardiac cycle that triggers the diastolic stimulation pulse 802 in the current cardiac cycle 806, while the second cardiac event 816 is a detected R wave in the current cardiac cycle that triggers the diastolic stimulation pulse 802 in the current cardiac cycle 806. While the first and second cardiac events are electrical events, e.g., R waves, the first and second cardiac events may be mechanical events, e.g., an S1 heart sound.

In other embodiments, the first cardiac event that triggers delivery of a diastolic stimulation pulse 802 and the second cardiac event that triggers delivery of a systolic stimulation pulse 804, may be different cardiac events in a same cardiac cycle. For example, with reference to FIG. 8A, the first cardiac event may be a detected P wave 821 in the current cardiac cycle 806, while the second cardiac event 816 may be a detected R wave in the current cardiac event. Again, while the first and second cardiac events may be electrical events, e.g., P wave, and R wave, one or more of the first and second cardiac events may be a mechanical event, e.g., an S1 heart sound.

Paired-Pulse ADS Therapy

Figure 10:
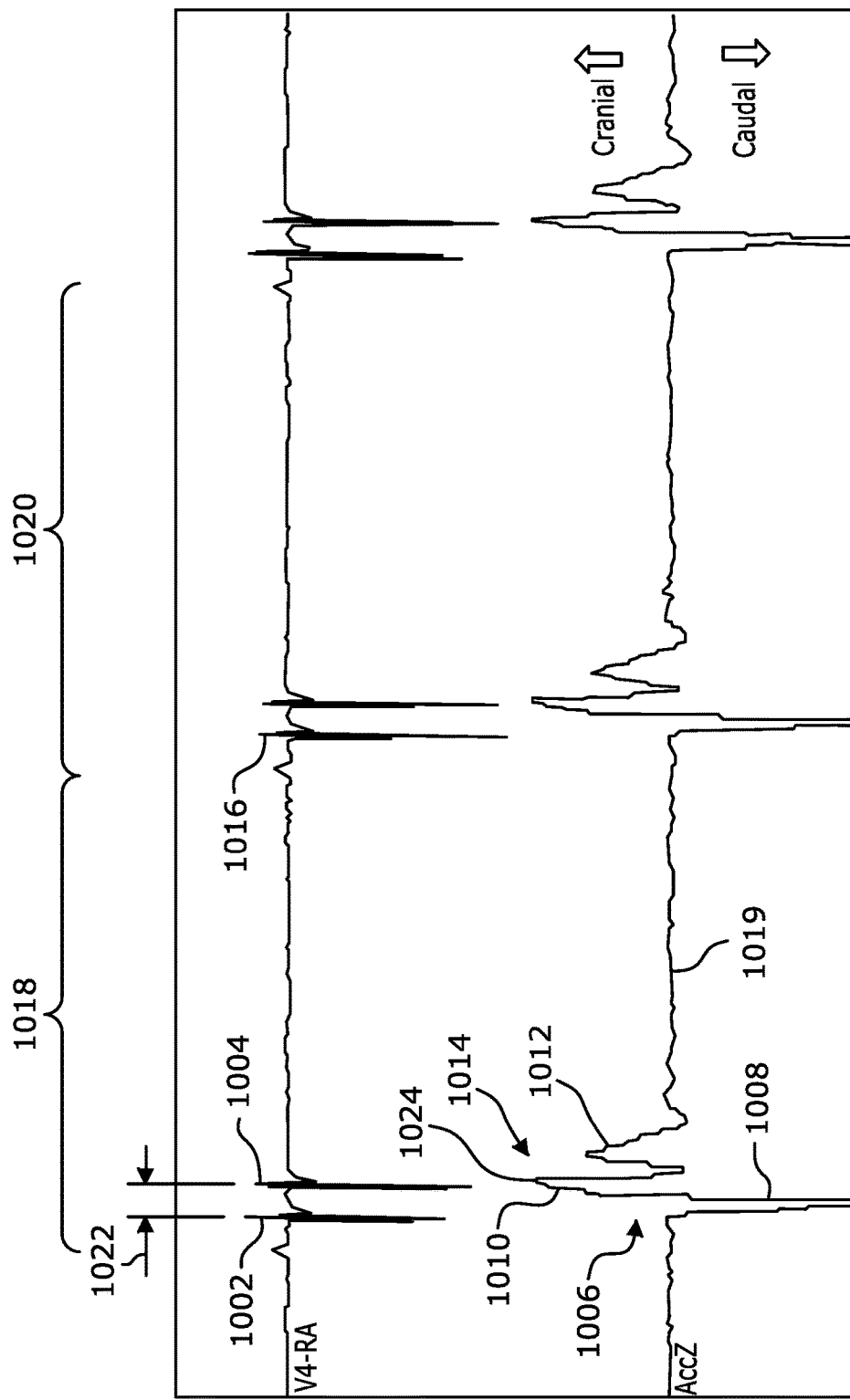
FIG. 10 are illustrations of an ECG waveform and a diaphragmatic acceleration waveform including a series of transient, partial contractions, each having a caudal phase followed by an extended or enhance cranial phase that results from delivery of a closely timed pair of ADS pulses.

With reference to FIG. 10, in accordance with embodiments disclosed herein, a pair of ADS pulses 1002, 1004 may be delivered in a way that manipulates a transient, partial contraction of a diaphragm in a way that enhances and adds to the duration of one of a caudal phase or a cranial phase of the contraction. For example, it is possible to extend the duration of a cranial phase 1014 of a transient, partial contraction of the diaphragm for a brief time through delivery of the second ADS pulse 1004 soon after the delivery of the first ADS pulse 1002, without the extended cranial phase overlapping with the delivery of a next ADS pulse 1016 that is triggered by a next cardiac event. A delivery of an ADS pulse 1004 for purpose of extending a particular phase of contraction is feasible because the refractory period of the diaphragm is short, e.g., between 1 msec. and 4 msec., and nearly independent of heart rate as the diaphragm tone is driven by respiratory needs. In other words, even in cases of increased heart rate, there is sufficient time during a current cardiac cycle 1018 to extend one or both of a cranial phase 1014 of a partial contraction or a caudal phase of a partial contraction, before the next cardiac cycle 1020 initiates and triggers a next ADS pulse 1016.

Further on this embodiment, and with continued reference to FIG. 10, an appropriately timed and spaced apart pair of ADS pulses including a first ADS pulse 1002 and a second ADS pulse 1004 may shift the balance of contraction phases to one of predominantly caudal or predominantly cranial to impact intrathoracic pressure and cardiovascular flow. To this end, a portion 202 or part of the diaphragm 204 may be stimulated as it is moving in either of the caudal phase or the cranial phase of a contraction. By stimulating the portion 202 of the diaphragm 204 prior to that portion completing its transient contraction, the morphology of the mechanical response of the portion can be altered in a way to shift the balance of the phases of the transient contraction between one that is predominantly caudal, i.e., the portion 202 of the diaphragm 204 moves in the caudal direction for a period of time greater than the time the part moves in the cranial direction, and predominantly cranial, i.e., the portion 202 of the diaphragm 204 moves in the cranial direction for a period of time greater than the time the part moves in the caudal direction.

In one embodiment, a primary function and benefit of second ADS pulse 1004 is to shorten the first cranial phase initiated by the first ADS pulse 1002 as it might come too early during a cardiac cycle 1018. The second ADS pulse 1004 cuts that first cranial phase short and creates a second cranial phase later in the cardiac cycle 1018 when there is hemodynamic benefit achieved by increasing the pressure on the heart/vessels. An illustration of a shift in diaphragm acceleration resulting from the delivery of a pair of appropriately timed consecutive ADS pulses 1002, 1004 is shown in FIG. 10. The first ADS pulse 1002 results in a typical caudal-followed-by-cranial transient, partial contraction 1006 or twitch of the diaphragm having a caudal phase 1008 followed by the beginning of a first cranial phase 1010. During the first cranial phase 1010 of the transient, partial contraction, a second ADS pulse 1004 is delivered. For example, the timing of delivery of the second ADS pulse 1004 may be based on the typical time for a diaphragm to complete a transient, partial contraction. This contraction time is typically between 60 to 180 msec., with the caudal phase taking about half the total time and the cranial phase taking half the total time. Accordingly, an appropriately timed second ADS pulse 1004 for purposes of extending a cranial phase 1014 may be delivered somewhere between 50-75 msec. after the delivery of the first ADS pulse 1002.

Delivery of the second ADS pulse 1004 at this time overlaps with the effect of the first ADS pulse 1002 and induces a sharp change, e.g., reduction, in the acceleration of the diaphragm in the cranial direction. This change in acceleration manifests graphically in FIG. 10 as a narrow-width first cranial phase 1010 having a short, near-vertical drop downward to the baseline 1019. Subsequent to this reduction in acceleration, the second ADS pulse 1004 induces an increase in acceleration of the diaphragm in the cranial direction, followed by a reduction in the acceleration of the diaphragm in the cranial direction. These changes in acceleration manifests graphically in FIG. 10 as a second cranial portion 1012. The second cranial portion 1012, together with the first cranial portion 1010 produce an overall diaphragmatic contraction that is predominately cranial. In other words, the balance of the overall diaphragm movement is shifted to the cranial phase. This is beneficial because movement of the diaphragm in the cranial direction results in an increase in intrathoracic pressure, which in turn increases the pressure on the heart and vessels in a way that it augments cardiac output if timed correctly to the beginning of systole.

Figure 11:
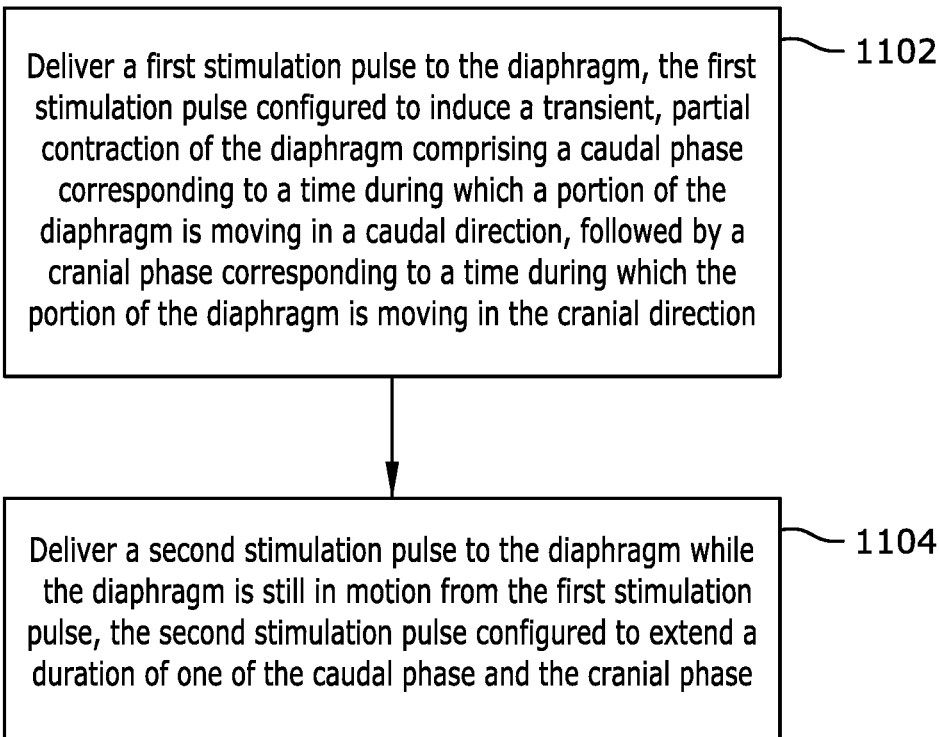
FIG. 11 is a flowchart of a method of affecting pressure in an intrathoracic cavity of a patient through delivery of paired ADS pulses.

FIG. 11 is a flowchart of a method of affecting pressure in an intrathoracic cavity of a patient through delivery of paired ADS pulses. The method may be performed by the IMD of FIG. 7 or a similar apparatus or system. For example, the method may be performed by an apparatus having one or more electrodes 722, 724 configured for placement on or near a diaphragm and a controller 702 coupled to the one or more electrodes. The controller 702 is configured, for example, though executable program instructions stored in a memory, to perform the method described below with reference to FIG. 11.

At block 1102, and with additional reference to FIG. 10, a first stimulation pulse 1002 is delivered to a diaphragm of the patient. The first stimulation pulse 1002 is configured to induce a transient, partial contraction 1006 of the diaphragm comprising a caudal phase 1008 corresponding to a time during which a portion of the diaphragm is moving in a caudal direction, followed by a cranial phase 1010 corresponding to a time during which the portion of the diaphragm is moving in the cranial direction.

Delivery of the first stimulation pulse 1002 to the diaphragm may be triggered by a cardiac event. To this end, and with additional reference to FIG. 8A, an occurrence of a cardiac event 816, e.g., an R wave, is detected by the IMD 700, and the first stimulation pulse 1002 is output by the IMD at or near the end of a first offset period 814 from the detected cardiac event. The occurrence of a cardiac event 816 may be detected based on signals sensed by the one or more electrodes 722, 724 configured for placement on or near the diaphragm, or by one or more electrodes 712, 714 placed on or near a heart, or by a motion sensor 716 placed on or near a heart.

At block 1104, a second stimulation pulse is delivered to the diaphragm while the diaphragm is still in motion from the first stimulation pulse 1002. The second stimulation pulse may be configured to extend a duration of one of the caudal phase 1008 and the cranial phase 1014 of the transient, partial contraction of the diaphragm. To this end, the stimulation parameters, e.g., pulse amplitude, pulse width, etc., that define the second stimulation pulse may be the same as the stimulation parameters that define the first stimulation pulse 1002. Alternatively, the stimulation parameters that define the second stimulation pulse may be different. For example, it may be beneficial for the second stimulation pulse to have a higher stimulation energy to solicit a more forceful response of the diaphragm through the second stimulus, and thereby increasing the hemodynamic effect the resulting extended caudal movement or cranial movement could have.

Delivery of the second stimulation pulse to the diaphragm may be triggered by or timed to various different events. For example, with reference to FIG. 10, which illustrates the effect of a second stimulation pulse 1004 that extends the duration of a cranial phase 1014, the second stimulation pulse 1004 may be output by the IMD 700 at or near the end of a second offset period 1022 that may be timed relative to the delivery of the first stimulation pulse 1002. For example, the IMD 700 may be programmed to output the second stimulation pulse 1004 between 20 msec. and 300 msec. after delivery of the first stimulation pulse 1002. In another configuration, the second offset period may be relative to an occurrence of a cardiac event. This cardiac event may be the same cardiac event that triggered the delivery of the first stimulation pulse 1002.

In another configuration, the IMD 700 is configured to determine the second offset period 1022 by detecting a pair of closely associated cardiac events in a cardiac cycle. For example, a pair of closely associated cardiac events may include a first cardiac event, e.g., Q point 822 of a QRS complex, associated with a beginning of a systolic phase of a cardiac cycle and a second cardiac event 824, e.g., S1 heart sound, that follows the first cardiac event and is also associated with the systolic phase. A number of pairs of closely associated cardiac events may be detected over a number of cardiac cycles. The IMD 700 is configured to calculate the second offset period 1022 based on timing differences, or the intervals between the first cardiac event 822 and the second cardiac event 824 of each pair. The second offset period 1022 is calculated based on the intervals. The second offset period 1022 may be the average of the determined intervals, or it may be the average interval adjusted by a fixed factor, e.g., x %. For example, the second offset period 1022 may be set to 90% of the average interval.

In another configuration, delivery of the second stimulation pulse 1004 may be triggered based on diaphragm motion. To this end, the motion phase, e.g., caudal phase or cranial phase, of the diaphragm may be determined based on signals from a motion sensor 720. For example, with reference to FIGS. 7 and 10, the diaphragm motion analysis module 738 of the IMD 700 controller 702 may be configured to monitor the motion signal of the diaphragm to detect a fiducial point of the cranial phase 1010 resulting from the first stimulation pulse 1002, and output the second stimulation pulse 1004 upon such detection. The triggering fiducial point of the cranial phase may be at or near a peak or an inflection point 1024 of the cranial phase 1010.

In the case of extending the caudal phase (which is not shown in FIG. 10), the IMD 700 controller 702 may be configured to monitor the motion signal of the diaphragm to detect a fiducial point of the caudal phase 1008 resulting from the first stimulation pulse 1002, and output the second stimulation pulse upon such detection. This will prolong the caudal phase and thereby increase the duration of negative intrathoracic pressure and less pressure on the heart/vessels, thereby extending a period of better filling of the heart.

In another configuration, multiple second stimulation pulses may be delivered to extend each of the caudal phase and the cranial phase. In this configuration, a "first" second stimulation pulse may be delivered at an appropriate time after the first stimulation pulse 1002 and during the caudal phase. For example, the "first" second stimulation pulse may be delivered at the peak of the caudal phase 1008 shown in FIG. 10 to thereby extend the caudal phase. At the end of the extended caudal phase, and while the diaphragm is in a cranial phase, a "second" second stimulation pulse may be delivered at an appropriate time to extend the cranial phase.

Combined Dual-Pulse and Paired-Pulse ADS Therapy

With reference to FIGS. 8B and 10, in an accordance with another embodiment, an ADS therapy may combine the dual-pulse ADS therapy and the paired-pulse ADS therapy. To this end, a first ADS pulse 802 of a dual-pulse ADS therapy is delivered during late diastole, followed by the delivery of a second ADS pulse 804 of the dual-pulse ADS therapy during early systole. This second ADS pulse 804 also functions as a first ADS pulse 1002 of a paired-pulse ADS therapy. With reference to FIG. 10, the first ADS pulse 1002 (corresponding to the second ADS pulse 804) and a second ADS pulse 1004 are delivered during early systole.

Returning to FIG. 8B, the first ADS pulse 802 delivered during late diastole produces a corresponding transient, partial contraction 808 of the diaphragm having a caudal phase 830 and a cranial phase 832, each of normal duration. Jumping to FIG. 10, the pair of ADS pulses 1002, 1004 delivered during early systole produces a corresponding transient, partial contraction 1006 of the diaphragm having a caudal phase 1008 and an extended cranial phase 1010, 1012.

Thus, in the combined dual-pulse and paired-pulse ADS therapy, three ADS pulses are delivered per cardiac cycle. The first ADS pulse produces a normal transient, partial contraction of the diaphragm during the diastolic phase, while the second and third ADS pulses produce an extended transient, partial contraction of the diaphragm during the systolic phase having an enhanced cranial phase.

Multiple-Pulse ADS Therapy

Figure 12A:
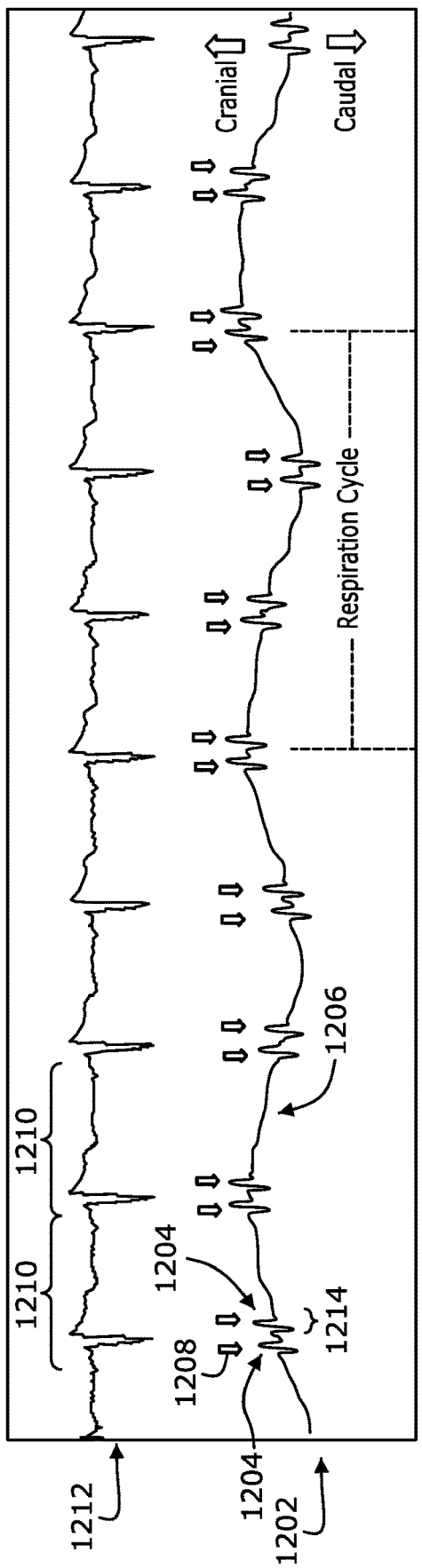
FIGS. 12A and 12B are illustrations of an ECG waveform and a diaphragmatic acceleration waveform including a series of transient, partial contractions of the diaphragm resulting from different ADS therapies, including a therapy based on FIG. 8A wherein a dual ADS pulses are delivered each cardiac cycle (FIG. 12A) and a therapy wherein a greater number of ADS pulses are delivered each cardiac cycle based on heart rate (FIG. 12B).
Figure 12B:
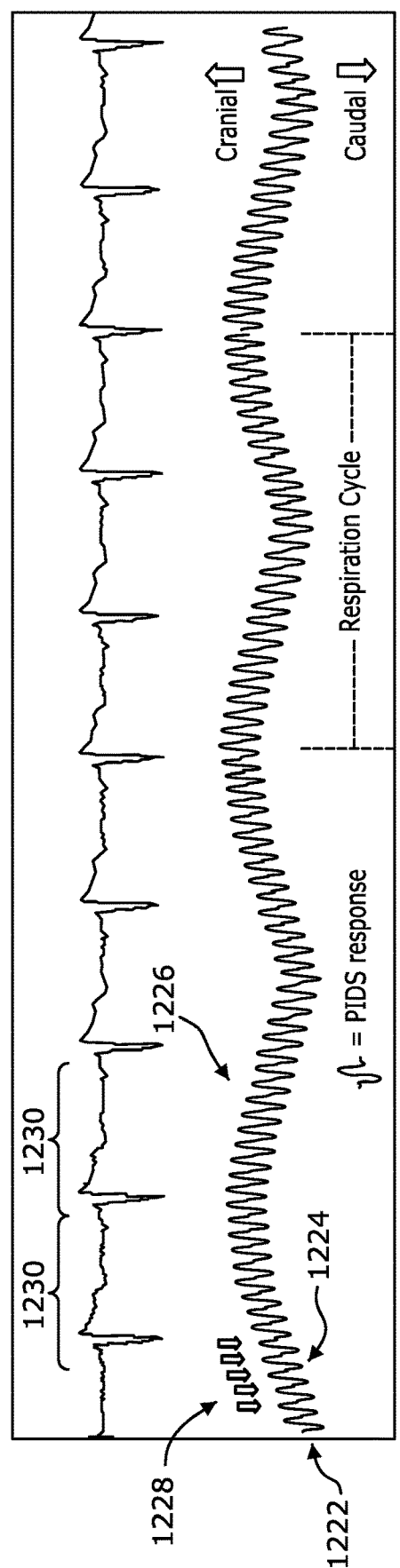

With reference to FIG. 12B, in accordance with embodiment disclosed herein, multiple, e.g., two or more, ADS pulses are delivered during a cardiac cycle based on heart rate. Prior to describing the multiple-pulse ADS therapy, reference is made to FIG. 12A for purposes of describing the theory behind multiple pulse ADS therapy. In FIG. 12A, a diaphragmatic acceleration signal 1202 includes a number of spaced apart pairs of transient, partial diaphragmatic contractions 1204 superimposed on top of an underlying respiratory signal 1206. Each pair of transient, partial diaphragmatic contractions 1204 results from the above described dual-pulse ADS therapy, by which two ADS pulses 1208 are delivered so that a pair of contractions 1204 occur during each of the cardiac cycles 1210 shown in a ECG signal 1212.

The diaphragmatic acceleration signal 1202 of FIG. 12A was captured through an animal model with a heart rate of 120 bpm, which corresponds to an RR interval of 500 msec. The duration or pulse width 1214 of each contraction 1204 is largely independent of heart rate. For example, the pulse width 1214 of a contraction 1204 does not shorten as a result of increased heart rate. In other words, diaphragmatic tone is driven by respiratory but not cardiac tone. Accordingly, the number of ADS pulses 1208 that may be delivered during a cardiac cycle 1210 in a way that results in no overlapping of contractions 1204 depends on the actual heart rate/RR interval. For example, with an RR interval of 500 msec. and a pulse width 1214 of about 100 msec., the maximum number of potentially effective transient, partial contractions 1204 would be 5. At 60 bpm (RR 1000 msec.)

the maximum number of potentially effective transient, partial contractions 1204 doubles to 10.

With reference to FIG. 12B, a diaphragmatic acceleration signal 1222 includes a continuous stream of transient, partial contractions 1224 of the diaphragm superimposed on top of an underlying respiratory signal 1226. Each of the partial contractions 1224 result from a corresponding ADS pulse 1228, where ADS pulses are delivered so that nine contractions occur during each cardiac cycle 1230. In accordance with multiple-pulse ADS therapy, the mechanical modulation, i.e., the transient, partial contraction or twitching, of the diaphragm is in a constant, sinus wave like motion. Accordingly, the portion of the diaphragm that is contracting is continuously going back and forth through the caudal phase and cranial phases but is still well synchronized to the cardiac cycle 1230.

The number of transient, partial contractions per cardiac cycle 1230, otherwise referred to as the "twitch frequency," depends on the heart rate. In one implementation, the number of ADS pulses 1228 and resulting twitches or transient, partial contractions 1224 is selected so that only full twitch cycles are present. A full twitch cycle means that the portion of the diaphragm that is contracting goes through a complete caudal phase and a complete cranial phase before a next ADS pulse 1228 is delivered. To this end, the number of ADS pulses 1228 is an integer number that is based on the heart rate range or RR interval. For example, for an RR interval in the range of 1000 msec. to 1099 msec., and assuming a twitch duration of 100 msec., the number of ADS pulses 1228 delivered per cardiac cycle 1230 is ten.

Figure 13:
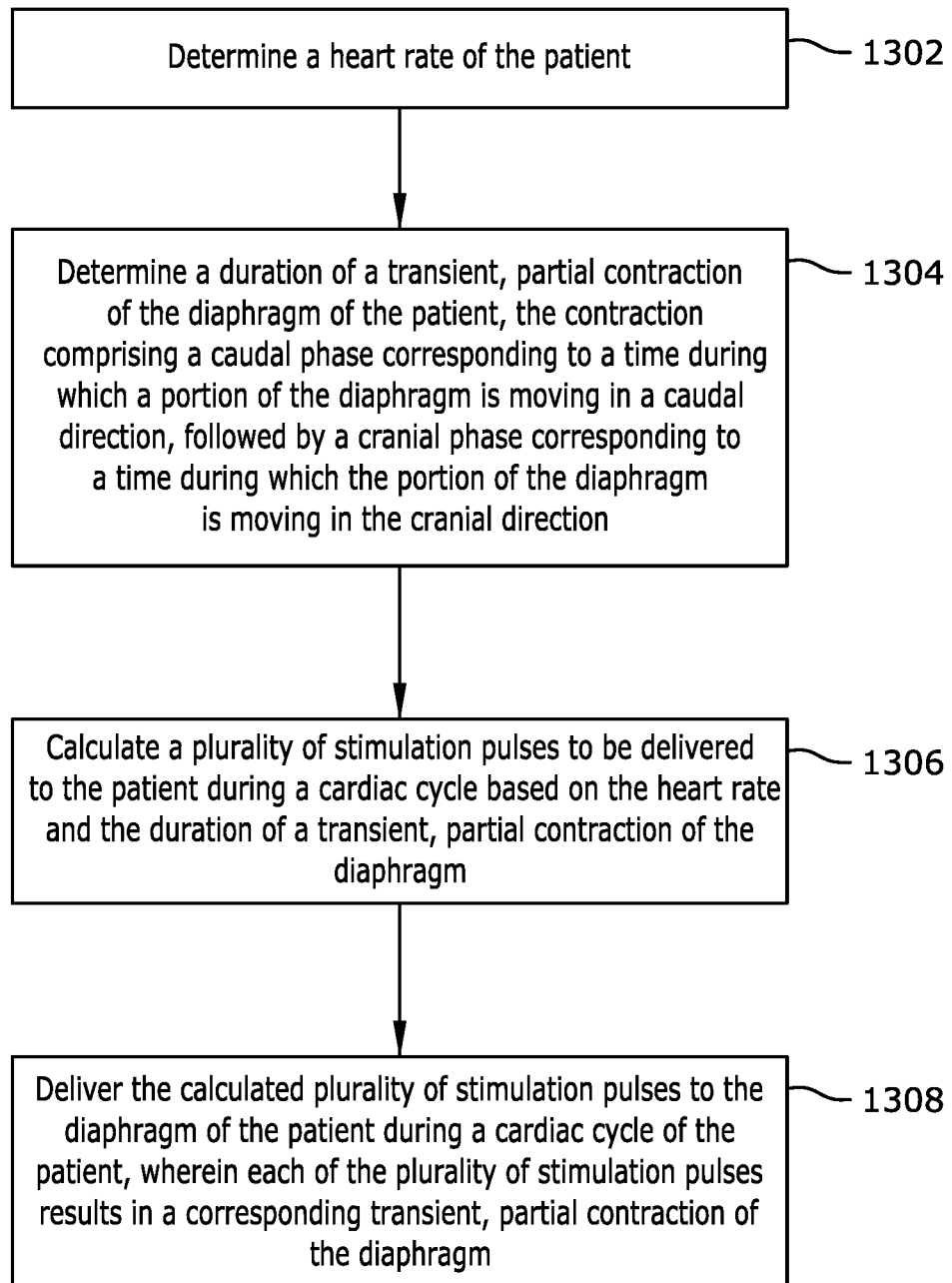
FIG. 13 is a flowchart of a method of affecting pressure in an intrathoracic cavity of a patient through delivery of multiple ADS pulses per cardiac cycle.

FIG. 13 is a flowchart of a method of affecting pressure in an intrathoracic cavity of a patient through delivery of multiple ADS pulses per cardiac cycle. The method may be performed by the IMD 700 of FIG. 7 or a similar apparatus or system. For example, the method may be performed by an apparatus having one or more electrodes 722, 724 configured for placement on or near a diaphragm and a controller 702 coupled to the one or more electrodes. The controller 702 is configured, for example, though executable program instructions stored in a memory, to perform the method described below with reference to FIG. 13. In this method, ADS pulses are delivered independent of any detected cardiac events. In other words, the delivery of multiple pulse ADS therapy is not triggered by or synchronized with a detection of a cardiac event.

At block 1302, a heart rate of the patient is determined. To this end, the controller 702 may be configured to detect a number of cardiac events over a number of corresponding cardiac cycles based on signals sensed by the one or more electrodes 722, 724 configured for placement on or near the diaphragm, or signals sensed by one or more electrodes 712, 714 configured for placement on or near the heart, or based on signals sensed by a motion sensor 716 configured for placement on or near the diaphragm or on or near a heart.

At block 1304, a duration of a transient, partial contraction of the diaphragm of the patient is determined. The partial contraction of the diaphragm includes a caudal phase corresponding to a time during which a portion of the diaphragm is moving in a caudal direction, followed by a cranial phase corresponding to a time during which the portion of the diaphragm is moving in the cranial direction. This duration may be determined based on acceleration signals sensed, for example, by a motion sensor 720 of the IMD 700 located on or near the diaphragm. As described above with reference to FIG. 7, the motion sensor 720 may be an accelerometer configured to be positioned on or near a diaphragm to sense motion of the diaphragm, and to output electrical signals representative of such motion to the diaphragm motion/heart sounds analysis module 738 of the controller 702. Alternatively, the motion sensor may be configured to be positioned in, on, or adjacent to an intrathoracic structure, e.g. heart, pericardium, great artery and vein, within the intrathoracic cavity. In this case, the motion sensor may be associated with a device configured to be implanted remote from the controller 702 and to provide signals sensed by the motion sensor to the controller through a wireless communication link.

At block 1306, the plurality of stimulation pulses to be delivered to the patient during a cardiac cycle is calculated based on the heart rate and the duration of a transient, partial contraction of the diaphragm. To this end, the controller 702 is programmed to calculate the number of ADS pulses to be delivered per cardiac cycle. For example, the number may be calculated as follows:

$$N=RR/CPW$$

where, N=the number of ADS pulses to be delivered per cardiac cycle

RR=heart rate measured as the interval between consecutive R waves

CPW=the pulse width of a transient, partial contract of the diaphragm

At block 1308, the plurality of stimulation pulses are delivered to a diaphragm of the patient during a cardiac cycle of the patient. The spacing between ADS pulses is such that each of the plurality of stimulation pulses results in a corresponding transient, partial contraction of the diaphragm.

The delivery of multiple ADS pulses per cardiac cycle may occur on a continuous basis, or may occur periodically, for a predetermined period of time. For example, the controller 702 of the IMD 700 may be programmed to turn multiple-pulse ADS therapy on once per day for a period of multiple hours, e.g., four hours. The controller 702 is also configured to continuously or periodically redetermine the heart rate and to adjust the number of ADS pulses delivered per cardiac cycle accordingly.

Electromyography (EMG) Sensing

With reference to FIG. 7, in accordance with embodiments disclosed herein, EMG sensing and analysis capability may be included in an IMD 700. The EMG sensing enables the IMD 700 to assess diaphragmatic health and/or heart failure decompensation status of the patient and to adjust ADS therapy. In addition, the EMG sensing enables the IMD 700 to detect potential IMD operational issues, e.g., impaired cardiac event sensing and detection, and to adjust IMD setting accordingly.

EMG signals may be collected by the IMD 700 through one or more EMG sensors located on the diaphragm. In one configuration an EMG sensor corresponds to a pair of electrodes that are placed on or near the diaphragm. These electrodes may be the electrodes 712, 714 of the cardiac event source 706, or the electrodes 722, 724 of the ADS therapy delivery mechanism 100, and are thus configured and located to sense cardiac electrical activity, e.g., ECG signals, as well as EMG activity. Accordingly, the signals sensed by the EMG sensor are described herein as composite ECG/EMG signals.

The therapy module 740 of an IMD 700 may be modified to include an EMG analysis module 760 that is configured to analyze composite ECG/EMG signals to assess diaphragmatic health and/or heart failure decompensation status. Such analyses may involve a comparison between characteristics, e.g., morphology, frequency content, amplitude, of EMG content of the composite ECG/EMG signals collected during ADS therapy and corresponding baseline characteristics collected prior to ADS therapy activation. The collection and comparison may occur periodically while ADS therapy is active, for example, once a day.

Figure 14A:
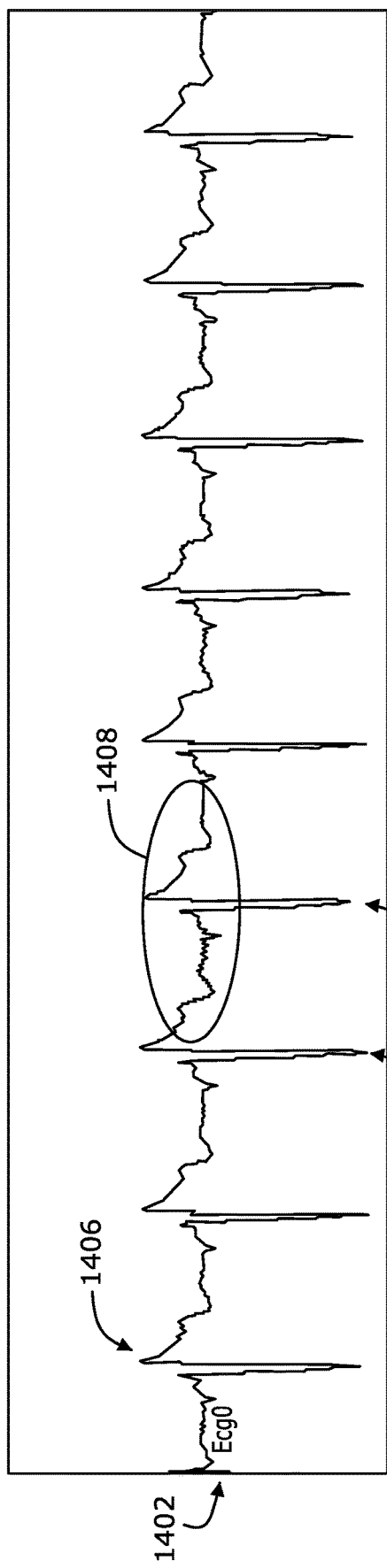
FIG. 14A is an illustration of a composite ECG/electromyography (EMG) signal corresponding to a baseline ECG/EMG signal for a patient.

FIG. 14A is an example of a baseline composite ECG/EMG signal 1402 collected after implant of an IMD 700 in a patient, but prior to activation of ADS therapy. This baseline composite ECG/EMG signal 1402 is an ECG signal 1406 that has an EMG signal superimposed therein. EMG content or EMG electrical activity of the baseline composite ECG/EMG signal 1402 appear, for example, as regions 1408 of rapid oscillations that are most notable between the R waves 1410 of the ECG signal 1406.

Figure 14B:
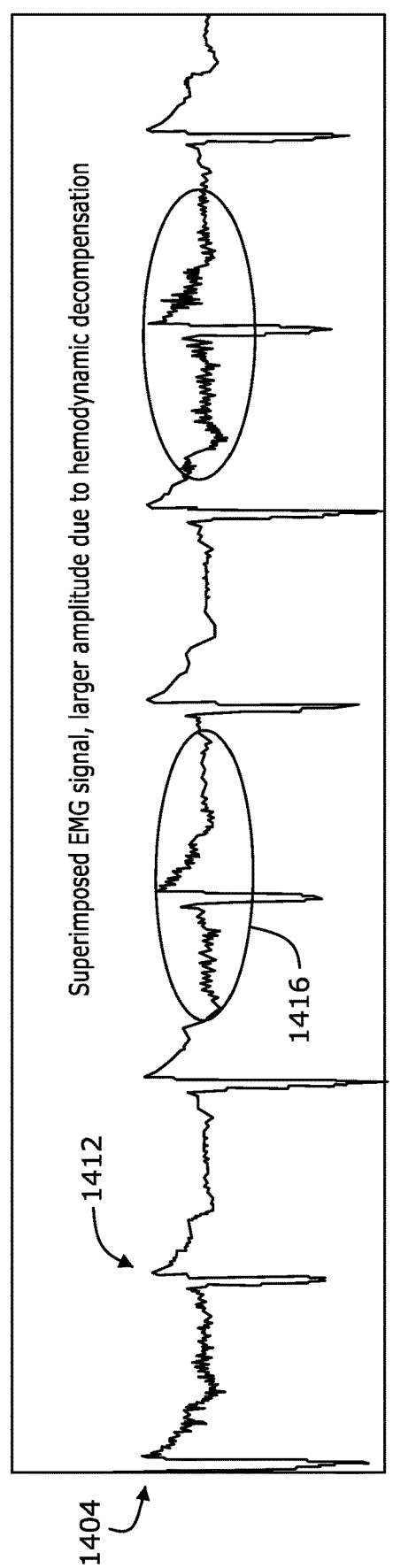
FIG. 14B is an illustration of a composite ECG/EMG signal corresponding to an ECG/EMG signal of a patient at a time after activation of ADS therapy.

FIG. 14B is an example of another composite ECG/EMG signal 1404 collected after activation of ADS therapy when the patient is hemodynamically decompensated. For example, the patient may have symptoms of shortness of breath. This composite ECG/EMG signal 1404 is an ECG signal 1412 that has an EMG signal superimposed therein. The EMG content of this composite ECG/EMG signal 1404 appear, for example, as regions 1416 of rapid oscillations. These regions 1416 of rapid oscillations have an increased amplitude relative to similar regions 1408 of the baseline composite EMG signal 1402, and serve as evidence of hemodynamic decompensation. The increase in EMG amplitude results from increased effort by the diaphragm during full diaphragmatic contraction (inspiration). The increased effort, in turn, is due to an increase in air inflow resistance in the lungs that occurs when heart failure patients start to decompensate (fluid accumulation in the lungs). As described later below, with reference to FIG. 18, these types of changes in EMG electrical activity or EMG content may be monitored overtime to assess patient health, independent of ADS therapy. In other words, a baseline composite ECG/EMG signal and subsequent ECG/EMG signals of a patient may be obtained and compared to determine patient health by a monitoring device that does not include an ADS therapy module, or one by a monitoring device that may include a deactivated ADS therapy module.

Figure 15A:
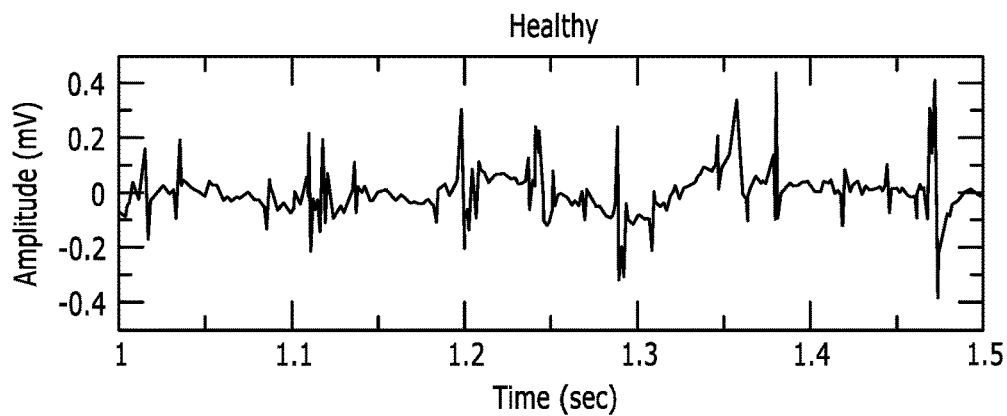
FIGS. 15A, 15B, and 15C are illustrations of pure EMG signals without any ECG component, showing an EMG signal from a healthy patient (FIG. 15A), from a patient with neuropathy (FIG. 15B), and from a patient with myopathy (FIG. 15C).
Figure 15B:
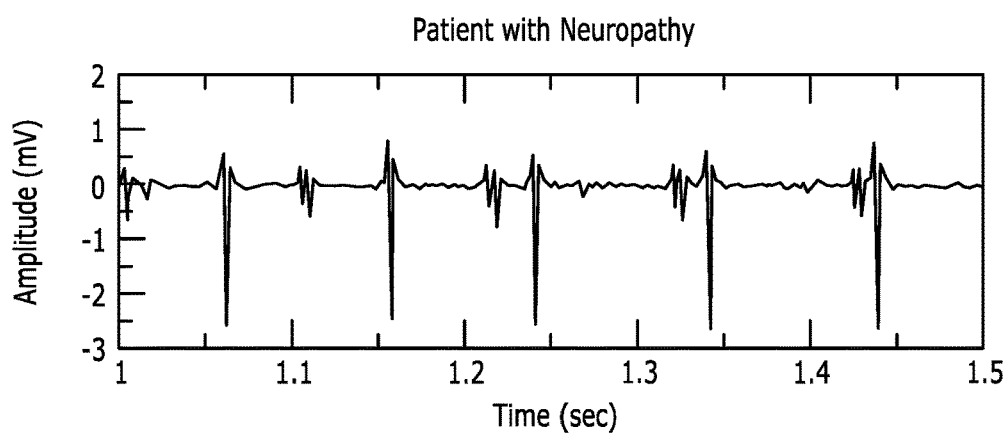
Figure 15C:
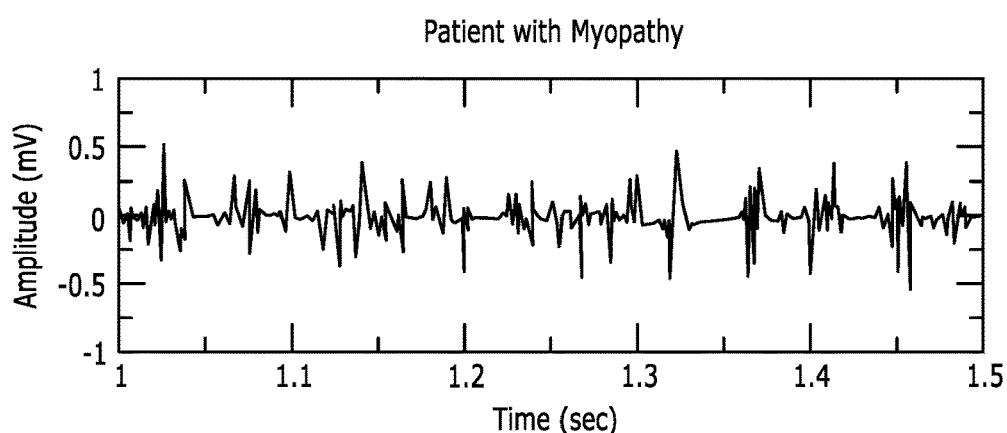

As previously mentioned, EMG signals may be used to assess the health of a patient's diaphragm and phrenic nerve. For example, the state of health of a diaphragm and phrenic nerve may be gleaned from EMG signals, such as those shown in FIGS. 15A, 15B, and 15C, which respectively illustrate pure EMG signals 1502, 1504, 1506 without any ECG component. FIG. 15A is an example EMG signal 1502 sensed from a patient with a healthy diaphragm and phrenic nerve. FIG. 15B is an example EMG signal 1504 sensed from a patient with a phrenic nerve exhibiting neuropathy. FIG. 15C is an example EMG signal 1506 sensed from a patient with a diaphragm exhibiting myopathy. Analyses of these signals would involve a time/frequency analysis for to assess morphology/pattern changes and a comparison to the last baseline, i.e. between two IPG device follow-ups.

In accordance with embodiments disclosed herein, an IMD 700 senses and stores recordings of composite ECG/EMG signals 1404 like those shown in FIG. 14B and periodically derives a measure of the EMG content of the composite ECG/EMG signal and compares it to a baseline measure that is based on composite ECG/EMG signal 1402 like that shown in FIG. 14A. For example, the IMD 700 may calculate the EMG amplitude daily and compare it to a baseline amplitude. The IMD 700 may calculate a statistical means based on a number of measures collected over a period of time, e.g., number of days, to ensure that a potential change in a measure is statistically significant, and not just a outlier measure. As an example, the IMD 700 may calculate a z-score for each individual measure and trend the z-scores.

Once the statistical measure is obtained, the IMD 700 compares the measure to the baseline measure to determine if a threshold criterion is satisfied that indicates a decrease in diaphragmatic and/or phrenic nerve health and/or heart failure decompensation status. In one example, the threshold may be considered satisfied when the statistical measure represents at least a 50% increase over the baseline measure. In another example, the threshold may be considered satisfied after a predetermined number or percentage, e.g., 8 out of 10, or 80%, of individual statistics measures represent an increase over the baseline measure.

Various type of actions may result from a forgoing determination that a threshold criterion is satisfied that indicates a decrease in diaphragmatic and/or phrenic nerve health and/or heart failure decompensation status. For example, a notification may be provided to the clinician during an IMD 700 follow-up (typically every 3 to 6 months). Alternatively, the IMD may include wireless communication capability that enables the IMD 700 to transmit relevant information to a clinician at predefined time intervals, e.g., daily, weekly, etc., or when a predefined EMG amplitude threshold has been reached.

As previously mentioned, beyond assessing diaphragmatic health and/or heart failure decompensation status of the patient, EMG signals, or more specifically, the EMG content of composite ECG/EMG signals, may be used to adjust ADS therapy. To this end, one or more stimulation parameters of the IMD 700 may be automatically adjusted to improve effectiveness of the ADS therapy. For example, the energy of the ADS pulses may be increased, e.g., pulse amplitude increased, up to a predefined value which still allows the ADS pulses to be imperceptible to the patient. Such a predefined value may be determined post IMD implant through threshold/symptoms testing when patient in conscious. In a case of patient decompensation, the fluid accumulation could also lead to a wet diaphragm requiring more stimulation energy for ADS therapy to be effective. In another example, the offset period or delay period between detected cardiac events and ADS pulse delivery may be adjusted to account for the effect of heart failure decompensation on cardiac rhythm. To this end, the timing of cardiac events in ECG content in composite ECG/EMG signals may be analyzed over time, e.g., days, to determine a new offset period or delay period for ADS therapy.

In some cases, composite ECG/EMG signals may also be used to automatically turn ADS therapy off. For example, if the EMG noise amplitude in a signal increases to a level that impairs cardiac event sensing, e.g., R wave detection, it could impact the consistency and synchronicity of ADS pulse delivery to the cardiac cycle, hence leading to an ineffective ADS therapy. To address this issue, in one configuration the IMD 700 may be configured to sense consistency of R wave sensing, and deactivate ADS therapy for as long as a consistency criterion is fulfilled. A consistency criterion may include a measure of variability of detected R wave timing (ventricular sense events outside of the refractory period) that exceeds a predetermined physiologic threshold or other statistical analysis criteria based on the IMD's sensing/stimulation history. In another configuration, the IMD 700 may be configured to sense the signal-to-noise ratio (SNR), i.e., R wave amplitude versus EMG amplitude in a composite ECG/EMG signal, and deactivate ADS therapy for as long as a certain SNR criterion is fulfilled. A SNR criterion may include a measure of SNR that fails to exceed a threshold SNR. For example, the SNR criterion may be set to 2:1, thus requiring the R wave amplitude to be at least twice that of the EMG amplitude. Otherwise, ADS therapy is deactivated. In either configuration, deactivation of ADS therapy may be accompanied by a notification to the clinician.

As previously mentioned, composite ECG/EMG signals may also be used to detect potential IMD operational issues. To this end, one or more sensing parameters of the IMD 700 may be adjusted when the EMG noise amplitude impacts the ability of the IMD to reliably sense occurrences of relevant cardiac events, e.g., ECG features, such as an R wave, detections of which are relied on to deliver effective ADS therapy. If the IMD 700 detects impaired R wave sensing, i.e. through consistency of detected R wave timing (ventricular sense events outside of the refractory period), the IMD may decrease the sensitivity setting for the sensing channel until the sensing returns to the consistency it had at baseline, prior to the EMG amplitude increase. If the R wave amplitude is small and the EMG noise drastically increases, it might not be possible to find a suitable sensitivity setting. In that case, the IMD 700 may automatically temporarily suspend the ADS therapy until the EMG noise is reduced and/or notify the clinician.

With reference to FIGS. 7, 16A, 16B, 16C, the controller 702 of an IMD 700 may include a ECG/EMG filter module 762 configured to affect a composite ECG/EMG signal 1602, 1604, 1606 captured by one or more electrodes 712, 714, 722, 724 on or near the diaphragm. In one configuration, the ECG/EMG filter module 762 may be set to capture one or more different frequency ranges or bands of the ECG component and EMG component of the composite ECG/EMG signals 1602, 1604, 1606 to selectively enable better detection and analysis of one of the EMG content or the ECG content.

Figure 16A:
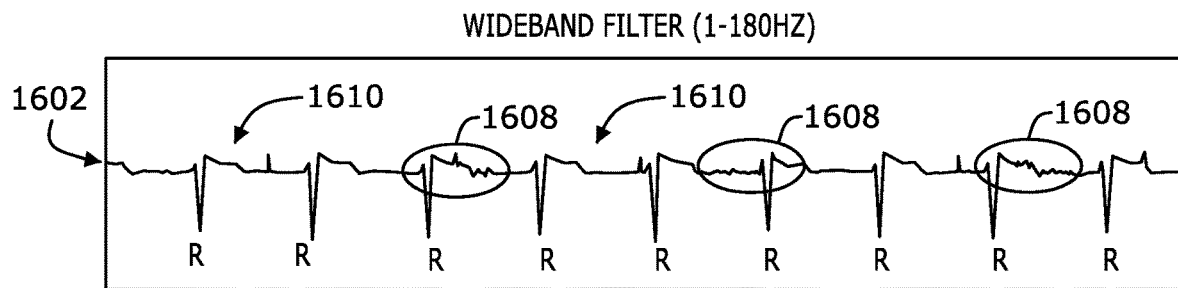
FIGS. 16A, 16B and 16C are illustrations of composite ECG/EMG signals obtained through different signal filter settings, including a first wideband filter (FIG. 16A), a second wideband filter (FIG. 16B), and a narrowband filter (FIG. 16C).
Figure 16B:
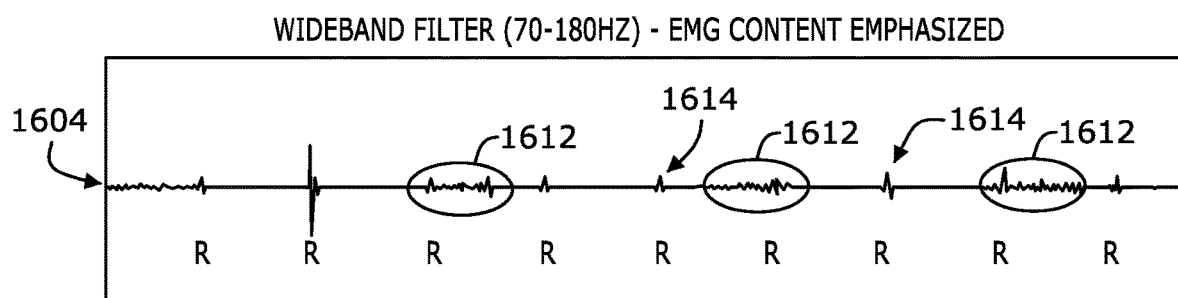
Figure 16C:
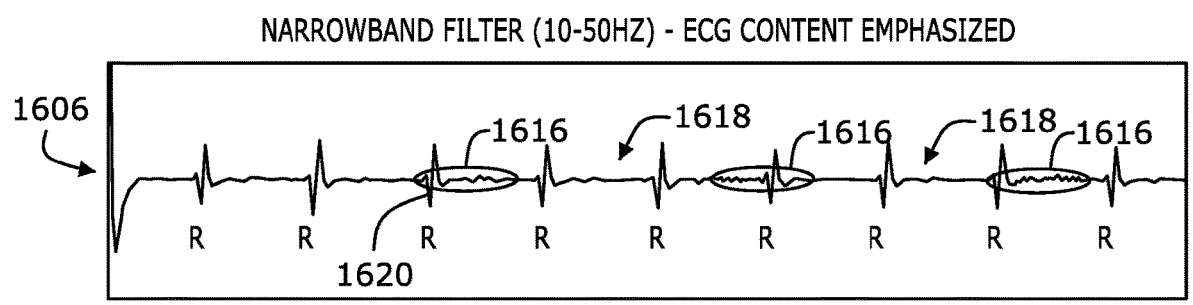

The composite ECG/EMG signal 1602 of FIG. 16A is captured when the filter is set to a wideband state (1-180 Hz), and includes EMG noise 1608 superimposed on a far-field ECG signals 1610. The composite ECG/EMG signal 1604 of FIG. 16B is captured when the filter is set to a wideband (70-180 Hz) state. This filter state favors EMG content 1612 over ECG content 1614 and allows the controller 702 of the IMD 700 to better sense and assess the EMG signal characteristics including amplitude. The composite ECG/EMG signal 1606 of FIG. 16C is captured when the filter is set to a narrowband (10-50 Hz) state. This filter state favors ECG content 1616 over EMG content 1618. This filter state attenuates the EMG content and allows the IMD to better sense and assess the ECG content, e.g., R waves.

Figure 17:
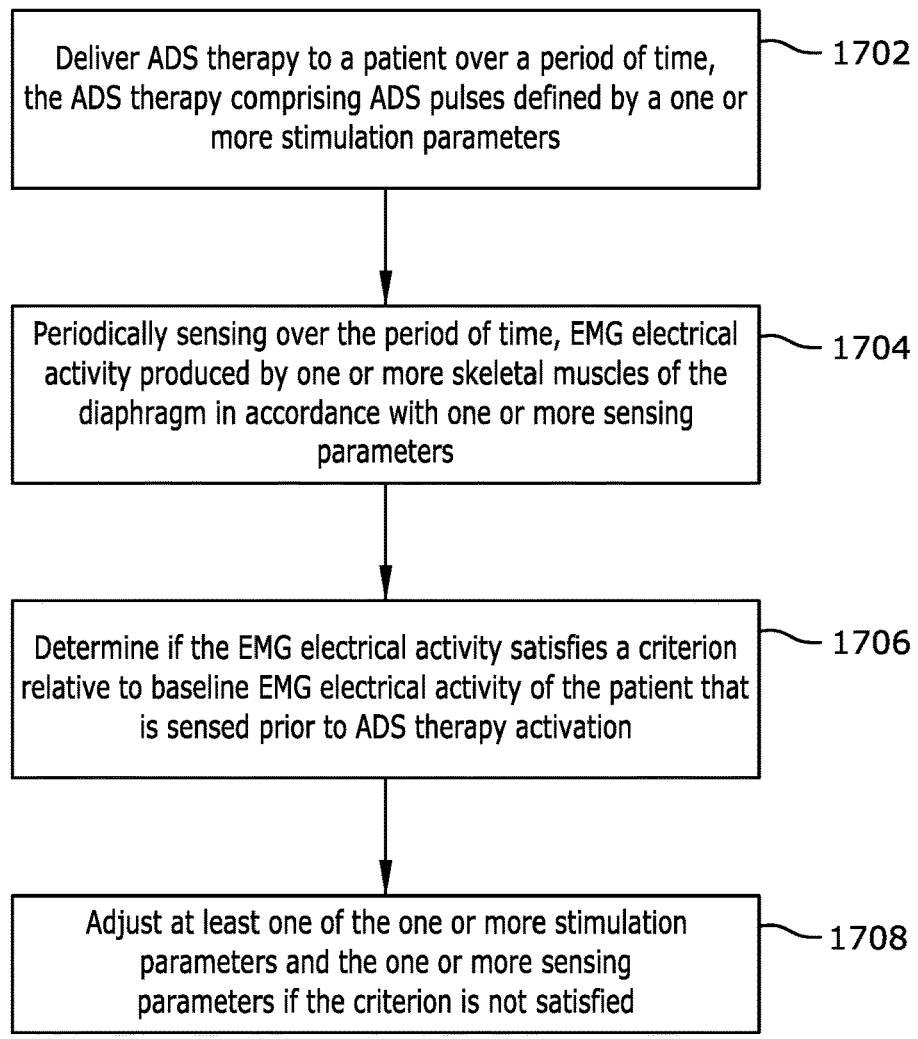
FIG. 17 is a flowchart of a method of modifying sensing and/or stimulation parameters for an apparatus that affects pressure in an intrathoracic cavity of a patient through delivery of ADS therapy.

FIG. 17 is a flowchart of a method of modifying sensing and/or stimulation parameters for an apparatus that affects pressure in an intrathoracic cavity of a patient through delivery of ADS. The method may be performed by the IMD 700 of FIG. 7 or a similar apparatus or system. For example, the method may be performed by an apparatus having one or more electrodes 722, 724 configured for placement on or near a diaphragm and a controller 702 coupled to the one or more electrodes. The controller 702 is configured, for example, though executable program instructions stored in a memory, to perform the method described below with reference to FIG. 17.

In this embodiment, the IMD 700 further includes a ECG/EMG filter module 762 that enables a composite ECG/EMG signal received from an input sensing channel provided by the electrodes 712, 714 to be subjected to two types of filtering, including a filtering that enables better EMG feature detection, and a filtering that enables better ECG feature, e.g., R wave, detection. In one implementation, composite ECG/EMG signals from the sensing channel are directed along two filter paths within the ECG/EMG filter module 762, each having a respective filter. The first filter is a narrowband filter configured to attenuate the EMG content to thereby emphasize the ECG content for cardiac event sensing detection (see FIG. 16C, described below). The second filter is a wideband filter configured to output a signal that contains both ECG content and an EMG content (see FIG. 16B, described below). The latter is used to assess the EMG amplitude through different means, i.e. simple SNR analysis up to more sophisticated frequency or even wavelet template matching, as described further below.

Returning to FIG. 17, at block 1702, ADS therapy in the form of ADS pulses defined by one or more stimulation parameters, is delivered to the patient over a period of time. To this end, the IMD 700 senses a composite ECG/EMG signal 1404 through an input sensing channel, such as a channel provided by electrodes 712, 714. The IMD 700 filters the composite ECG/EMG signal 1404 to better enable detection of ECG electrical activity over EMG electrical activity. For example, the composite ECG/EMG signal 1404 may be filtered to a narrowband (10-50 Hz) state by a ECG/EMG filter module 762 to produce a filtered composite ECG/EMG signal 1606 like the one shown in FIG. 16C. The IMD 700 then processes the filtered composite ECG/EMG signal 1606 to detect an electrical cardiac event in the ECG content 1616 present in the signal. For example, the IMD 700 may detect one or more ECG features, e.g., R waves 1620. The IMD 700 then outputs one or more ADS pulses responsive to the detected electrical cardiac event in accordance with one or more of the ADS therapies described above.

At block 1704, EMG electrical activity produced by one or more skeletal muscles of the diaphragm is periodically sensed over the period of time in accordance with one or more sensing parameters. The one or more sensing parameters of the IMD, which are initially set and programmed by the clinician, may include: 1) a sensing sensitivity (measured in millivolts) which is a reference voltage in a signal comparator to facilitate the detection of cardiac event, e.g., ECG fiducial points, such as R wave detections, and 2) timing windows that include a) blanking intervals (measured in msec.) which are windows where the IMD is blinded to the ECG signal for the purpose of ECG fiducial detections, and b) refractory periods (measured in msec.) which are windows where the IMD senses the ECG signal and detects ECG fiducials, but does not use those detections for the purpose of delivering ADS pulses to the diaphragm. "Blinded" means that the sensing channel of the IMD is turned off. This is necessary after an ADS pulse is delivered to the diaphragm as resulting afterpotential would overdrive the sensing amplifier of the IMD sensing channel during the stimulus. Accordingly, the sensing channel of the IMD gets "blanked" until the afterpotentials are small enough to not cause a problem. The duration of the blanking interval is typically determined by the clinician.

Continuing with block 1704, the IMD 700 senses a composite ECG/EMG signal 1404 through an input sensing channel, such as a channel provided by electrodes 712, 714. The IMD 700 filters the composite ECG/EMG signal 1404 to better enable detection of EMG electrical activity over ECG electrical activity. For example, the composite ECG/EMG signal 1404 may be filtered to a wideband (70-180 Hz) state by a ECG/EMG filter module 762 to produce a filtered composite ECG/EMG signal 1604 like the one shown in FIG. 16B. The composite ECG/EMG signal 1604 is then processed to detect electrical activity features in the EMG content 1612 of the signal. For example, the IMD 700 may detect one or more of EMG signal amplitude, EMG signal frequency, or EMG signal morphology.

At block 1706, the IMD 700 determines if the EMG electrical activity satisfies a criterion relative to baseline EMG electrical activity of the patient that is sensed prior to ADS therapy activation. To this end, the IMD 700 may compare a morphology characteristic, e.g., R wave width, of the EMG content in the filtered composite ECG/EMG signal 1604 (see FIG. 16B) with a baseline of the morphology characteristic. The IMD 700 may compare a frequency characteristic, e.g., high frequency content, of the EMG content in the filtered composite ECG/EMG signal 1604 (see FIG. 16B) with a baseline of the frequency characteristic. The IMD 700 may compare an amplitude characteristic of the EMG content in the filtered composite ECG/EMG signal 1604 (see FIG. 16B) with a baseline of the amplitude characteristic.

At block 1708, at least one of a stimulation parameter and a sensing parameter is adjusted if the criterion is not satisfied. For example, in the case of a morphology comparison in block 1706, an increase in the width of the R wave due to higher EMG signal strength in the composite ECG/EMG signal, e.g., the wideband filtered signal 1604 shown in FIG. 16B, relative to a baseline could trigger an adjustment of sensing parameter, e.g., decrease the sensitivity setting (increase in reference voltage). In the case of a frequency characteristic comparison in block 1706, an increase in higher frequency content when looking at a spectrogram of the composite ECG/EMG signal, e.g., the wideband filtered signal 1604 shown in FIG. 16B, relative to a baseline could trigger an adjustment of sensing parameter, e.g., decrease the sensitivity setting (increase in reference voltage). In the case of an amplitude comparison in block 1706, an increase in amplitude of the composite ECG/EMG signal, e.g., the wideband filtered signal 1604 shown in FIG. 16B, within a time period in the cardiac cycle, which does not contain any prominent ECG fiducial, i.e. not around the R wave, P wave of T wave, relative to a baseline could trigger an adjustment of sensing parameter, e.g., decrease the sensitivity setting (increase in reference voltage).

In other examples regarding sensing parameters, the sensing sensitivity of the input sensing channel may be reduced to lower the presence of EMG content in a composite ECG/EMG signal to thereby reduce the impact of the EMG signal on the ability of the IMD 700 to detect R waves. Regarding stimulation parameters, the stimulation energy of ADS pulse may be increased or the offset period of the ADS pulse may be adjusted to improve the effectiveness of the therapy. The IMD 700 may suspend the delivering of ADS therapy while it is adjusting at least one of the stimulation parameters and the sensing parameters.

Stimulation Parameters

The ADS therapy delivered by the IMD is defined by stimulation parameters that include: 1) one or more pulse parameters having a value or setting selected to define a stimulation pulse that induces a transient, partial contraction of the diaphragm, and 2) a timing parameter that controls the timing of the delivery of one or more ADS pulses. The pulse parameters may include, for example, a pulse waveform type, a pulse amplitude, a pulse duration, and a pulse polarity. The timing parameter may include one or more offset periods or delay periods that defines a time between a detected cardiac event and a delivery of an electrical stimulation pulse.

With respect to the pulse parameters, as previously described, a transient, partial contraction of the diaphragm typically entails a very short (only a few tens of milliseconds) pulse-like, biphasic (singular-caudal followed by singular-cranial) asymptomatic motion of the diaphragm. The IMD 700, including in particular the therapy module 740, is configured to generate stimulation pulses that result in very short, biphasic asymptomatic motion of the diaphragm. To this end, the therapy module 740 may be configured to select a setting of square, sinusoidal, triangular, or sawtooth for the pulse waveform type, and to select a setting of positive or negative for the pulse polarity. The therapy module 740 may be further configured to select a value for the pulse amplitude that is between 0.0 volts and 7.5 volts, and to select a value for the pulse duration that is between 0.0 milliseconds and 5 milliseconds.

Regarding the timing parameter, the therapy module 740 may be configured to determine one or more offset periods or delay periods. As previously described, the delay period may be based on the time between successive detected cardiac events. For example, the EGM analysis module 732 of the cardiac signal module 728 may be configured to detect ventricular events, e.g., R waves, and to output such detections to the therapy module 740. The cardiac-event analysis module 742 may process the detected ventricular events to determine a statistical measure of time between a number of pairs of successive ventricular events. The cardiac-event analysis module 742 may then determine a delay period based on the statistical measure and an offset relative to the statistical measure, and control the pulse generator 746 to output ADS pulses based on the determined offset period or delay period.

Initial selection of pulse parameter settings and values and the timing parameter by the therapy module 740 may be performed by a physician through an external device, e.g., a programmer. In this case, the external device provides selection commands to the therapy module 740 through a wireless communication link, and the therapy module selects the pulse parameters and timing parameter in accordance with the commands. Alternatively, selection of pulse parameter settings and values and the timing parameter by the therapy module 740 may be automated.

Sensing Parameters

As previously mentioned, the sensing parameters of the IMD 700 may include: 1) a sensing sensitivity, which is a reference voltage in a signal comparator to facilitate the detection of cardiac event, e.g., ECG fiducial points, such as R wave detections, and 2) timing windows that include a) a blanking interval, which is a portion of a cardiac cycle during which the IMD is blinded to the ECG signal for the purpose of ECG fiducial detections, and b) a refractory period which is a portion of a cardiac cycle during which the IMD senses the ECG signal and analyzes the ECG signal to detect ECG fiducials, but does not use those detections for the purpose of delivering ADS pulses to the diaphragm.

Regarding the sensitivity parameter, this parameter is used to set the value of a reference voltage, e.g., a threshold voltage, that is compared with the varying amplitude of the EMG content within composite ECG/EMG signals. A higher sensitivity voltage means that the IMD 700 is less sensitive to the ECG content within the composite ECG/EMG signals for the purpose of detecting cardiac events, e.g., fiducial points corresponding to R waves. If the reference voltage is too high and larger than the ECG content, then no fiducial points, e.g., R waves, can be detected. This condition is referred to as undersensing. If the reference voltage is much lower than the SNR, then inadequate detection of fiducial points, e.g., R-waves, can occur. This condition is referred to as oversensing. When the EMG content within a composite ECG/EMG signal becomes larger due to diaphragmatic stress (represented by noise in the EMG signal, such as shown in FIG. 14B), the SNR measured by the IMD 700 goes down relative to a baseline SNR, and the likelihood of oversensing goes up. As a counter measure, upon detection of an SNR indicative of oversensing the IMD 700 may automatically decrease the sensing sensitivity setting by increasing the reference voltage. Similarly, the IMD 700 may monitor the consistency of R wave detections over time to detect oversensing and adjust the sensing parameter by decreasing sensing sensitivity.

In one configuration, the IMD 700 may include a sensitivity voltage parameter having a value or setting, e.g., between 0.1 millivolts and 10 millivolts, selected to set a reference voltage to compare with ECG content in a filtered ECG/EMG composite signal and to facilitate the detection of cardiac events, e.g., R waves or other fiducials, in the ECG signal as a timing reference for the delivery of ADS pulses. For example, the sensitivity voltage of the previously described narrowband filter of the ECG/EMG filter module 762 may be adjusted to produce a composite ECG/EMG signal 1606 with ECG content having well-pronounced R waves 1620 for cardiac event sensing detection purposes (see FIG. 16C). Or, in other words, the reference voltage may be increased until the SNR increases to an appropriate level, i.e., a level that does not fulfill the SNR criterion described above, or the R wave consistency measure increases to an appropriate level, i.e., a level that does not fulfill the consistency criterion described above.

Regarding the timing window parameters, these parameters, e.g., blanking intervals and refractory periods, generally correspond to time periods in the cardiac cycle in which therapy relevant ECG fiducial points are unlikely to be present and/or where artifacts like signal noise and ADS pulse afterpotentials could lead to false detections. The blanking intervals and refractory periods are set by the clinician to increase the specificity of cardiac event detections, e.g., the fiducial point detections, such as R waves, with which ADS pulse delivery is synchronized. The blanking intervals and refractory periods allow the IMD 700 to only use certain time periods in the cardiac cycle which have a high likelihood to contain the ECG fiducial points meant to be detected for purposes of delivering ADS therapy. During these certain time periods, the signal analysis performed by the IMD 700 includes signal analysis for detecting the presence of cardiac events, e.g., R waves, or other ECG fiducials, classifying each such detected cardiac event as a valid cardiac event or a non-valid event, e.g., noise (events detected during absolute refractory times), and delivering ADS pulses accordingly. In essence, the blanking interval and refractory period drive the action taken by the IMD state machine, i.e. if and when a signal threshold crossing (sensing event) leads to a diaphragm stimulus. The signal analyzed by the IMD 700 for purposes of detecting cardiac events may correspond to the narrowband filtered composite ECG/EMG signal 1606 shown in FIG. 16C.

Blanking intervals, which are intervals during which the IMD is blinded to the composite ECG/EMG signal for the purpose of ECG fiducial detections, are applied in time periods with high likelihood of containing artifacts. For example, a blanking interval may correspond to a period of time, e.g., 20 msec., after delivery of an ADS pulse to the diaphragm during which corresponding afterpotentials may impact the ECG content of sensed composite ECG/EMG signals and to lead to detections of non-valid cardiac events. These blanking intervals are not changed due to the detection of EMG noise.

Refractory periods allow the detection of ECG fiducials, but such detections are not used to trigger delivery of ADS pulses. The signal analysis performed by the IMD during refractory periods includes signal analysis for detecting the presence of cardiac events or conditions for which ADS therapy delivery should not occur, e.g., certain heart rates, including elevated heart rates at or near an upper tracking rate programmed in the IMD 700. The signal analyzed by the IMD 700 for purposes of detecting cardiac events may correspond to the narrowband filtered composite ECG/EMG signal 1606 shown in FIG. 16C.

A refractory period may correspond to a period of time, e.g., 400 msec., after the detection of an R wave or the delivery of cardiac pacing pulse, in the case of a heart that is subjected to cardiac pacing therapy. In the case of sensed composite ECG/EMG signals having increased EMG noise, which would lead to detection of non-valid cardiac event, e.g., false R wave detections, and thereby to falsely timed ADS pulse delivery, the IMD 700 may adjust the refractory period by increasing its length. For example, the IMD 700 may be configured to sense the SNR, i.e., R wave amplitude versus EMG amplitude, and increase the refractory period when a certain SNR criterion is fulfilled. As previously described, a SNR criterion may include a measure of SNR that fails to exceed a threshold SNR. For example, the SNR criterion may be set to 2:1, thus requiring the R wave amplitude to be at least twice that of the EMG amplitude. Similarly, the IMD 700 may monitor the consistency of R wave detections over time to detect oversensing and adjust the refractory period by increasing it. In either case, the refractory period may be increased up to a point where the IMD 700 does not deliver any ADS pulses as the prolonged refractory period suppress any cardiac event detections that trigger ADS pulse delivery, thereby effectively disabling ADS therapy.

Monitoring Device

In another embodiment, an IMD for monitoring patient health may be include components and modules for sensing and analyzing the ECG content and EMG content of composite ECG/EMG signals similar to those described with respect to FIG. 7. This IMD may be configured to only monitor composite ECG/EMG signals to determine diaphragm/patient health. In other words, the IMD does not include an ADS therapy module. Alternatively, this IMD may have ADS therapy capabilities that are turned off. In either case, in addition to its monitoring capabilities, this IMD may be configured to store and/or transmit the data corresponding to signal sensing and analysis to a clinician for later interpretation by the clinician.

Figure 18:
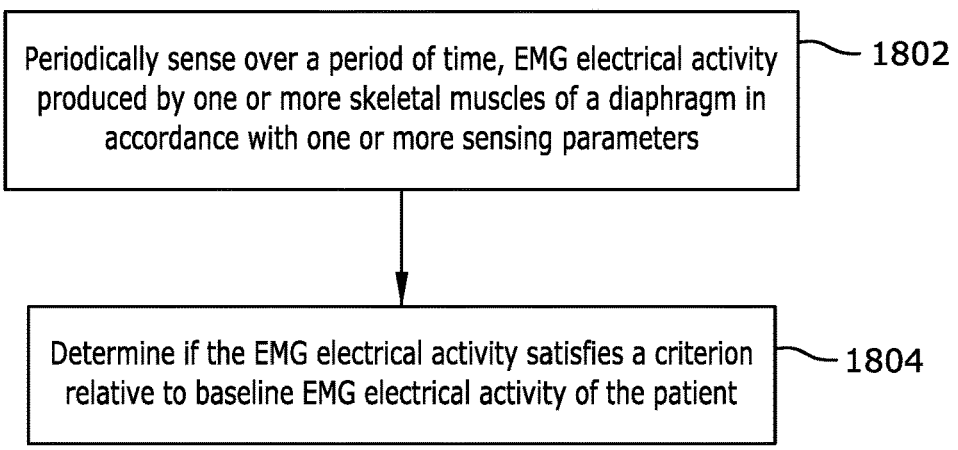
FIG. 18 is a flowchart of a method of monitoring patient health based on EMG electrical activity of the diaphragm.

FIG. 18 is a flowchart of a method of monitoring patient health. The method may be performed by an IMD similar to the IMD 700 of FIG. 7, but without ADS therapy capability. For example, the method may be performed by an apparatus having one or more electrodes 712, 714 configured for placement on or near a diaphragm and a controller 702 coupled to the one or more electrodes. The controller 702 may include the cardiac signal module 728, the pressure signal module 730, the EMG analysis module 760, the memory subsystem 748, the communication subsystem 750, the power supply 752, and the clock supply 754. The controller 702 is configured, for example, though executable program instructions stored in a memory, to perform the method described below with reference to FIG. 18.

At block 1802, EMG electrical activity produced by one or more skeletal muscles of the diaphragm is periodically sensed over the period of time. To this end, the IMD 700 senses a composite ECG/EMG signal 1404 through an input sensing channel, such as a channel provided by electrodes 712, 714. The IMD 700 filters the composite ECG/EMG signal 1404 to better enable detection of EMG electrical activity over ECG electrical activity. For example, the composite ECG/EMG signal 1404 may be filtered to a wideband (70-180 Hz) state by a ECG/EMG filter module 762 to produce a filtered composite ECG/EMG signal 1604 like the one shown in FIG. 16B. The composite ECG/EMG signal 1604 is then processed to detect EMG signal features in the EMG content 1612 present in the signal. For example, the IMD 700 may detect one or more of EMG signal amplitude, EMG signal frequency, or EMG signal morphology.

At block 1804, the IMD 700 determines if the EMG electrical activity satisfies a criterion relative to baseline EMG electrical activity of the patient. To this end, the IMD 700 may compare a morphology characteristic, e.g., R wave width, of the EMG content in the filtered composite ECG/EMG signal 1604 (see FIG. 16B) with a baseline of the morphology characteristic. The IMD 700 may compare a frequency characteristic, e.g., high frequency content, of the EMG content in the filtered composite ECG/EMG signal 1604 (see FIG. 16B) with a baseline of the frequency characteristic. The IMD 700 may compare an amplitude characteristic of the EMG content in the filtered composite ECG/EMG signal 1604 (see FIG. 16B) with a baseline of the amplitude characteristic.

The criterion corresponds to a deviation indicative of a change in patient health. For example, in the case of a morphology comparison, a threshold increase in the width of the R wave present in a wideband filtered composite ECG/EMG signal (such as shown in FIG. 16B) relative to a baseline R wave width may be considered to correspond to a decline in patient health. In the case of a frequency characteristic, a threshold increase in higher frequency content when looking at a spectrogram of a wideband filtered composite ECG/EMG signal (such as shown in FIG. 16B) relative to the same frequency content in a baseline may be considered to correspond to a decline in patient health. In the case of an amplitude comparison, a threshold increase in amplitude of the EMG content 1612 present in a wideband filtered composite ECG/EMG signal (such as shown in FIG. 16B) within a time period in the cardiac cycle, relative to the same amplitude within the same time period of a cardiac cycle of a baseline may be considered to correspond to a decline in patient health. A threshold increase may be a predetermine amount or percentage increase in the relative measure.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An apparatus for affecting pressure in an intrathoracic cavity of a patient, the apparatus comprising:
   one or more electrodes configured for placement on or near a diaphragm;
   a controller coupled to the one or more electrodes, and configured to:
      deliver a single diastolic stimulation pulse to the diaphragm of the patient during a diastolic phase of a cardiac cycle of the patient by being further configured to:
         detect an occurrence of a first cardiac event, and
         deliver the single diastolic stimulation pulse at or near the end of a diastolic offset period from the detected occurrence of a first cardiac event that places the delivery of the single diastolic stimulation pulse at a latter part of diastole of the cardiac cycle; and
      deliver a single systolic stimulation pulse to the diaphragm during a systolic phase of the cardiac cycle by being further configured to:
         detect an occurrence of a second cardiac event, and
         deliver the single systolic stimulation pulse at or near the end of a systolic offset period from the detected occurrence of a second cardiac event that places the delivery of the single systolic stimulation pulse at an early part of systole of the cardiac cycle,
      wherein each of the single diastolic stimulation pulse and the single systolic stimulation pulse results in an asymptomatic, transient, partial contraction of the diaphragm.

2. The apparatus of claim 1, wherein the controller is further configured to determine the diastolic offset period by being further configured to:
   detect, over a plurality of cardiac cycles, a time of occurrence of: a) the first cardiac event, b) one of an onset of an atrial event and an offset of a first ventricular event, and c) an onset of a second ventricular event that follows the onset of the atrial event or the onset of the first ventricular event; and
   process the respective times of occurrences to calculate a period of time from the first cardiac events to a time between: a) either of an onset of an atrial event or an offset of a first ventricular event, and b) an onset of a second ventricular event that follows the onset of the atrial event and the onset of the first ventricular event, wherein the period of time corresponds to the diastolic offset period.

3. The apparatus of claim 2, wherein:
   each of the onset of an atrial event and the offset of a first ventricular event correspond to a detected P wave, and
   the onset of a second ventricular event corresponds to a detected Q point in a QRS complex, or a detected S1 heart sound.

4. The apparatus of claim 1, wherein the controller is further configured to determine the systolic offset period by being further configured to:
   detect, over a plurality of cardiac cycles, a time of occurrence of: a) the second cardiac event, b) one of an onset of electrical systole and an onset of mechanical systole, and c) one of an offset of electrical systole and an offset of mechanical systole; and process the respective times of occurrences to calculate a period of time from the second cardiac events to a time between: a) either of an onset of electrical systole or an onset of mechanical systole, and b) either of an offset of electrical systole or an offset of mechanical systole, wherein the period of time corresponds to the systolic offset period.

5. The apparatus of claim 4, wherein:

an onset of electrical systole corresponds to a detected Q point in a QRS complex, and an onset of mechanical systole corresponds to a detected S1 hear sound, and an offset of electrical systole corresponds to a detected T wave, and an offset of mechanical systole corresponds to a detected S2 heart sound.

6. The apparatus of claim 1, wherein the first cardiac event and the second cardiac event are a same cardiac event type in consecutive cardiac cycles, the same cardiac event type corresponding to one of an electrical event and a mechanical event.

7. The apparatus of claim 1, wherein the first cardiac event and the second cardiac event are different cardiac events in a same cardiac cycle, each of the different cardiac events corresponding to one of an electrical event and a mechanical event.

8. The apparatus of claim 1, wherein the controller is configured to detect at least one of the occurrence of a first cardiac event and the occurrence of a second cardiac event based on signals sensed by the one or more electrodes configured for placement on or near the diaphragm.

9. The apparatus of claim 1, further comprising one or more electrodes configured for placement on or near a heart, wherein the controller is configured to detect at least one of the occurrence of a first cardiac event and the occurrence of a second cardiac event based on signals sensed by one or more electrodes configured for placement on or near the heart.

10. The apparatus of claim 1, further comprising a motion sensor configured for placement on or near the diaphragm or on or near a heart, wherein the controller is configured to detect at least one of the occurrence of a first cardiac event and the occurrence of a second cardiac event based on signals sensed by the motion sensor.

11. A method of affecting pressure in an intrathoracic cavity of a patient, the method comprising:

delivering a single diastolic stimulation pulse to a diaphragm of the patient during a diastolic phase of a cardiac cycle of the patient, wherein delivering the single diastolic stimulation pulse comprises:

detecting an occurrence of a first cardiac event, and delivering the single diastolic stimulation pulse at or near the end of a diastolic offset period from the detected occurrence of a first cardiac event that places the delivery of the single diastolic stimulation pulse at a latter part of diastole of the cardiac cycle; and delivering a single systolic stimulation pulse to the diaphragm during a systolic phase of the cardiac cycle, wherein delivering the single systolic stimulation pulse comprises:

detecting an occurrence of a second cardiac event; and delivering the single systolic stimulation pulse at or near the end of a systolic offset period from the detected occurrence of a second cardiac event that places the delivery of the single systolic stimulation pulse at an early part of systole of the cardiac cycle, wherein each of the single diastolic stimulation pulse and the single systolic stimulation pulse results in an asymptomatic, transient, partial contraction of the diaphragm.

12. The method of claim 11, further comprising determining the diastolic offset period by:

detecting, over a plurality of cardiac cycles, a time of occurrence of: a) the first cardiac event, b) one of an onset of an atrial event and an offset of a first ventricular event, and c) an onset of a second ventricular event that follows the onset of the atrial event or the onset of the first ventricular event; and processing the respective times of occurrences to calculate a period of time from the first cardiac events to a time between: a) either of an onset of an atrial event or an offset of a first ventricular event, and b) an onset of a second ventricular event that follows the onset of the atrial event and the onset of the first ventricular event, wherein the period of time corresponds to the diastolic offset period.

13. The method of claim 12, wherein:

each of the onset of an atrial event and the offset of a first ventricular event correspond to a detected P wave, and the onset of a second ventricular event corresponds to a detected Q point in a QRS complex, or a detected S1 heart sound.

14. The method of claim 11, further comprising determining the systolic offset period by:

detecting, over a plurality of cardiac cycles, a time of occurrence of: a) the second cardiac event, b) one of an onset of electrical systole, and an onset of mechanical systole, and c) one of an offset of electrical systole, and an offset of mechanical systole; and processing the respective times of occurrences to calculate a period of time from the second cardiac events to a time between: a) either of an onset of electrical systole or an onset of mechanical systole, and b) either of an offset of electrical systole or an offset of mechanical systole, wherein the period of time corresponds to the systolic offset period.

15. The method of claim 14, wherein:

an onset of electrical systole corresponds to a detected Q point in a QRS complex, and an onset of mechanical systole corresponds to a detected S1 hear sound, and an offset of electrical systole corresponds to a detected T wave, and an offset of mechanical systole corresponds to a detected S2 heart sound.

16. The method of claim 11, wherein the first cardiac event and the second cardiac event are a same cardiac event type in consecutive cardiac cycles, the same cardiac event type corresponding to one of an electrical event and a mechanical event.

17. The method of claim 11, wherein the first cardiac event and the second cardiac event are different cardiac events in a same cardiac cycle, each of the different cardiac events corresponding to one of an electrical event and a mechanical event.

* * * * *